(12) United States Patent
Green et al.

(10) Patent No.: US 7,531,542 B2
(45) Date of Patent: May 12, 2009

(54) BENZOOXAZOLE AND BENZOTHIAZOLE ANTAGONISTS OF GONADOTROPIN RELEASING HORMONE RECEPTOR

(75) Inventors: Daniel M. Green, Ambler, PA (US); Diane B. Hauze, Radnor, PA (US); Charles W. Mann, Philadelphia, PA (US); Jeffrey C. Pelletier, Lafayette Hill, PA (US); Matthew D. Vera, Royersford, PA (US)

(73) Assignee: Wyeth, Madison, NJ (US)

( * ) Notice: Subject to any disclaimer, the term of this patent is extended or adjusted under 35 U.S.C. 154(b) by 307 days.

(21) Appl. No.: 11/431,266

(22) Filed: May 9, 2006

(65) Prior Publication Data

US 2006/0264631 A1    Nov. 23, 2006

Related U.S. Application Data

(60) Provisional application No. 60/682,689, filed on May 18, 2005.

(51) Int. Cl.
*A61K 31/497*     (2006.01)
*C07D 413/00*    (2006.01)
*C07D 417/00*    (2006.01)
*C07D 419/00*    (2006.01)

(52) U.S. Cl. .................. 514/254.02; 544/368
(58) Field of Classification Search ............ 514/254.02; 544/368
See application file for complete search history.

(56) References Cited

U.S. PATENT DOCUMENTS

| 3,325,506 | A | 6/1967 | Jones et al. |
|---|---|---|---|
| 3,996,233 | A | 12/1976 | Denzel et al. |
| 4,459,296 | A | 7/1984 | Ancher et al. |
| 4,833,142 | A | 5/1989 | Hartog et al. |
| 5,057,517 | A | 10/1991 | Johnston et al. |
| 5,338,740 | A | 8/1994 | Carpino et al. |
| 5,424,313 | A | 6/1995 | Hartog et al. |
| 5,502,187 | A | 3/1996 | Ayer et al. |
| 5,576,460 | A | 11/1996 | Buchwald et al. |
| 5,643,944 | A | 7/1997 | Garfield et al. |
| 5,716,964 | A | 2/1998 | Hansen, Jr. et al. |
| 6,277,989 | B1 | 8/2001 | Chakravarty et al. |
| 6,306,859 | B1 | 10/2001 | Childers et al. |
| 6,307,087 | B1 | 10/2001 | Buchwald et al. |
| 6,310,066 | B1 | 10/2001 | Kelly et al. |
| 6,313,126 | B1 | 11/2001 | Mewshaw et al. |
| 6,376,141 | B1 | 4/2002 | Mishra et al. |
| 6,399,629 | B1 | 6/2002 | Chamberland et al. |
| 6,476,031 | B1 | 11/2002 | Chakravarty et al. |
| 6,492,517 | B1 | 12/2002 | Burdeniuc |
| 6,548,505 | B1 | 4/2003 | Martin et al. |
| 6,559,167 | B1 | 5/2003 | Garst et al. |
| 6,620,529 | B1 | 9/2003 | Ise et al. |
| 6,696,469 | B2 | 2/2004 | Peglion et al. |
| 6,723,724 | B2 | 4/2004 | Koh et al. |
| 6,821,967 | B2 | 11/2004 | Lehmann-Lintz et al. |
| 6,841,549 | B1 | 1/2005 | Asano et al. |
| 2001/0020030 | A1 | 9/2001 | Stewart et al. |
| 2002/0013324 | A1 | 1/2002 | Childers et al. |
| 2002/0055133 | A1 | 5/2002 | Hahn et al. |
| 2002/0072053 | A1 | 6/2002 | McNally et al. |
| 2002/0147197 | A1 | 10/2002 | Newman et al. |
| 2002/0161010 | A1 | 10/2002 | Chakravarty et al. |
| 2002/0168630 | A1 | 11/2002 | Fleming et al. |
| 2002/0182623 | A1 | 12/2002 | Lefevre et al. |
| 2003/0021851 | A1 | 1/2003 | Goswami et al. |
| 2003/0028018 | A1 | 2/2003 | Renhowe et al. |
| 2003/0051260 | A1 | 3/2003 | Chada et al. |
| 2003/0055057 | A1 | 3/2003 | Blume et al. |
| 2003/0069248 | A1 | 4/2003 | Chakravarty et al. |
| 2003/0165920 | A1 | 9/2003 | Chou et al. |
| 2003/0220365 | A1 | 11/2003 | Stewart et al. |
| 2004/0018240 | A1 | 1/2004 | Ohmachi et al. |
| 2004/0036868 | A1 | 2/2004 | Jones et al. |
| 2004/0082635 | A1 | 4/2004 | Hashimoto et al. |
| 2004/0082798 | A1 | 4/2004 | Alonso-Alija et al. |
| 2004/0102502 | A1 | 5/2004 | Watanabe et al. |
| 2004/0121008 | A1 | 6/2004 | Shiraishi et al. |
| 2004/0122001 | A1 | 6/2004 | Agejas-Chicharro et al. |
| 2004/0219208 | A1 | 11/2004 | Kawamura et al. |
| 2005/0009894 | A1 | 1/2005 | Babin et al. |
| 2005/0065196 | A1 | 3/2005 | Inaba et al. |
| 2005/0101647 | A1 | 5/2005 | Oda et al. |

(Continued)

FOREIGN PATENT DOCUMENTS

DE    39 26 770 A1    2/1991

(Continued)

OTHER PUBLICATIONS

Grundker, et al., Gonadotropin-releasing Hormone Receptor-targeted Gene Therapy of Gynecologic Cancers, Molecular Cancer Therapeutics, 4(2) 225-231 (2005).*

(Continued)

*Primary Examiner*—James O Wilson
*Assistant Examiner*—Erich A Leeser
(74) *Attorney, Agent, or Firm*—Wilmer Cutler Pickering Hale and Dorr LLP

(57) ABSTRACT

The present invention relates to Gonadotropin Releasing Hormone (GnRH, also known as Luteinizing Hormone Releasing Hormone) receptor antagonists.

30 Claims, No Drawings

U.S. PATENT DOCUMENTS

| | | |
|---|---|---|
| 2005/0282820 A1 | 12/2005 | Gontcharov et al. |
| 2006/0019965 A1 | 1/2006 | Garrick et al. |
| 2006/0111355 A1 | 5/2006 | Garrick et al. |
| 2006/0189616 A1 | 8/2006 | Pelletier et al. |
| 2006/0189617 A1 | 8/2006 | Pelletier et al. |
| 2006/0189618 A1 | 8/2006 | Pelletier |
| 2006/0189619 A1 | 8/2006 | Tadayon et al. |
| 2006/0264631 A1 | 11/2006 | Green et al. |
| 2006/0270848 A1 | 11/2006 | Lundquist et al. |

FOREIGN PATENT DOCUMENTS

| | | |
|---|---|---|
| DE | 10030376 | 1/2002 |
| DE | 10110750 | 9/2002 |
| DE | 20217340 | 2/2003 |
| EP | 0138280 | 4/1985 |
| EP | 0300726 | 1/1989 |
| EP | 0400974 | 12/1990 |
| EP | 0434038 | 6/1991 |
| EP | 0 471 236 B1 | 2/1992 |
| EP | 1136483 | 9/2001 |
| EP | 1197485 | 4/2002 |
| EP | 1239283 | 9/2002 |
| GB | 1009807 | 11/1965 |
| GB | 1049330 | 11/1966 |
| GB | 2097790 | 11/1983 |
| GB | 2369616 | 6/2002 |
| GB | 2370270 | 6/2002 |
| IT | 01298727 | 2/2000 |
| JP | 2002161084 | 6/2002 |
| JP | 2002193946 | 7/2002 |
| JP | 2002212101 | 7/2002 |
| JP | 2003040890 | 2/2003 |
| JP | 2003083968 | 3/2003 |
| JP | 2003231687 | 8/2003 |
| NL | 6409237 | 4/1965 |
| NL | 6413475 | 5/1965 |
| RU | 2182708 | 5/2002 |
| WO | WO-9320078 | 10/1993 |
| WO | WO-9907703 | 2/1999 |
| WO | WO-9916755 | 4/1999 |
| WO | WO-9955672 | 11/1999 |
| WO | WO-9962908 | 12/1999 |
| WO | WO-0002887 | 1/2000 |
| WO | WO-0012089 | 3/2000 |
| WO | WO-0040554 | 7/2000 |
| WO | WO-0102369 | 1/2001 |
| WO | WO-0147898 | 7/2001 |
| WO | WO-0149688 | 7/2001 |
| WO | WO-01/57038 | 8/2001 |
| WO | WO-0170728 | 9/2001 |
| WO | WO-0170743 | 9/2001 |
| WO | WO-0174786 | 10/2001 |
| WO | WO-0208221 | 1/2002 |
| WO | WO-0208245 | 1/2002 |
| WO | WO-0214859 | 2/2002 |
| WO | WO-0218383 | 3/2002 |
| WO | WO-0221135 | 3/2002 |
| WO | WO-0222598 | 3/2002 |
| WO | WO-0222600 | 3/2002 |
| WO | WO-0228839 | 4/2002 |
| WO | WO-0230935 | 4/2002 |
| WO | WO-0232422 | 4/2002 |
| WO | WO-0234263 | 5/2002 |
| WO | WO-0235474 | 5/2002 |
| WO | WO-0236562 | 5/2002 |
| WO | WO-0240019 A1 | 5/2002 |
| WO | WO-0240653 | 5/2002 |
| WO | WO-0241906 | 5/2002 |
| WO | WO-0242292 | 5/2002 |
| WO | WO-0243709 | 6/2002 |
| WO | WO-0244168 | 6/2002 |
| WO | WO-0244170 | 6/2002 |
| WO | WO-0245707 | 6/2002 |
| WO | WO-0248152 | 6/2002 |
| WO | WO-0250062 | 6/2002 |
| WO | WO-02051409 | 7/2002 |
| WO | WO-02055012 | 7/2002 |
| WO | WO-02055013 | 7/2002 |
| WO | WO-02059088 | 7/2002 |
| WO | WO-02062949 | 7/2002 |
| WO | WO-02064590 | 8/2002 |
| WO | WO-02068399 | 9/2002 |
| WO | WO-02069901 | 9/2002 |
| WO | WO-02071073 | 9/2002 |
| WO | WO-02072549 | 9/2002 |
| WO | WO-02074340 | 9/2002 |
| WO | WO-02083952 | 9/2002 |
| WO | WO-02076439 | 10/2002 |
| WO | WO-02076926 | 10/2002 |
| WO | WO-02076947 | 10/2002 |
| WO | WO-02076960 | 10/2002 |
| WO | WO-02076976 | 10/2002 |
| WO | WO-02079192 | 10/2002 |
| WO | WO-02079690 | 10/2002 |
| WO | WO-02081463 | 10/2002 |
| WO | WO-02083143 | 10/2002 |
| WO | WO-02083608 | 10/2002 |
| WO | WO-02089738 | 11/2002 |
| WO | WO-02101087 | 11/2002 |
| WO | WO-02102774 | 12/2002 |
| WO | WO-02102978 | 12/2002 |
| WO | WO-03004023 | 1/2003 |
| WO | WO-03004488 | 1/2003 |
| WO | WO-03007945 | 1/2003 |
| WO | WO-03013488 | 2/2003 |
| WO | WO-03013609 | 2/2003 |
| WO | WO-03018835 | 2/2003 |
| WO | WO-03/022214 | 3/2003 |
| WO | WO-03018835 | 3/2003 |
| WO | WO-03021851 | 3/2003 |
| WO | WO-03024401 | 3/2003 |
| WO | WO-03025563 | 3/2003 |
| WO | WO-03026664 | 4/2003 |
| WO | WO-03026665 | 4/2003 |
| WO | WO-03026666 | 4/2003 |
| WO | WO-03027223 | 4/2003 |
| WO | WO-03031436 | 4/2003 |
| WO | WO-03032984 | 4/2003 |
| WO | WO-03035065 | 5/2003 |
| WO | WO-03035644 | 5/2003 |
| WO | WO-03037871 | 5/2003 |
| WO | WO-03037872 | 5/2003 |
| WO | WO-03038401 | 5/2003 |
| WO | WO-03048140 | 6/2003 |
| WO | WO-03053939 A1 | 7/2003 |
| WO | WO-03053948 | 7/2003 |
| WO | WO-03068754 | 8/2003 |
| WO | WO-03070943 | 8/2003 |
| WO | WO-03082272 | 10/2003 |
| WO | WO-03091408 | 11/2003 |
| WO | WO-03095432 | 11/2003 |
| WO | WO-03095995 | 11/2003 |
| WO | WO-2004016611 | 2/2004 |
| WO | WO-2004035549 | 4/2004 |

OTHER PUBLICATIONS

Buchwald, et al., "Long-term, Continuous Intravenous Heparin Administration by an Implantable Infusion Pump in Ambulatory Patients with Recurrent Venous Thrombosis", Surgery, 88(4):507-516 (1980).

Bundgaard, "Design and Application of Prodrugs", in *Textbook of Drug Design and Development*, Kgrogsgaard-Larsen, et al., eds., Harwood Academic Publishers, Chapter 5, pp. 113-191 (1991).
Clayton, et al., "Receptor-Binding Affinity of Gonadotropin-Releasing Hormone Analogs: Analysis by Radioligand-Receptor Assay", Endocrinology, 106(4):1154-1159 (1980).
*Controlled Drug Bioavailability, Drug Product Design and Performance*, Smolen, et al., eds., John Wiley & Sons (1984).
*Design of Prodrugs*, Bundgaard, ed., Elsevier (1985).
During, et al., "Controlled Release of Dopamine from a Polymeric Brain Implant: In Vivo Characterization", Ann. Neural., 25(4):351-356 (1989).
Enuguehard, et al., Ipso- or Cine-Substitutions of 6-Haloimidazo[1,2-a]pyridine Derivatives with Different Azoles Depending on the Reaction Conditions, J. Org. Chem, 68:5614-5617 (2003).
Finkelstein, "Regioselective Lithiation and Reaction of [1,2,4]Triazolo[1,5-a]pyridine and Pyrazolo[1,5-a]pyridine", J. Org. Chem., 57:5538-5540 (1992).
Goodson, "Dental Applications", *Medical Applications of Controlled Release*, vol. 2, Langer, et al,. eds., CRC Press, Boca Raton, FL, pp. 115-138 (1984).
Gudmundsson, et al., "Synthesis of Novel Imidazo[1,2-a]pyridines with Potent Activity Against Herpesviruses", Org. Lett, 5(8):1369-1372 (2003).
Howard III, et al., "Intracerebral Drug Delivery in Rats with Lesion-Induced Memory Deficits", J. Neurosurg., 71:105-112 (1989).
Langer, "New Methods of Drug Delivery", Science, 249:1527-1533 (1990).
Langer, et al., "Chemical and Physical Structure of Polymers as Carriers for Controlled Release of Bioactive Agents: A Review", J. Macromol. Sci. Rev. Macromol. Chem., C23(1):61-126 (1983).
Levy, et al., "Inhibition of Calcification of Bioprosthetic Heart Valves by Local Controlled-Release Diphosphonate", Science, 228:190 (1985).
Lopez-Berestein, "Treatment of Systemic Fungal Infections with Liposomal-Amphotericin B", *Liposomes in the Therapy of Infectious Diseases and Cancer*, pp. 317-327 (1989).
March, *Advanced Organic Chemistry: Reactions, Mechanisms and Structures, Fourth Edition*, John Wiley & Sons, pp. 69-74 (1992).
*Medical Applications of Controlled Release*, Langer, et al., eds. , CRC Press, Boca Raton, FL (1984).
*Methods in Enzymology*, vol. 112, Widder, et al., eds., Academic Press (1985).
Nielsen, et al., "Glycolamide Esters as Biolabile Prodrugs of Carboxylic Acid Agents: Synthesis, Stability, Bioconversion, and Physiochemical Properties", J. Pharmaceutical Sciences, 77(4):285-298 (1988).
*Prodrugs as Novel Drug Delivery Systems*, Higuchi, et al., eds., American Chemical Society, Washington, DC (1975).
Radebaugh, et al., "Preformulation", *Remington: The Science and Practice of Pharmacy, 19th Edition*, Gennaro, ed., pp. 1447-1676 (1995).
Saudek, et al., "A Prelminiary Trial of the Programmable Implantable Medication System for Insulin Delivery", New England Journal of Med., 321(9):574-579 (1989).
Sefton, "Implantable Pumps", CRC Crit. Ref. Biomed. Eng, 14(3):201-240 (1987).
Treat, et al., "Liposome Encapsulated Doxorubicin Preliminary Results of Phase I and Phase II Trials", *Liposomes in the Therapy of Infectious Diseases and Cancer*, pp. 353-365 (1989).
Armer, R.E, et al., "Non-Peptidic GnRH Receptor Antagonists," Current Medicinal Chemistry, 2004, 11, 3017-3028.
Chengalvala, M.V. et al., "GnRH Agonists and Antagonists in Cancer Therapy," Curr. Med. Chem.—Anti-Cancer Agents, 2003, 3, 399-410.
Hirsch, L. et al., "Birth Control: Birth Control Pill," TeensHealth, Nemours Foundation, http://kidshealth.org/teen/sexual_health/contraception/contraception_birth.html, Jul. 2, 2008.
Artamonova, et al., "Preparation of 1,5-Disubstituted Tetrazoles Under Phase-Transfer Conditions", Synthesis (1996) 12, 1428-30.
Barraclough et al. "INOTROPIC 'A' Ring Substituted Sulmazole and Isomazole Analogues," J. Med. Chem., 1999, 33, 2231-2239.

Dandegaonker, et al., "Brom-hydroxychalkone", Monatshefte fuer Chemie 96(2), (1965) 450-60.
Decroix, et al., "Synthese de Composes Polyazotes a Partir de Nitrile ou D'iminoether Furannique, Thiophenique et Selenophenique", Bulletin de la Societe Chimique de France (1976) (3-4, Pt. 2) 621-7.
Dorwald F. A., *Side Reactions in Organic Synthesis*, Wiley: VCH Weinheim, p. IX of Preface (2005).
Dox, A.W. "Acetamidine Hydrochloride," Organic Syntheses, 1932, pp. 5-7.
Edlin, et al., "Selective Solvent Extraction of Tetrahedrally-Coordinating Transition Metal Ions From Acidic Aqueous Media Using Benzimidazole-Phosphinate Ligands: Specifıcty for Zinc(II) Over Copper(II)", New Journal of Chemistry 23(8) (1999) 819-26.
Gilchrist, et al., "Cyclisations of Ortho-Substituted N-Arylbenzimidoyl Nitrenes. Part 1. Cyclisations With Ortho-Alkyl Substituents: Skeletal Rearrangements and [1,9]Alkyl Migrations", J. Chem. Soc. Perkin Trans. I (1979) 1871-73.
Grenda, et al., "Novel Preparation of Benzimidazoles From N-Arylamidines. New Synthesis of Thiabendazole", J. Org. Chem. (1965) 30(1) 259-61.
Harris, et al., "Improved Functional Group Compatibility in the Palladium-Catalyzed Synthesis of Aryl Amines", Org. Lett. (2002) 4, 2885-8.
Haruki et al., "The Preparation of 2-Substituted Benzimidazoles and 2-Phenylnaphtho-[1, 2-d]imidazole From N-Arylamidines", Bull. Chem. Soc. Japan (1965) 38(10), 1805.
Haruki, et al., "Some Reactions of N-Haloamidines", Bull. Chem. Soc. Japan (1968) 41, 1361-67.
Hisano, et al., "Synthesis of Benzoxazoles, Benzothiazoles and Benzimidazoles and Evaluation of Their Antifungal, Insecticidal and Herbicidal Activities", Chem. Pharm. Bull. (1982) 30(8), 2996-3004.
Ichikawa, et al., "Acidic Properties of Benzimidazoles and Substituent Effects. III: The Substituent Effect on the Imidazole Cyclization From N-(*m*-Substituted-Phenyl) Picolylamidines", Organic Preparations and Procedures International (1979) 10(5), 205-9.
Ichikawa, et al., "Acidic Properties of Benzimidazoles and Substituent Effects. IV. Relationship Between the Acidities of N'-(Substituted Phenyl) Arylamidines and Ring Closures to Imidazole", Chem. Pharm. Bull. (1979) 27(5), 1255-64.
Katritzky, et al., "Pyrazolo (1,5-c)Pyrimidines From Pyrylium Salts And Amidrazones And Pyridine Imidoyl-N-Imides From Imidoyl Chlorides", Heterocycles (1982) 18, 21-28.
Liu, et al., "A Particularly Convenient Preparation of Benzohydroximinoyl Chlorides (Nitrile Oxide Precursors)", J. Org. Chem. (1980) 45, 3916-18.
López-Rodriguez, et al., "Design and Synthesis of New Benzimidazole-Arylpiperazine Derivatives Acting as Mixed 5-$HT_{1A}$/5-$HT_3$ Ligands", *Bioorg. & Med. Chem. Letters* (2003) vol. 13, 3177-80.
López-Rodriguez, et al., "Design and Synthesis of *S*-(−)-2-[[4-(napht-1-yl)piperazin-1-yl]-methyl]-1,4-dioxoperhydropyrrolo[1,2-*a*]pyrazine (CSP-2503) Using Computational Simulation. A 5-$HT_{1A}$ Receptor Agonist", *Bioorg. & Med. Chem. Letters* (2003) vol. 13, 1429-32.
López-Rodriguez, et al., "Pd(0) Amination of Benzimidazoles as an Efficient Method towards New (Benzimidazolyl) piperazines with High Affinity for the 5-HT1A Receptor", Tetrahedron 56 (2000) 3245-53.
López-Rodriguez, et al., "Synthesis of New (Benzimidazolyl) Piperazines with Affinity for the 5-HT1A Receptor Via Pd(0) Amination of Bromobenzimidazoles", Bioorg. & Med. Chem. Letters (1999) vol. 9, 2339-42.
Medical Applications of Controlled Release, vol. I and II, Langer and Wise, eds., CRC Press, Inc., Boca Raton, FL (1984).
Mewshaw, et al., "New Generation Dopaminergic Agents. 5. Heterocyclic Bioisosteres That Exploit The 3-OH-N1-Phenylpiperazine Dopaminergic Template", Bioorg. & Med. Chem. Letters (1998) vol. 8, 2675-80.
Partridge, et al., "Cyclic Amidines. Part VII. Preparation of Benziminazoles From N'-Aryl-N-Hydroxyamidines", J. Chem. Soc. (1958) 2086-92.

Radebaugh, et al., "Preformulation", Remington: The Science and Practice of Pharmacy, 19th Edition, Gennaro, Ed., pp. 1447-1462 (1995).

Ramsden, et al., "Rearrangement and Cyclo-α-Elimination of N-Substituted Amidines Using (Diacetoxyiodo) Benzene", J. Chem. Soc. Perkin Trans. I (1995) 615-17.

Smith, et al., "Amidrazones III. The Synthesis And Properties of 1,1,1-Trimethyl-2-(N-Phenlbenzimidoyl)Hydrazinium Hydroxide Inner Salt—A Novel Ylid", Tetrahedron Lett. (1973) 3941-42.

Smith, et al., "The Thermal Breakdown of Diaryltetrazoles", J. Am. Chem. Soc. (1958) 80, 4647-54.

Wolfe, et al., "Simple, Efficient Catalyst System For The Palladium-Catalyzed Amination of Aryl Chlorides, Bromides, and Triflates", J. Org. Chem. (2000) 65, 1158-74.

* cited by examiner

BENZOOXAZOLE AND BENZOTHIAZOLE ANTAGONISTS OF GONADOTROPIN RELEASING HORMONE RECEPTOR

This application claims the benefit of provisional application U.S. Ser. No. 60/682,689, filed May 18, 2005, which is hereby incorporated by reference into the subject application in its entirety.

Throughout this application, various publications are referenced. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure, as it appears in the U.S. Patent and Trademark Office patent file or records, but otherwise reserves any and all copyright rights whatsoever.

FIELD OF THE INVENTION

The present invention relates to Gonadotropin Releasing Hormone (GnRH, also known as Luteinizing Hormone Releasing Hormone) receptor antagonists.

BACKGROUND OF THE INVENTION

Gonadotropin Releasing Hormone is a decameric peptide released from the hypothalamus. In the anterior pituitary gland, GnRH activates the GnRH receptor. Activation of the GnRH receptor triggers the release of follicle stimulating hormone (FSH) and luteinizing hormone (LH). FSH and LH stimulate the biosynthesis and release of sex steroids in the gonads of both genders.

Typically, this stimulation and release is desirable, but certain GnRH-related disorders exist where it would be beneficial to prevent activation of the GnRH receptor. For example, inhibition of the GnRH receptor can lead to a large drop in sex steroid production, which in turn can alleviate sex hormone-related conditions such as prostate cancer, endometriosis, uterine fibroids, uterine cancer, breast cancer, ovarian cancer, testicular cancer, or primary hirsutism. Moreover, there are other situations where it would be beneficial to prevent activation of the GnRH receptor, such as during some points of the in vitro fertilization process, for example, to prevent LH surge.

Currently marketed GnRH therapeutics are peptides that exhibit receptor antagonism in one of two ways. The first is through GnRH receptor superagonism. The GnRH receptor, when stimulated in bursts, causes normal relase of the gonadotropins, FSH and LH. Under constant stimulation, the receptor becomes desensitized and the overall effect is GnRH receptor inhibition. The superagonism process is undesirable, because inhibition via this process can take up to two weeks to have an effect in human patients. During this delay, there is often an increase in disease symptoms due to the initial hormone stimulation phase. This phenomenon is referred to as flare.

The second method for receptor inhibition is through direct antagonism of the GnRH receptor with peptide antagonists. This causes an immediate drop in plasma LH levels. However, as mentioned above, current pharmaceuticals that cause blockade of the GnRH receptor are all peptides. As such they are not orally bioavailable and must be administered via parenteral means such as intravenous, subcutaneous, or intramuscular injection. Thus, an orally effective GnRH antagonist would be of great benefit.

The present invention is directed to these and other important ends.

SUMMARY OF THE INVENTION

In one embodiment, the invention provides compounds of the Formula (I):

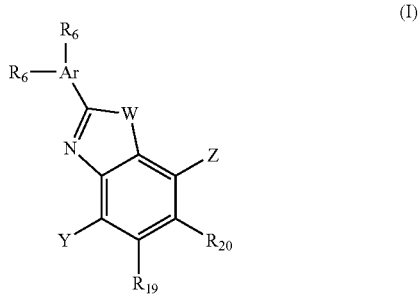

and pharmaceutically acceptable salts thereof,
wherein
W is O or S;
Y is Q and Z is $R_{18}$; or Y is $R_{18}$ and Z is Q, wherein Q is

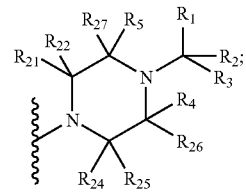

Ar is phenyl, 2-thiophenyl or 3-thiophenyl;

$R_1$ and $R_2$ are each independently hydrogen; or linear or branched $(C_1-C_6)$-alkyl, $(C_2-C_6)$-alkenyl, or $(C_2-C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, or $-CON(R_{23})_2$; or $R_1$ and $R_2$ may together form a three- to seven-membered cycloalkyl group, wherein the cycloalkyl group formed by $R_1$ and $R_2$ is optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, $-CON(R_{23})_2$, or $-(CH_2)_nOR_{23}$;

$R_3$ is one of the following:

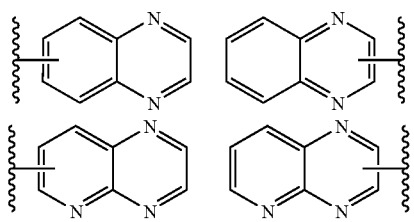

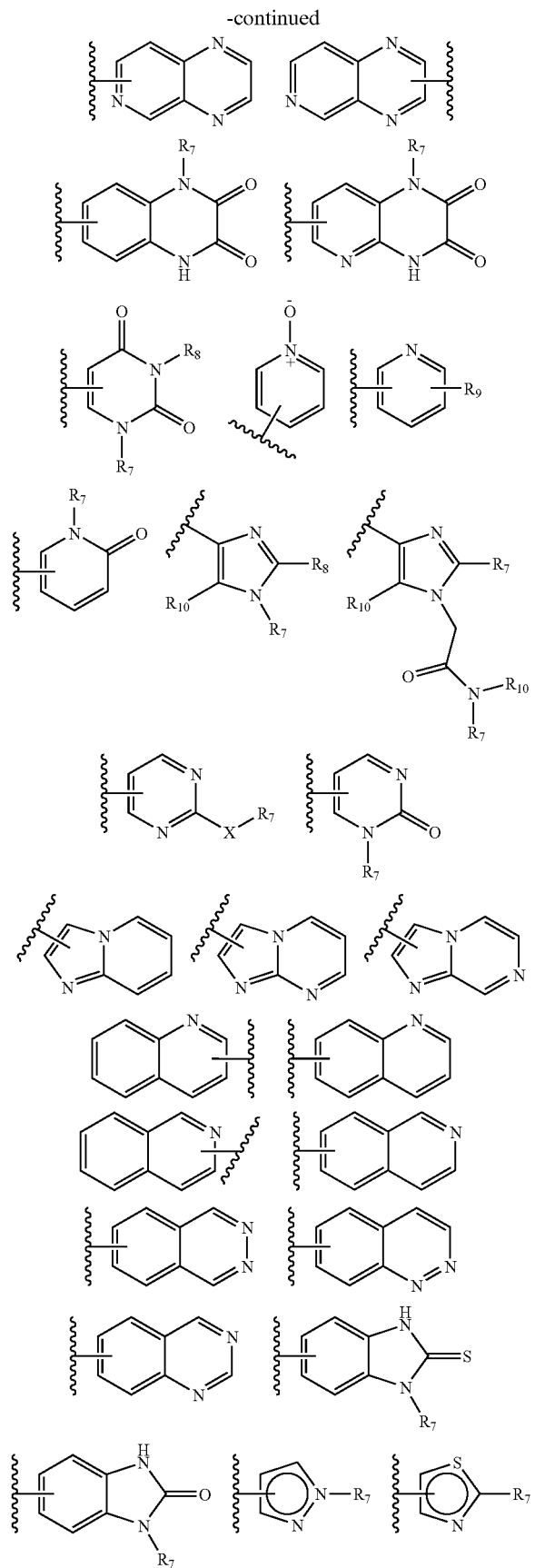
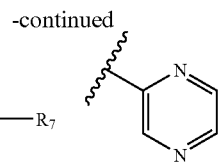

each $R_3$ also having up to three $R_{10}$ substituents attached to the ring of $R_3$ containing at least one N;

$R_4$, $R_5$, $R_{10}$, $R_{21}$, $R_{22}$, $R_{23}$, $R_{24}$, $R_{25}$, $R_{26}$, and $R_{27}$ are each independently hydrogen; or linear or branched $(C_1$-$C_6)$-alkyl, $(C_2$-$C_6)$-alkenyl, or $(C_2$-$C_6)$-alkynyl;

each $R_6$ is independently hydrogen; linear or branched $(C_1$-$C_6)$-alkyl, $(C_2$-$C_6)$-alkenyl, or $(C_2$-$C_6)$-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; —$NR_{13}R_{14}$; —C(OH)(CF$_3$)$_2$; —CH(CF$_3$)$_2$; —C(CF$_3$)$_3$; —$XR_{13}$; or —$COR_{13}$; and when two $R_6$ are ortho to each other, they may together form a five- to seven-membered cyclic group containing up to 3 heteroatoms selected from N, O, or S, and wherein the cyclic group formed by the ortho $R_6$ groups is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_7$ and $R_9$ are each independently hydrogen; linear or branched $(C_1$-$C_6)$-alkyl, $(C_2$-$C_6)$-alkenyl, or $(C_2$-$C_6)$-alkynyl; —$(CH_2)_nXR_{12}$; —$(CH_2)_nR_{17}$; —$COXR_{11}$; —$XR_{11}$; —$CO_2R_{11}$; or —$CONR_{11}R_{12}$;

$R_8$ is hydrogen; linear or branched $(C_1$-$C_6)$-alkyl, $(C_2$-$C_6)$-alkenyl, or $(C_2$-$C_6)$-alkynyl; —$(CH_2)_mCO_2R_{11}$; or —$(CH_2)_mCONR_{11}R_{12}$;

$R_{11}$ and $R_{12}$ are each independently hydrogen; linear or branched $(C_1$-$C_6)$-alkyl, $(C_2$-$C_6)$-alkenyl, or $(C_2$-$C_6)$-alkynyl; or $R_{11}$ and $R_{12}$ may together form a three- to seven-membered heterocyclic group containing up to 3 heteroatoms selected from N, O, or S;

$R_{13}$ and $R_{14}$ are each independently hydrogen; linear or branched $(C_1$-$C_6)$-alkyl, $(C_2$-$C_6)$-alkenyl, or $(C_2$-$C_6)$-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$R_{23}CO_2R_{23}$, —$NR_{23}COR_{23}$, —$NR_{23}CON(R_{23})_2$, or —$CON(R_{23})_2$; aryl; or aryl optionally substituted with one to three substituents selected from halogen, $R_{15}$, —$OR_{15}$, or —$NR_{15}R_{16}$; or $R_{13}$ and $R_{14}$ may together form a three- to seven-membered heterocyclic group containing up to 3 heteroatoms selected from N, O, or S, and wherein the heterocyclic group formed by $R_{13}$ and $R_{14}$ is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_{15}$ and $R_{16}$ are each independently hydrogen; or linear or branched $(C_1$-$C_6)$-alkyl, $(C_2$-$C_6)$-alkenyl, or $(C_2$-$C_6)$-alkynyl; or both $R_{15}$ and $R_{16}$ may together form a three- to seven-membered heterocyclic group containing up to 3 heteroatoms selected from N, O, or S;

$R_{17}$ is phenyl, 2-pyridyl, 3-pyridyl, or 4-pyridyl;

$R_{18}$, $R_{19}$, and $R_{20}$ are each independently hydrogen; linear or branched $(C_1$-$C_6)$-alkyl, $(C_2$-$C_6)$-alkenyl, or $(C_2$-$C_6)$- alkynyl, each optionally substituted with halogen, —N₃, —NO₂, —CN, —OR₂₃, —SR₂₃, —SO₂R₂₃, —SO₂N(R₂₃)₂, —N(R₂₃)₂, —COR₂₃, —CO₂R₂₃, —NR₂₃CO₂R₂₃, —NR₂₃COR₂₃, —NR₂₃CON(R₂₃)₂, or —CON(R₂₃)₂; halogen; —NR₁₃R₁₄; —C(OH)(CF₃)₂; —CH(CF₃)₂; —C(CF₃)₃; —XR₁₃; —COR₁₃; —CO₂R₁₃; or —CON(R₁₃)(R₁₄);

X is —O—, —NR₁₂—, or —SO$_m$—;
each m is independently 0, 1, or 2; and
each n is independently 0, 1, 2, 3, or 4.

In another embodiment, the invention provides compounds of the Formula (II):

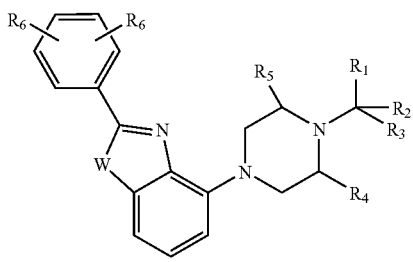

(II)

and pharmaceutically acceptable salts thereof, wherein each of W, R₁, R₂, R₃, R₄, R₅, and R₆ are as described above for compounds of the Formula (I).

In another embodiment, the compounds or pharmaceutically acceptable salts of the compounds of Formula (I) or Formula (II) are useful as pharmaceutical compositions comprising compounds or pharmaceutically acceptable salts of compounds of Formula (I) or Formula (II) and a pharmaceutically acceptable carrier.

In one embodiment, the compounds or pharmaceutically acceptable salts of the compounds of the Formula (I) or Formula (II) are useful as GnRH receptor antagonists.

In one embodiment, the invention provides methods for treating a GnRH-related disorder, comprising administering to a mammal in need thereof the compounds or pharmaceutically acceptable salts of compounds of Formula (I) or Formula (II) in an amount effective to treat a GnRH-related disorder. In another embodiment, the invention provides methods for preventing pregnancy, comprising administering to a female mammal the compounds or pharmaceutically acceptable salts of compounds of the Formula (I) or Formula (II) in an amount effective to prevent pregnancy.

In one embodiment, the invention provides methods of synthesizing the compounds or pharmaceutically acceptable salts of compounds of Formula (I) or Formula (II). In another embodiment, the invention provides compounds or pharmaceutically acceptable salts of compounds of Formula (I) or Formula (II) made by particular processes.

DESCRIPTION OF THE INVENTION

Definitions

The term "(C₁-C₆)-alkyl" as used herein refers to a linear or branched, saturated hydrocarbon having from 1 to 6 carbon atoms. Representative (C₁-C₆)-alkyl groups include, but are not limited to, methyl, ethyl, propyl, isopropyl, butyl, sec-butyl, tert-butyl, pentyl, isopentyl, neopentyl, hexyl, isohexyl, and neohexyl. In one embodiment, the (C₁-C₆)-alkyl group is substituted with one or more of the following groups: halogen, —N₃, —NO₂, —CN, —OR', —SR', —SO₂R', —SO₂N(R')₂, —N(R')₂, —COR', —CO₂R', —NR'CO₂R', —NR'COR', —NR'CONR', or —CON(R')₂, wherein each R' is independently hydrogen or unsubstituted (C₁-C₆)-alkyl.

The term "(C₂-C₆)-alkenyl" as used herein refers to a linear or branched hydrocarbon having from 2 to 6 carbon atoms and having at least one carbon-carbon double bond. In one embodiment, the (C₂-C₆)-alkenyl has one or two double bonds. The (C₂-C₆)-alkenyl moiety may exist in the E or Z conformation and the compounds of the present invention include both conformations. In one embodiment, the (C₂-C₆)-alkenyl group is substituted with one or more of the following groups: halogen, —N₃, —NO₂, —CN, —OR', —SR', —SO₂R', —SO₂N(R')₂, —N(R')₂, —COR', —CO₂R', —NR'CO₂R', —NR'COR', —NR'CONR', or —CON(R')₂, wherein each R' is independently hydrogen or unsubstituted (C₁-C₆)-alkyl.

The term "(C₂-C₆)-alkynyl" as used herein refers to a linear or branched hydrocarbon having from 2 to 6 carbon atoms and having at least one carbon-carbon triple bond. In one embodiment, the (C₂-C₆)-alkenyl group is substituted with one or more of the following groups: halogen, —N₃, —NO₂, —CN, —OR', —SR', —SO₂R', —SO₂N(R')₂, —N(R')₂, —COR', —CO₂R', —NR'CO₂R', —NR'COR', —NR'CONR', or —CON(R')₂, wherein each R' is independently hydrogen or unsubstituted (C₁-C₆)-alkyl.

The term "administer", "administering", or "administration", as used herein refers to either directly administering a compound or pharmaceutically acceptable salt of the compound or a composition to an animal, or administering a prodrug derivative or analog of the compound or pharmaceutically acceptable salt of the compound or composition to the animal, which can form an equivalent amount of active compound within the animal's body.

The term "animal" as used herein includes, without limitation, a human, mouse, rat, guinea pig, dog, cat, horse, cow, pig, monkey, chimpanzee, baboon, or rhesus. In one embodiment, the animal is a mammal. In another embodiment, the animal is a human.

The term "amine protecting group" as used herein refers to a moiety that temporarily blocks an amine reactive site in a compound. Generally, this is done so that a chemical reaction can be carried out at another reactive site in a multifunctional compound or to otherwise stabilize the amine. In one embodiment, an amine protecting group is selectively removable by a chemical reaction. An exemplary amine protecting group is a carbamate protecting group. Carbamate protecting groups include, without limitation, t-butyl carbamate, methyl carbamate, ethyl carbamate, 2,2,2-trichloroethyl carbamate, 2-(trimethylsilyl)ethyl carbamate, 1,1-dimethyl-2,2,2-trichloroethyl carbamate, benzyl carbamate, p-methoxybenzyl carbamate, p-nitrobenzylcarbamate, p-bromobenzyl carbamate, p-chlorobenzyl carbamate, and 2,4-dichlorobenzyl carbamate. See, Greene and Wuts, *Protecting Groups in Organic Synthesis*, Second Edition, John Wiley & Sons (1991).

The term "aryl" as used herein refers to an aromatic species containing 1 to 3 aromatic rings, either fused or linked. In one embodiment, the aryl group is substituted with one or more of the following groups: (C₁-C₆)alkyl, —V-halogen, —V—N₃, —V—NO₂, —V—CN, —V—OR', —V—SR', —V—SO₂R', —V—SO₂N(R')₂, —V—N(R')₂, —V—COR', —V—CO₂R', —V—NR'CO₂R', —V—NR'COR', —V—NR'CONR', or —V—CON(R')₂, wherein each R' is independently hydrogen or unsubstituted (C₁-C₆)-alkyl; and wherein each V is independently a bond or (C₁-C₆)-alkyl. An aryl group can optionally include one or more heteroatoms selected from N, O, or S.

The term "conditions effective to" as used herein refers to synthetic reaction conditions which will be apparent to those skilled in the art of synthetic organic chemistry.

The term "cyclic group" as used herein includes a cycloalkyl group and a heterocyclic group. Any suitable ring position of the cyclic group may be covalently linked to the defined chemical structure. In one embodiment, the cyclic group is substituted with one or more of the following groups: $(C_1-C_6)$alkyl, —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', or —V—CON(R')$_2$, wherein each R' is independently hydrogen or unsubstituted $(C_1-C_6)$-alkyl; and wherein each V is independently a bond or $(C_1-C_6)$-alkyl.

The term "cycloalkyl group" as used herein refers to a three- to seven-membered saturated or partially unsaturated carbon ring. Any suitable ring position of the cycloalkyl group may be covalently linked to the defined chemical structure. Exemplary cycloalkyl groups include cyclopropyl, cyclobutyl, cyclopentyl, cyclohexyl, and cycloheptyl. In one embodiment, the cycloalkyl group is substituted with one or more of the following groups: $(C_1-C_6)$alkyl, —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', or —V—CON(R')$_2$, wherein each R' is independently hydrogen or unsubstituted $(C_1-C_6)$-alkyl; and wherein each V is independently a bond or $(C_1-C_6)$-alkyl.

The term "effective amount" as used herein refers to an amount of a compound or pharmaceutically acceptable salt of a compound that, when administered to an animal, is effective to prevent, to at least partially ameliorate, or to cure, a condition from which the animal suffers or is suspected to suffer.

The term "FSH" as used herein refers to follicle stimulating hormone.

The term "GnRH" as used herein refers to Gonadotropin Releasing Hormone.

The term "Gonadotropin Releasing Hormone-related disorder" or "GnRH-related disorder" as used herein refers to a condition for which it would be beneficial to prevent activation of the GnRH receptor. Exemplary GnRH-related disorders include, without limitation, sex hormone-related conditions, sex hormone-dependent cancers, prostate cancer, testicular cancer, uterine cancer, ovarian cancer, breast cancer, pituitary gonadotrophe adenomas, endometriosis, polycystic ovarian disease, uterine fibroids, primary hirsutism, luteinizing hormone surge, and precocious puberty.

The term "LH" as used herein refers to luteinizing hormone.

The term "halogen" as used herein refers to fluorine, chlorine, bromine, and iodine.

The term "heterocyclic group" as used herein refers to a three- to seven-membered saturated, partially saturated, or unsaturated cycloalkyl group in which one to four of the ring carbon atoms have been independently replaced with a N, O, or S atom. Any suitable ring position of the heterocyclic group may be covalently linked to the defined chemical structure. Exemplary heterocyclic groups include, but are not limited to, azepanyl, azetidinyl, aziridinyl, furanyl, furazanyl, homopiperazinyl, imidazolidinyl, imidazolinyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, and triazolyl. In one embodiment, the heterocyclic group is substituted with one or more of the following groups: $(C_1-C_6)$alkyl, —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', or —V—CON(R')$_2$, wherein each R' is independently hydrogen or unsubstituted $(C_1-C_6)$-alkyl; and wherein each V is independently a bond or $(C_1-C_6)$-alkyl.

The term "isolated and purified" as used herein refers to an isolate that is separate from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

The term "pharmaceutically acceptable salt" as used herein refers to a salt of an acid and a basic nitrogen atom of a compound of the present invention. Exemplary salts include, but are not limited to, sulfate, citrate, acetate, oxalate, chloride, hydrochloride, bromide, hydrobromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, succinate, fumarate, maleate, malonate, mandelate, malate, phthalate, and pamoate. The term "pharmaceutically acceptable salt" as used herein also refers to a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2—OH—$(C_1-C_6)$-alkylamine), such as N,N-dimethyl-N-(2-hydroxyethyl)amine or tri-(2-hydroxyethyl) amine; N-methyl-D-glucamine; morpholine; thiomorpholine; piperidine; pyrrolidine; and amino acids such as arginine, lysine, and the like. The term "pharmaceutically acceptable salt" also includes a hydrate of a compound of the present invention.

The term "phenyl" as used herein refers to a substituted or unsubstituted phenyl group. In one embodiment, the phenyl group is substituted with one or more of the following groups:

($C_1$-$C_6$)alkyl, —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', or —V—CON(R')$_2$, wherein each R' is independently hydrogen or unsubstituted ($C_1$-$C_6$)-alkyl; and wherein each V is independently a bond or ($C_1$-$C_6$)-alkyl.

The term "substantially free of its corresponding opposite enantiomer" as used herein means that the compound contains no more than about 10% by weight of its corresponding opposite enantiomer. In other embodiments, the compound that is substantially free of its corresponding opposite enantiomer contains no more than about 5%, no more than about 1%, no more than about 0.5%, or no more than about 0.1% by weight of its corresponding opposite enantiomer. An enantiomer that is substantially free of its corresponding opposite enantiomer includes a compound that has been isolated and purified or has been prepared substantially free of its corresponding opposite enantiomer.

The term "tautomer" as used herein refers to compounds produced by the phenomenon wherein a proton of one atom of a molecule shifts to another atom. See, Jerry March, *Advanced Organic Chemistry: Reactions, Mechanisms and Structures*, Fourth Edition, John Wiley & Sons, pages 69-74 (1992).

The following abbreviations as used herein mean: Ac is acetate; boc is t-butyl carbamate; Bu is butyl; dba is dibenzylideneacetone; DCE is 1,2-dichloroethane; DCM is dichloromethane; DIEA is diisopropylethylamine; DMF is dimethylformamide; DMSO is dimethylsulfoxide; ESI is electrospray ionization; Et is ethyl; HPLC is high pressure liquid chromatography; HRMS is high resolution mass spectrometry; LCMS is liquid chromatograph-mass spectrometry; Me is methyl; MS is mass spectrometry; m/z is mass-to-charge ratio; NMP is N-methylpyrrolidine; NMR is nuclear magnetic resonance; r.t. is retention time; TFA is trifluoroacetic acid; THF is tetrahydrofuran.

Compounds and Pharmaceutically Acceptable Salts of Compounds of the Invention

The compounds or pharmaceutically acceptable salts of compounds of the present invention can contain an asymmetric carbon atom and some of the compounds or pharmaceutically acceptable salts of compounds of the invention can contain one or more asymmetric centers, and can thus give rise to optical isomers and diastereomers. While depicted without respect to stereochemistry in the compounds or pharmaceutically acceptable salts of compounds of the present invention, the present invention includes such optical isomers and diastereomers, as well as racemic and resolved, enantiomerically pure R and S stereoisomers, and also other mixtures of the R and S stereoisomers and pharmaceutically acceptable salts thereof. Where a stereoisomer is provided, it can in some embodiments be provided substantially free of its corresponding opposite enantiomer.

In addition, the compounds and pharmaceutically acceptable salts of compounds of the present invention can exist as tautomers. Such tautomers can be transient or isolatable as a stable product. These tautomers are within the scope of the present invention.

Prodrugs of the compounds or pharmaceutically acceptable salts of compounds are also within the scope of the present invention.

Compounds of the Formula (I)

In one embodiment, the present invention is directed to compounds of the Formula (I):

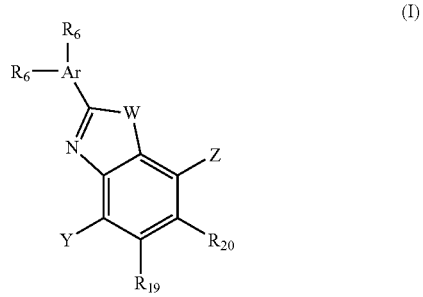

(I)

and pharmaceutically acceptable salts thereof,
wherein
W is O or S;
Y is Q and Z is $R_{18}$; or Y is $R_{18}$ and Z is Q, wherein Q is

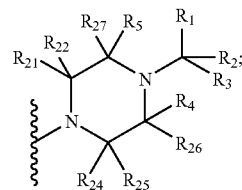

Ar is phenyl, 2-thiophenyl or 3-thiophenyl;
$R_1$ and $R_2$ are each independently hydrogen; or linear or branched ($C_1$-$C_6$)-alkyl, ($C_2$-$C_6$)-alkenyl, or ($C_2$-$C_6$)-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; or $R_1$ and $R_2$ may together form a three- to seven-membered cycloalkyl group, wherein the cycloalkyl group formed by $R_1$ and $R_2$ is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;
$R_3$ is one of the following:

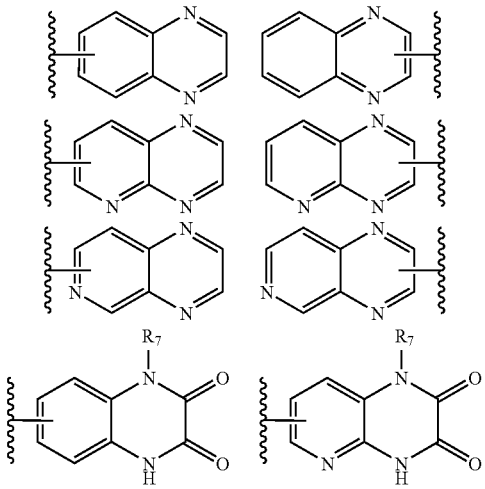

each $R_3$ also having up to three $R_{10}$ substituents attached to the ring of $R_3$ containing at least one N;

$R_4$, $R_5$, $R_{10}$, $R_{21}$, $R_{22}$, $R_{23}$, $R_{24}$, $R_{25}$, $R_{26}$, and $R_{27}$ are each independently hydrogen; or linear or branched ($C_1$-$C_6$)-alkyl, ($C_2$-$C_6$)-alkenyl, or ($C_2$-$C_6$)-alkynyl;

each $R_6$ is independently hydrogen; linear or branched ($C_1$-$C_6$)-alkyl, ($C_2$-$C_6$)-alkenyl, or ($C_2$-$C_6$)-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; —$NR_{13}R_{14}$; —C(OH)($CF_3$)$_2$; —CH($CF_3$)$_2$; —C($CF_3$)$_3$; —$XR_{13}$; or —$COR_{13}$; and when two $R_6$ are ortho to each other, they may together form a five- to seven-membered cyclic group containing up to 3 heteroatoms selected from N, O, or S, and wherein the cyclic group formed by the ortho $R_6$ groups is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_7$ and $R_9$ are each independently hydrogen; linear or branched ($C_1$-$C_6$)-alkyl, ($C_2$-$C_6$)-alkenyl, or ($C_2$-$C_6$)-alkynyl; —$(CH_2)_nXR_{12}$; —$(CH_2)_nR_{17}$; —$COXR_{11}$; —$XR_{11}$; —$CO_2R_{11}$; or —$CONR_{11}R_{12}$;

$R_8$ is hydrogen; linear or branched ($C_1$-$C_6$)-alkyl, ($C_2$-$C_6$)-alkenyl, or ($C_2$-$C_6$)-alkynyl; —$(CH_2)_mCO_2R_{11}$; or —$(CH_2)_mCONR_{11}R_{12}$;

$R_{11}$ and $R_{12}$ are each independently hydrogen; linear or branched ($C_1$-$C_6$)-alkyl, ($C_2$-$C_6$)-alkenyl, or ($C_2$-$C_6$)-alkynyl; or $R_{11}$ and $R_{12}$ may together form a three- to seven-membered heterocyclic group containing up to 3 heteroatoms selected from N, O, or S;

$R_{13}$ and $R_{14}$ are each independently hydrogen; linear or branched ($C_1$-$C_6$)-alkyl, ($C_2$-$C_6$)-alkenyl, or ($C_2$-$C_6$)-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$R_{23}CO_2R_{23}$, —$NR_{23}COR_{23}$, —$NR_{23}CON(R_{23})_2$, or —$CON(R_{23})_2$; aryl; or aryl optionally substituted with one to three substituents selected from halogen, $R_{15}$, —$OR_{15}$, or —$NR_{15}R_{16}$; or $R_{13}$ and $R_{14}$ may together form a three- to seven-membered heterocyclic group containing up to 3 heteroatoms selected from N, O, or S, and wherein the heterocyclic group formed by $R_{13}$ and $R_{14}$ is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_{15}$ and $R_{16}$ are each independently hydrogen; or linear or branched ($C_1$-$C_6$)-alkyl, ($C_2$-$C_6$)-alkenyl, or ($C_2$-$C_6$)-alkynyl; or both $R_{15}$ and $R_{16}$ may together form a three- to seven-membered heterocyclic group containing up to 3 heteroatoms selected from N, O, or S;

$R_{17}$ is phenyl, 2-pyridyl, 3-pyridyl, or 4-pyridyl;

$R_{18}$, $R_{19}$, and $R_{20}$ are each independently hydrogen; linear or branched ($C_1$-$C_6$)-alkyl, ($C_2$-$C_6$)-alkenyl, or ($C_2$-$C_6$)-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; halogen; —$NR_{13}R_{14}$; —C(OH)($CF_3$)$_2$; —CH($CF_3$)$_2$; —C($CF_3$)$_3$; —$XR_{13}$; —$COR_{13}$; —$CO_2R_{13}$; or —CON($R_3$)($R_{14}$);

X is —O—, —$NR_{12}$—, or —$SO_m$—;

each m is independently 0, 1, or 2; and each n is independently 0, 1, 2, 3, or 4.

In one embodiment, Ar is phenyl.

In another embodiment, one $R_6$ substituent is attached at the 4 position of phenyl.

In one embodiment, $R_1$ and $R_2$ are each independently hydrogen; linear or branched ($C_1$-$C_6$)-alkyl; or $R_1$ and $R_2$ may together form a three- to seven-membered cycloalkyl group.

In another embodiment, $R_1$ and $R_2$ are hydrogen.

In one embodiment, $R_1$ is linear or branched ($C_1$-$C_6$)-alkyl and $R_2$ is hydrogen.

In one embodiment, $R_1$ is methyl and $R_2$ is hydrogen.

In one embodiment, when $R_1$ and $R_2$ are different, the compound or pharmaceutically acceptable salt of the compound is the S-enantiomer with respect to the carbon to which $R_1$ and $R_2$ are bound.

In another embodiment, when $R_1$ and $R_2$ are different, the compound or pharmaceutically acceptable salt of the compound is the R-enantiomer with respect to the carbon to which $R_1$ and $R_2$ are bound.

In one embodiment, $R_4$ and $R_5$ are each independently hydrogen, or linear or branched ($C_1$-$C_6$)-alkyl.

In one embodiment, $R_4$ and $R_5$ are hydrogen.

In another embodiment, $R_4$ is linear or branched ($C_1$-$C_6$)-alkyl and $R_5$ is hydrogen.

In one embodiment, $R_4$ is methyl or ethyl and $R_5$ is hydrogen.

In another embodiment, when $R_4$ is other than hydrogen, the compound or pharmaceutically acceptable salt of the compound is the S-enantiomer with respect to the carbon to which $R_4$ is bound.

In one embodiment, when $R_1$ and $R_2$ are different, the compound or pharmaceutically acceptable salt of the compound is the S-enantiomer with respect to the carbon to which $R_1$ and $R_2$ are bound, and when $R_4$ is other than hydrogen, the compound or pharmaceutically acceptable salt of the compound is the S-enantiomer with respect to the carbon to which $R_4$ is bound.

In another embodiment, when $R_1$ and $R_2$ are different, the compound or pharmaceutically acceptable salt of the compound is the R-enantiomer with respect to the carbon to which $R_1$ and $R_2$ are bound, and when $R_4$ is other than hydrogen, the compound or pharmaceutically acceptable salt of the compound is the S-enantiomer with respect to the carbon to which $R_4$ is bound.

In one embodiment, $R_6$ is hydrogen, linear or branched ($C_1$-$C_6$)-alkyl, —N($R_{23}$)$_2$, or —N$R_{13}R_{14}$; $R_{23}$ is linear or branched ($C_1$-$C_6$)-alkyl; and $R_{13}$ and $R_{14}$ are each independently linear or branched ($C_1$-$C_6$)-alkyl, each optionally substituted with —O$R_{23}$, —S$R_{23}$, or —N($R_{23}$)$_2$; or $R_{13}$ and $R_{14}$ may be taken together to form a three- to seven-membered heterocyclic group containing one or two heteroatoms selected from N or O, and optionally substituted with O$R_{23}$, —S$R_{23}$, —N($R_{23}$)$_2$, or —(CH$_2$)$_n$O$R_{23}$.

In one embodiment, $R_6$ is ethyl, t-butyl, —N(CH$_2$CH$_3$)$_2$, pyrrolidine, 2-hydroxymethylpyrrolidine, or isopropyl.

In one embodiment, $R_3$ is

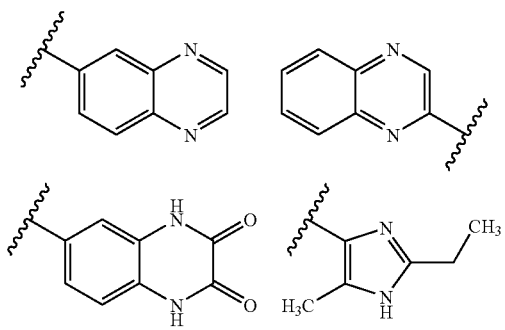

-continued

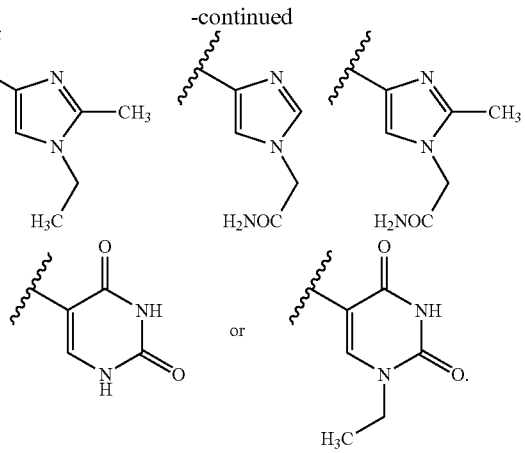

In another embodiment, $R_3$ is

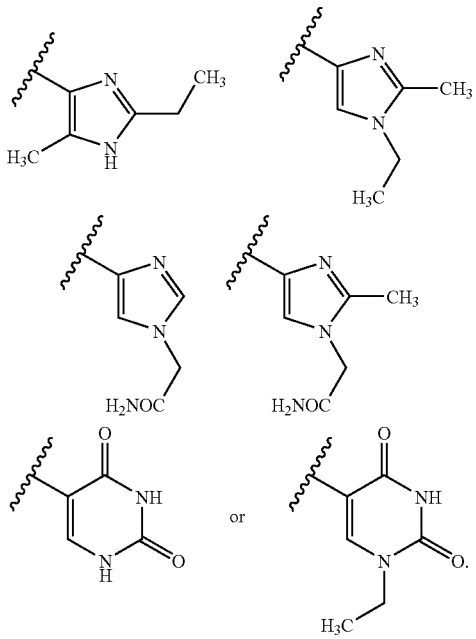

In one embodiment, $R_{18}$, $R_{19}$, $R_{20}$, $R_{21}$, $R_{22}$, $R_{24}$, $R_{25}$, $R_{26}$, and $R_{27}$ are each independently hydrogen, or linear or branched ($C_1$-$C_6$)-alkyl.

In another embodiment, $R_{18}$, $R_{19}$, $R_{20}$, $R_{21}$, $R_{22}$, $R_{24}$, $R_{25}$, $R_{26}$, and $R_{27}$ are each hydrogen.

In one embodiment, $R_{18}$, $R_{19}$, $R_{20}$, $R_{21}$, $R_{22}$, $R_{24}$, $R_{25}$, $R_{26}$, and $R_{27}$ are each hydrogen; $R_1$, $R_2$, $R_4$, and $R_5$ are each independently hydrogen, or linear or branched ($C_1$-$C_6$)-alkyl; Ar is phenyl; $R_6$ is attached at the 4-position of phenyl; $R_6$ is linear or branched ($C_1$-$C_6$)-alkyl, —N($R_{23}$)$_2$, or —N$R_{13}R_{14}$; $R_{23}$ is linear or branched ($C_1$-$C_6$)-alkyl; $R_{13}$ and $R_{14}$ are each independently linear or branched ($C_1$-$C_6$)-alkyl, each optionally substituted with —O$R_{23}$, —S$R_{23}$, or —N($R_{23}$)$_2$; or $R_{13}$ and $R_{14}$ may be taken together to form a three- to seven-membered heterocyclic group containing one or two heteroatoms selected from N or O, and optionally substituted with —O$R_{23}$, —S$R_{23}$, —N($R_{23}$)$_2$, or —(CH$_2$)$_n$O$R_{23}$; and $R_3$ is

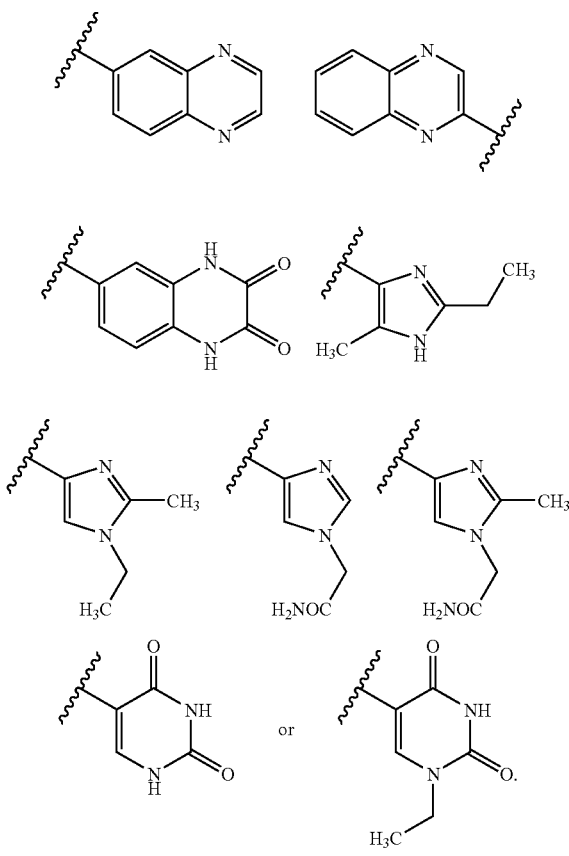

In one embodiment, $R_2$, $R_5$, $R_{18}$, $R_{19}$, $R_{20}$, $R_{21}$, $R_{22}$, $R_{24}$, $R_{25}$, $R_{26}$, and $R_{27}$ are each hydrogen; $R_1$ and $R_4$ are each independently hydrogen, methyl, or ethyl; Ar is phenyl; $R_6$ is attached at the 4-position of phenyl; $R_6$ is ethyl, t-butyl, —N(CH$_2$CH$_3$)$_2$, pyrrolidine, 2-hydroxymethylpyrrolidine, or isopropyl; and $R_3$ is

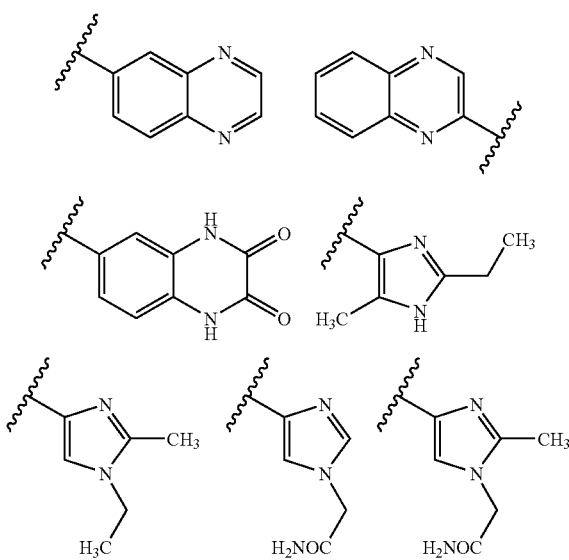

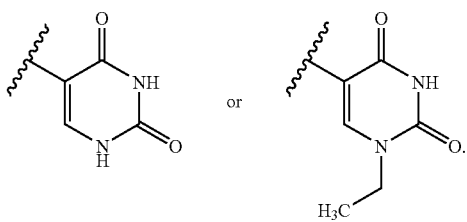

Compounds of the Formula (IA)

In one embodiment, the invention is directed to compounds of the Formula (IA):

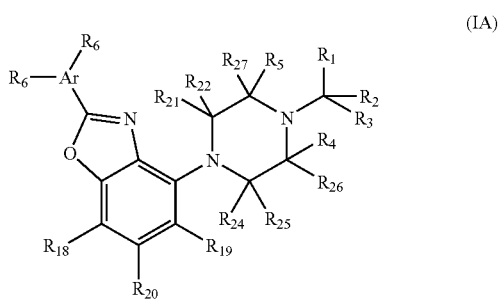

(IA)

and pharmaceutically acceptable salts thereof, wherein

Ar is phenyl, 2-thiophenyl or 3-thiophenyl;

$R_1$ and $R_2$ are each independently hydrogen; or linear or branched ($C_1$-$C_6$)-alkyl, ($C_2$-$C_6$)-alkenyl, or ($C_2$-$C_6$)-alkynyl, each optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, or —CON(R$_{23}$)$_2$; or $R_1$ and $R_2$ may together form a three- to seven-membered cycloalkyl group, wherein the cycloalkyl group formed by $R_1$ and $R_2$ is optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —(CH$_2$)$_n$OR$_{23}$;

$R_3$ is one of the following:

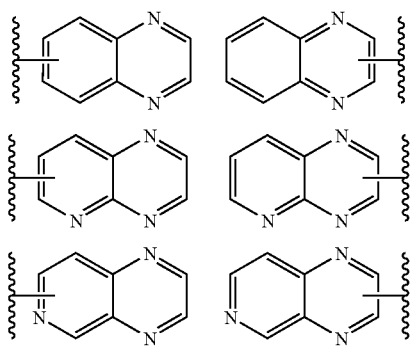

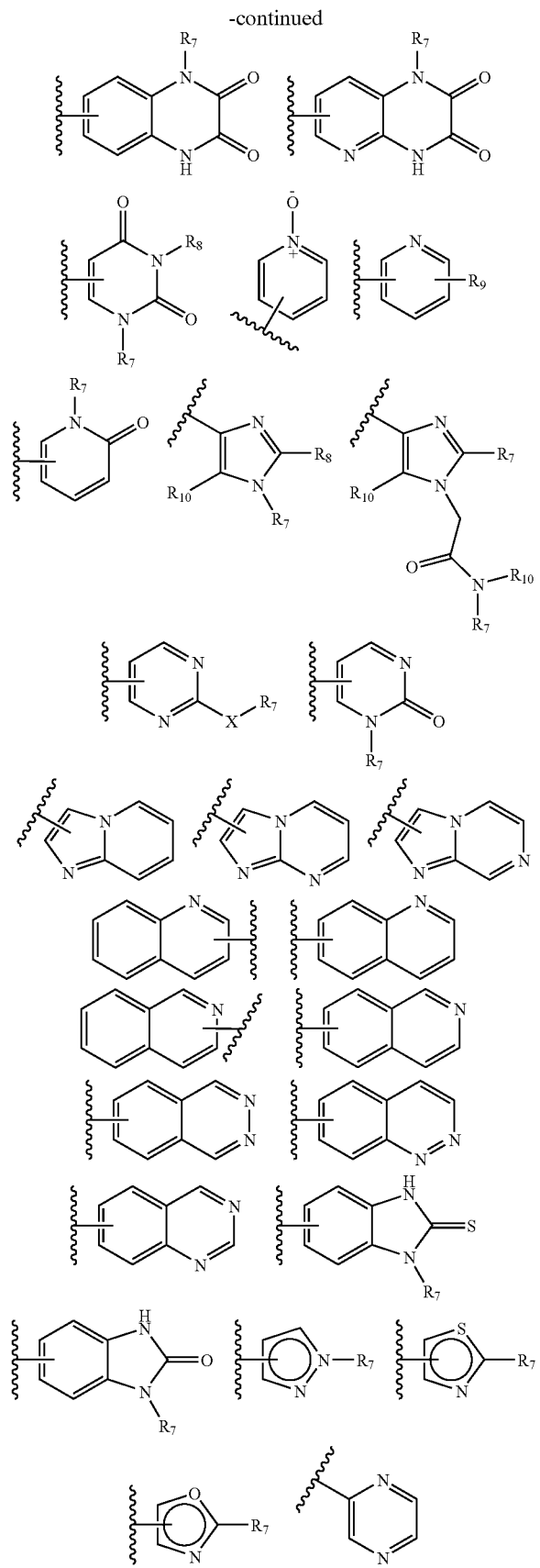

each $R_3$ also having up to three $R_{10}$ substituents attached to the ring of $R_3$ containing at least one N;

$R_4$, $R_5$, $R_{10}$, $R_{21}$, $R_{22}$, $R_{23}$, $R_{24}$, $R_{25}$, $R_{26}$, and $R_{27}$ are each independently hydrogen; or linear or branched $(C_1\text{-}C_6)$-alkyl, $(C_2\text{-}C_6)$-alkenyl, or $(C_2\text{-}C_6)$-alkynyl;

each $R_6$ is independently hydrogen; linear or branched $(C_1\text{-}C_6)$-alkyl, $(C_2\text{-}C_6)$-alkenyl, or $(C_2\text{-}C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, or $-CON(R_{23})_2$; $-NR_{13}R_{14}$; $-C(OH)(CF_3)_2$; $-CH(CF_3)_2$; $-C(CF_3)_3$; $-XR_{13}$; or $-COR_{13}$; and when two $R_6$ are ortho to each other, they may together form a five- to seven-membered cyclic group containing up to 3 heteroatoms selected from N, O, or S, and wherein the cyclic group formed by the ortho $R_6$ groups is optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, $-CON(R_{23})_2$, or $-(CH_2)_nOR_{23}$;

$R_7$ and $R_9$ are each independently hydrogen; linear or branched $(C_1\text{-}C_6)$-alkyl, $(C_2\text{-}C_6)$-alkenyl, or $(C_2\text{-}C_6)$-alkynyl; $-(CH_2)_nXR_{12}$; $-(CH_2)_nR_{17}$; $-COXR_{11}$; $-XR_{11}-CO_2R_1$; or $-CONR_{11}R_{12}$;

$R_8$ is hydrogen; linear or branched $(C_1\text{-}C_6)$-alkyl, $(C_2\text{-}C_6)$-alkenyl, or $(C_2\text{-}C_6)$-alkynyl; $-(CH_2)_mCO_2R_{11}$; or $-(CH_2)_mCONR_{11}R_{12}$;

$R_{11}$ and $R_{12}$ are each independently hydrogen; linear or branched $(C_1\text{-}C_6)$-alkyl, $(C_2\text{-}C_6)$-alkenyl, or $(C_2\text{-}C_6)$-alkynyl; or $R_{11}$ and $R_{12}$ may together form a three- to seven-membered heterocyclic group containing up to 3 heteroatoms selected from N, O, or S;

$R_{13}$ and $R_{14}$ are each independently hydrogen; linear or branched $(C_1\text{-}C_6)$-alkyl, $(C_2\text{-}C_6)$-alkenyl, or $(C_2\text{-}C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-R_{23}CO_2R_{23}$, $-NR_{23}COR_{23}$, $-NR_{23}CON(R_{23})_2$, or $-CON(R_{23})_2$; aryl; or aryl optionally substituted with one to three substituents selected from halogen, $R_{15}$, $-OR_{15}$, or $-NR_{15}R_6$; or $R_{13}$ and $R_{14}$ may together form a three- to seven-membered heterocyclic group containing up to 3 heteroatoms selected from N, O, or S, and wherein the heterocyclic group formed by $R_{13}$ and $R_{14}$ is optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, $-CON(R_{23})_2$, or $-(CH_2)_nOR_{23}$;

$R_{15}$ and $R_{16}$ are each independently hydrogen; or linear or branched $(C_1\text{-}C_6)$-alkyl, $(C_2\text{-}C_6)$-alkenyl, or $(C_2\text{-}C_6)$-alkynyl; or both $R_{15}$ and $R_{16}$ may together form a three- to seven-membered heterocyclic group containing up to 3 heteroatoms selected from N, O, or S;

$R_{17}$ is phenyl, 2-pyridyl, 3-pyridyl, or 4-pyridyl;

$R_{18}$, $R_{19}$, and $R_{20}$ are each independently hydrogen; linear or branched $(C_1\text{-}C_6)$-alkyl, $(C_2\text{-}C_6)$-alkenyl, or $(C_2\text{-}C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, or $-CON(R_{23})_2$; halogen; $-NR_{13}R_{14}$; $-C(OH)(CF_3)_2$; $-CH(CF_3)_2$; $-C(CF_3)_3$; $-XR_{13}$; $-COR_{13}$; $-CO_2R_{13}$; or $-CON(R_{13})(R_{14})$;

X is $-O-$, $-NR_{12}-$, or $-SO_m-$;

each m is independently 0, 1, or 2; and each n is independently 0, 1, 2, 3, or 4.

In one embodiment, Ar is phenyl.

In another embodiment, one $R_6$ substituent is attached at the 4 position of phenyl.

In one embodiment, $R_1$ and $R_2$ are each independently hydrogen; linear or branched $(C_1-C_6)$-alkyl; or $R_1$ and $R_2$ may together form a three- to seven-membered cycloalkyl group.

In another embodiment, $R_1$ and $R_2$ are hydrogen.

In one embodiment, $R_1$ is linear or branched $(C_1-C_6)$-alkyl and $R_2$ is hydrogen.

In one embodiment, $R_1$ is methyl and $R_2$ is hydrogen.

In one embodiment, when $R_1$ and $R_2$ are different, the compound or pharmaceutically acceptable salt of the compound is the S-enantiomer with respect to the carbon to which $R_1$ and $R_2$ are bound.

In another embodiment, when $R_1$ and $R_2$ are different, the compound or pharmaceutically acceptable salt of the compound is the R-enantiomer with respect to the carbon to which $R_1$ and $R_2$ are bound.

In one embodiment, $R_4$ and $R_5$ are each independently hydrogen, or linear or branched $(C_1-C_6)$-alkyl.

In one embodiment, $R_4$ and $R_5$ are hydrogen.

In another embodiment, $R_4$ is linear or branched $(C_1-C_6)$-alkyl and $R_5$ is hydrogen.

In one embodiment, $R_4$ is methyl or ethyl and $R_5$ is hydrogen.

In another embodiment, when $R_4$ is other than hydrogen, the compound or pharmaceutically acceptable salt of the compound is the S-enantiomer with respect to the carbon to which $R_4$ is bound.

In one embodiment, when $R_1$ and $R_2$ are different, the compound or pharmaceutically acceptable salt of the compound is the S-enantiomer with respect to the carbon to which $R_1$ and $R_2$ are bound, and when $R_4$ is other than hydrogen, the compound or pharmaceutically acceptable salt of the compound is the S-enantiomer with respect to the carbon to which $R_4$ is bound.

In another embodiment, when $R_1$ and $R_2$ are different, the compound or pharmaceutically acceptable salt of the compound is the R-enantiomer with respect to the carbon to which $R_1$ and $R_2$ are bound, and when $R_4$ is other than hydrogen, the compound or pharmaceutically acceptable salt of the compound is the S-enantiomer with respect to the carbon to which $R_4$ is bound.

In one embodiment, $R_6$ is hydrogen, linear or branched $(C_1-C_6)$-alkyl, $-N(R_{23})_2$, or $-NR_{13}R_{14}$; $R_{23}$ is linear or branched $(C_1-C_6)$-alkyl; and $R_{13}$ and $R_{14}$ are each independently linear or branched $(C_1-C_6)$-alkyl, each optionally substituted with $-OR_{23}$, $-SR_{23}$, or $-N(R_{23})_2$; or $R_{13}$ and $R_{14}$ may be taken together to form a three- to seven-membered heterocyclic group containing one or two heteroatoms selected from N or O, and optionally substituted with $-OR_{23}$, $-SR_{23}$, $-N(R_{23})_2$, or $-(CH_2)_nOR_{23}$.

In one embodiment, $R_6$ is ethyl, t-butyl, $-N(CH_2CH_3)_2$, pyrrolidine, 2-hydroxymethylpyrrolidine, or isopropyl.

In one embodiment, $R_3$ is

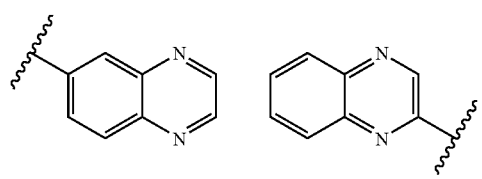

-continued

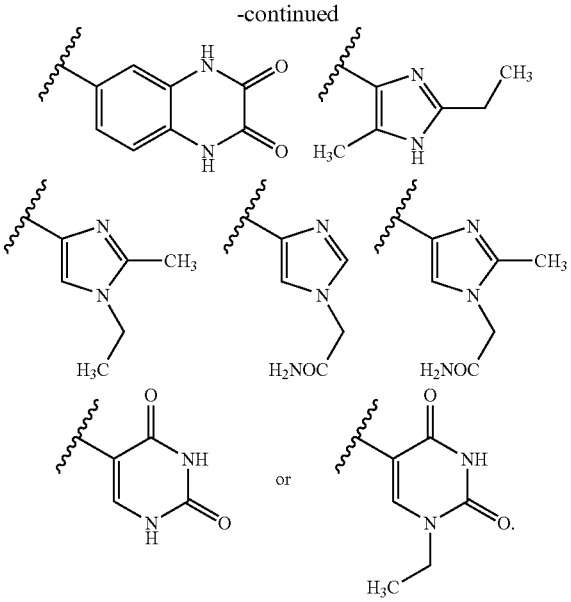

In another embodiment, $R_3$ is

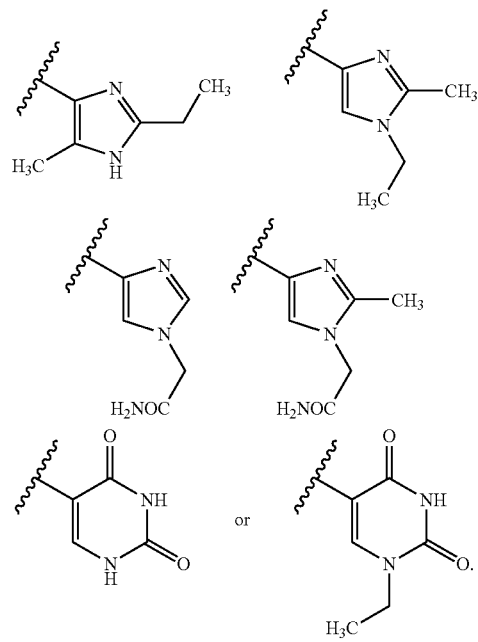

In one embodiment, $R_{18}$, $R_{19}$, $R_{20}$, $R_{21}$, $R_{22}$, $R_{24}$, $R_{25}$, $R_{26}$, and $R_{27}$ are each independently hydrogen, or linear or branched $(C_1-C_6)$-alkyl.

In another embodiment, $R_{18}$, $R_{19}$, $R_{20}$, $R_{21}$, $R_{22}$, $R_{24}$, $R_{25}$, $R_{26}$, and $R_{27}$ are each hydrogen.

In one embodiment, $R_{18}$, $R_{19}$, $R_{20}$, $R_{21}$, $R_{22}$, $R_{24}$, $R_{25}$, $R_{26}$, and $R_{27}$ are each hydrogen; $R_1$, $R_2$, $R_4$, and $R_5$ are each independently hydrogen, or linear or branched $(C_1-C_6)$-alkyl; Ar is phenyl; $R_6$ is attached at the 4-position of phenyl; $R_6$ is linear or branched $(C_1-C_6)$-alkyl, $-N(R_{23})_2$, or $-NR_{13}R_{14}$; $R_{23}$ is linear or branched $(C_1-C_6)$-alkyl; $R_{13}$ and $R_{14}$ are each independently linear or branched $(C_1-C_6)$-alkyl, each optionally substituted with $-OR_{23}$, $-SR_{23}$, or $-N(R_{23})_2$; or $R_{13}$ and $R_{14}$ may be taken together to form a three- to seven-membered heterocyclic group containing one or two heteroatoms selected from N or O, and optionally substituted with —$OR_{23}$, —$SR_{23}$, —$N(R_{23})_2$, or —$(CH_2)_nOR_{23}$; and $R_3$ is

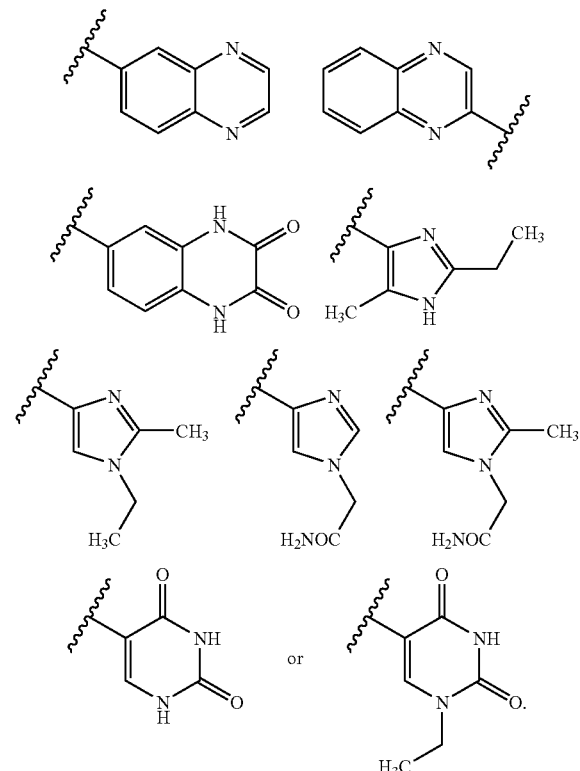

In one embodiment, $R_2$, $R_5$, $R_{18}$, $R_{19}$, $R_{20}$, $R_{21}$, $R_{22}$, $R_{24}$, $R_{25}$, $R_{26}$, and $R_{27}$ are each hydrogen; $R_1$ and $R_4$ are each independently hydrogen, methyl, or ethyl; Ar is phenyl; $R_6$ is attached at the 4-position of phenyl; $R_6$ is ethyl, t-butyl, —$N(CH_2CH_3)_2$, pyrrolidine, 2-hydroxymethylpyrrolidine, or isopropyl; and $R_3$ is

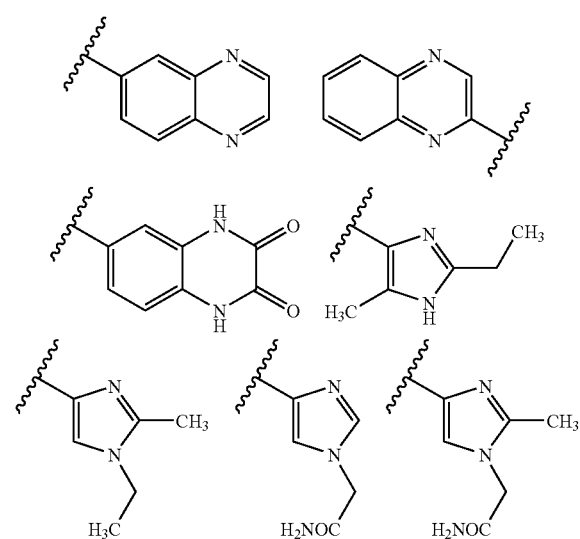

-continued

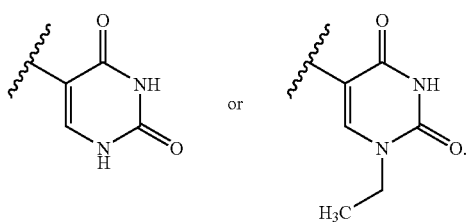

Compounds of the Formula (IB)

In one embodiment, the invention is directed to compounds of the Formula (IB):

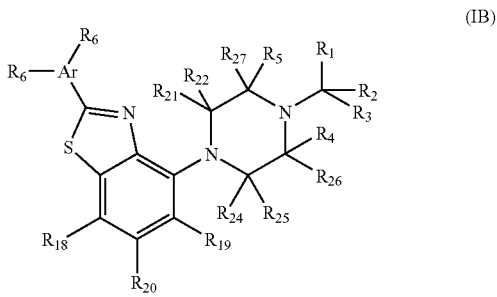

(IB)

and pharmaceutically acceptable salts thereof,
wherein
Ar is phenyl, 2-thiophenyl or 3-thiophenyl;
$R_1$ and $R_2$ are each independently hydrogen; or linear or branched ($C_1$-$C_6$)-alkyl, ($C_2$-$C_6$)-alkenyl, or ($C_2$-$C_6$)-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; or $R_1$ and $R_2$ may together form a three- to seven-membered cycloalkyl group, wherein the cycloalkyl group formed by $R_1$ and $R_2$ is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;
$R_3$ is one of the following:

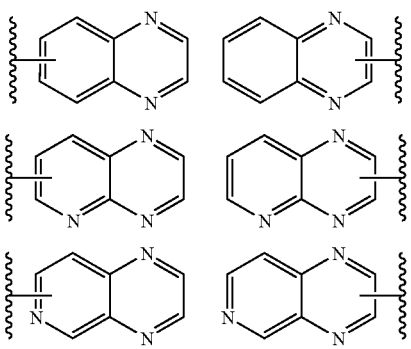

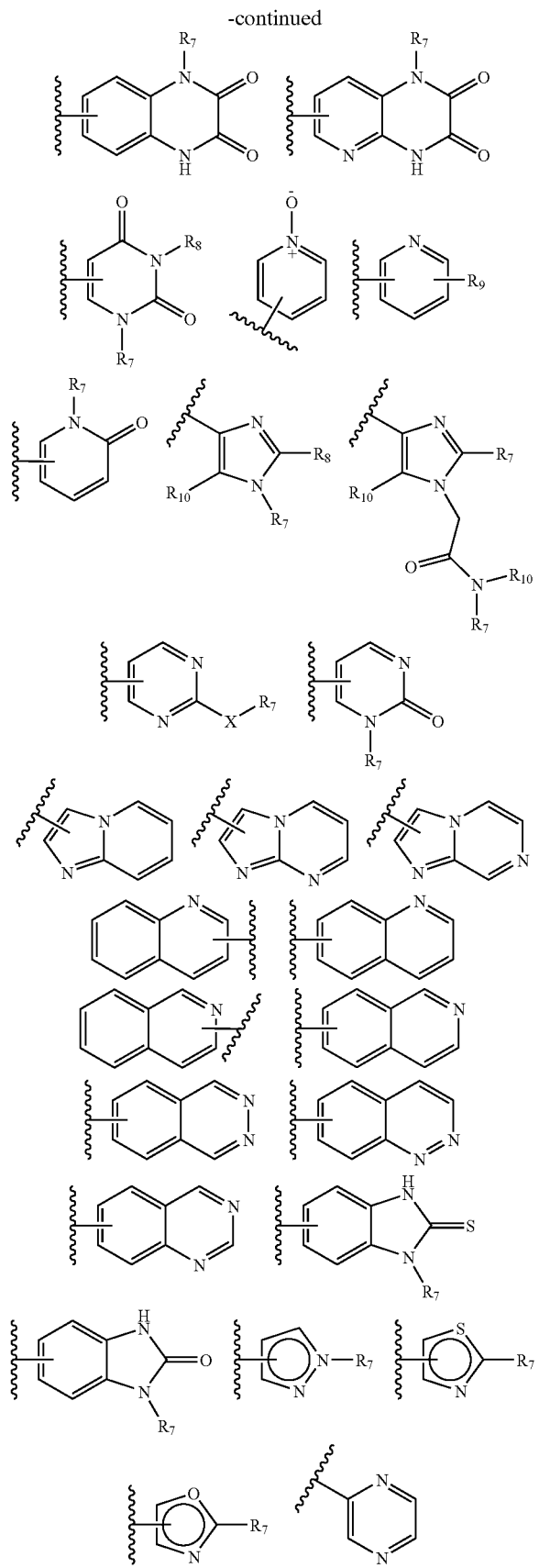

each $R_3$ also having up to three $R_{10}$ substituents attached to the ring of $R_3$ containing at least one N;

$R_4$, $R_5$, $R_{10}$, $R_{21}$, $R_{22}$, $R_{23}$, $R_{24}$, $R_{25}$, $R_{26}$, and $R_{27}$ are each independently hydrogen; or linear or branched ($C_1$-$C_6$)-alkyl, ($C_2$-$C_6$)-alkenyl, or ($C_2$-$C_6$)-alkynyl;

each $R_6$ is independently hydrogen; linear or branched ($C_1$-$C_6$)-alkyl, ($C_2$-$C_6$)-alkenyl, or ($C_2$-$C_6$)-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; —$NR_{13}R_{14}$; —C(OH)(CF$_3$)$_2$; —CH(CF$_3$)$_2$; —C(CF$_3$)$_3$; —$XR_{13}$; or —$COR_{13}$; and when two $R_6$ are ortho to each other, they may together form a five- to seven-membered cyclic group containing up to 3 heteroatoms selected from N, O, or S, and wherein the cyclic group formed by the ortho $R_6$ groups is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_7$ and $R_9$ are each independently hydrogen; linear or branched ($C_1$-$C_6$)-alkyl, ($C_2$-$C_6$)-alkenyl, or ($C_2$-$C_6$)-alkynyl; —$(CH_2)_nXR_{12}$; —$(CH_2)_nR_{17}$; —$COXR_{11}$; —$XR_{11}$; —$CO_2R_{11}$, or —$CONR_{11}R_{12}$;

$R_8$ is hydrogen; linear or branched ($C_1$-$C_6$)-alkyl, ($C_2$-$C_6$)-alkenyl, or ($C_2$-$C_6$)-alkynyl; —$(CH_2)_mCO_2R_{11}$; or —$(CH_2)_mCONR_{11}R_{12}$;

$R_{11}$ and $R_{12}$ are each independently hydrogen; linear or branched ($C_1$-$C_6$)-alkyl, ($C_2$-$C_6$)-alkenyl, or ($C_2$-$C_6$)-alkynyl; or $R_{11}$ and $R_{12}$ may together form a three- to seven-membered heterocyclic group containing up to 3 heteroatoms selected from N, O, or S;

$R_{13}$ and $R_{14}$ are each independently hydrogen; linear or branched ($C_1$-$C_6$)-alkyl, ($C_2$-$C_6$)-alkenyl, or ($C_2$-$C_6$)-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$R_{23}CO_2R_{23}$, —$NR_{23}COR_{23}$, —$NR_{23}CON(R_{23})_2$, or —$CON(R_{23})_2$; aryl; or aryl optionally substituted with one to three substituents selected from halogen, $R_{15}$, —$OR_{15}$, or —$NR_{15}R_{16}$; or $R_{13}$ and $R_{14}$ may together form a three- to seven-membered heterocyclic group containing up to 3 heteroatoms selected from N, O, or S, and wherein the heterocyclic group formed by $R_{13}$ and $R_{14}$ is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_{15}$ and $R_{16}$ are each independently hydrogen; or linear or branched ($C_1$-$C_6$)-alkyl, ($C_2$-$C_6$)-alkenyl, or ($C_2$-$C_6$)-alkynyl; or both $R_{15}$ and $R_{16}$ may together form a three- to seven-membered heterocyclic group containing up to 3 heteroatoms selected from N, O, or S;

$R_{17}$ is phenyl, 2-pyridyl, 3-pyridyl, or 4-pyridyl;

$R_{18}$, $R_{19}$, and $R_{20}$ are each independently hydrogen; linear or branched ($C_1$-$C_6$)-alkyl, ($C_2$-$C_6$)-alkenyl, or ($C_2$-$C_6$)-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; halogen; —$NR_{13}R_{14}$; —C(OH)(CF$_3$)$_2$; —CH(CF$_3$)$_2$; —C(CF$_3$)$_3$; —$XR_{13}$; —$COR_{13}$; —$CO_2R_{13}$; or —$CON(R_{13})(R_{14})$;

X is —O—, —$NR_{12}$—, or —$SO_m$—;

each m is independently 0, 1, or 2; and each n is independently 0, 1, 2, 3, or 4.

In one embodiment, Ar is phenyl.

In another embodiment, one $R_6$ substituent is attached at the 4 position of phenyl.

In one embodiment, $R_1$ and $R_2$ are each independently hydrogen; linear or branched ($C_1$-$C_6$)-alkyl; or $R_1$ and $R_2$ may together form a three- to seven-membered cycloalkyl group.

In another embodiment, $R_1$ and $R_2$ are hydrogen.

In one embodiment, $R_1$ is linear or branched ($C_1$-$C_6$)-alkyl and $R_2$ is hydrogen.

In one embodiment, $R_1$ is methyl and $R_2$ is hydrogen.

In one embodiment, when $R_1$ and $R_2$ are different, the compound or pharmaceutically acceptable salt of the compound is the S-enantiomer with respect to the carbon to which $R_1$ and $R_2$ are bound.

In another embodiment, when $R_1$ and $R_2$ are different, the compound or pharmaceutically acceptable salt of the compound is the R-enantiomer with respect to the carbon to which $R_1$ and $R_2$ are bound.

In one embodiment, $R_4$ and $R_5$ are each independently hydrogen, or linear or branched ($C_1$-$C_6$)-alkyl.

In one embodiment, $R_4$ and $R_5$ are hydrogen.

In another embodiment, $R_4$ is linear or branched ($C_1$-$C_6$)-alkyl and $R_5$ is hydrogen.

In one embodiment, $R_4$ is methyl or ethyl and $R_5$ is hydrogen.

In another embodiment, when $R_4$ is other than hydrogen, the compound or pharmaceutically acceptable salt of the compound is the S-enantiomer with respect to the carbon to which $R_4$ is bound.

In one embodiment, when $R_1$ and $R_2$ are different, the compound or pharmaceutically acceptable salt of the compound is the S-enantiomer with respect to the carbon to which $R_1$ and $R_2$ are bound, and when $R_4$ is other than hydrogen, the compound or pharmaceutically acceptable salt of the compound is the S-enantiomer with respect to the carbon to which $R_4$ is bound.

In another embodiment, when $R_1$ and $R_2$ are different, the compound or pharmaceutically acceptable salt of the compound is the R-enantiomer with respect to the carbon to which $R_1$ and $R_2$ are bound, and when $R_4$ is other than hydrogen, the compound or pharmaceutically acceptable salt of the compound is the S-enantiomer with respect to the carbon to which $R_4$ is bound.

In one embodiment, $R_6$ is hydrogen, linear or branched ($C_1$-$C_6$)-alkyl, —$N(R_{23})_2$, or —$NR_{13}R_{14}$; $R_{23}$ is linear or branched ($C_1$-$C_6$)-alkyl; and $R_{13}$ and $R_{14}$ are each independently linear or branched ($C_1$-$C_6$)-alkyl, each optionally substituted with $OR_{23}$, —$SR_{23}$, or —$N(R_{23})_2$; or $R_{13}$ and $R_{14}$ may be taken together to form a three- to seven-membered heterocyclic group containing one or two heteroatoms selected from N or O, and optionally substituted with —$OR_{23}$, —$SR_{23}$, —$N(R_{23})_2$, or —$(CH_2)_nOR_{23}$.

In one embodiment, $R_6$ is ethyl, t-butyl, —$N(CH_2CH_3)_2$, pyrrolidine, 2-hydroxymethylpyrrolidine, or isopropyl.

In one embodiment, $R_3$ is

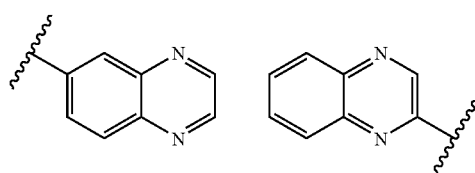

In another embodiment, $R_3$ is

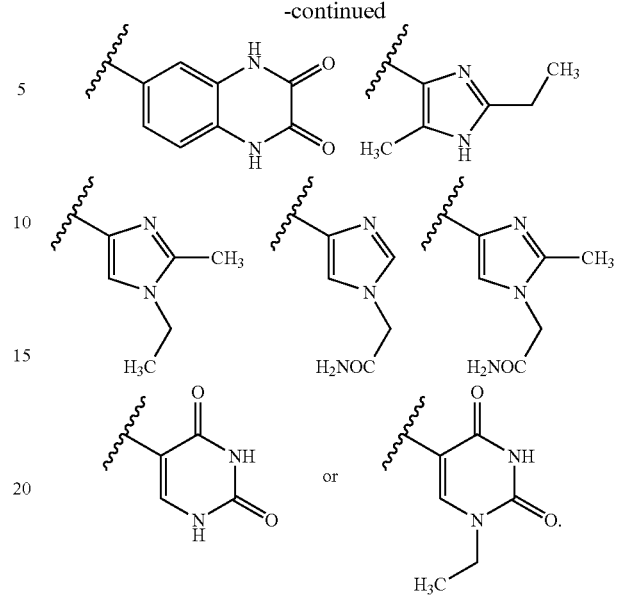

In another embodiment, $R_3$ is

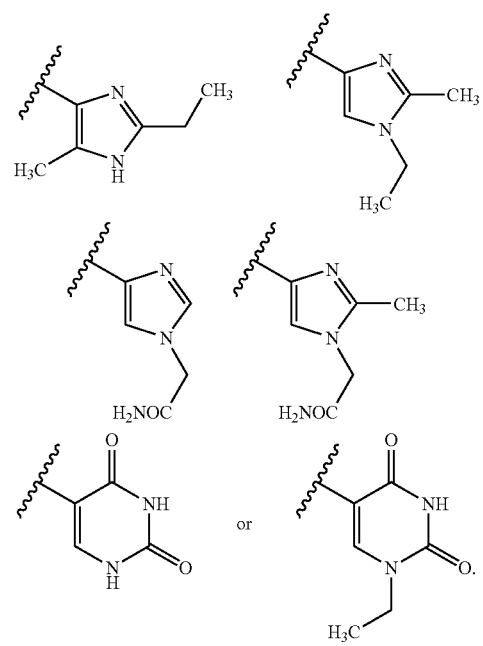

In one embodiment, $R_{18}$, $R_{19}$, $R_{20}$, $R_{21}$, $R_{22}$, $R_{24}$, $R_{25}$, $R_{26}$, and $R_{27}$ are each independently hydrogen, or linear or branched ($C_1$-$C_6$)-alkyl.

In another embodiment, $R_{18}$, $R_{19}$, $R_{20}$, $R_{21}$, $R_{22}$, $R_{24}$, $R_{25}$, $R_{26}$, and $R_{27}$ are each hydrogen.

In one embodiment, $R_{18}$, $R_{19}$, $R_{20}$, $R_{21}$, $R_{22}$, $R_{24}$, $R_{25}$, $R_{26}$, and $R_{27}$ are each hydrogen; $R_1$, $R_2$, $R_4$, and $R_5$ are each independently hydrogen, or linear or branched ($C_1$-$C_6$)-alkyl; Ar is phenyl; $R_6$ is attached at the 4-position of phenyl; $R_6$ is linear or branched ($C_1$-$C_6$)-alkyl, —$N(R_{23})_2$, or —$NR_{13}R_{14}$; $R_{23}$ is linear or branched ($C_1$-$C_6$)-alkyl; $R_{13}$ and $R_{14}$ are each independently linear or branched ($C_1$-$C_6$)-alkyl, each optionally substituted with —$OR_{23}$, —$SR_{23}$, or —$N(R_{23})_2$; or $R_{13}$ and $R_{14}$ may be taken together to form a three- to seven-membered heterocyclic group containing one or two heteroatoms selected from N or O, and optionally substituted with —$OR_{23}$, —$SR_{23}$, —$N(R_{23})_2$, or —$(CH_2)_nOR_{23}$; and $R_3$ is

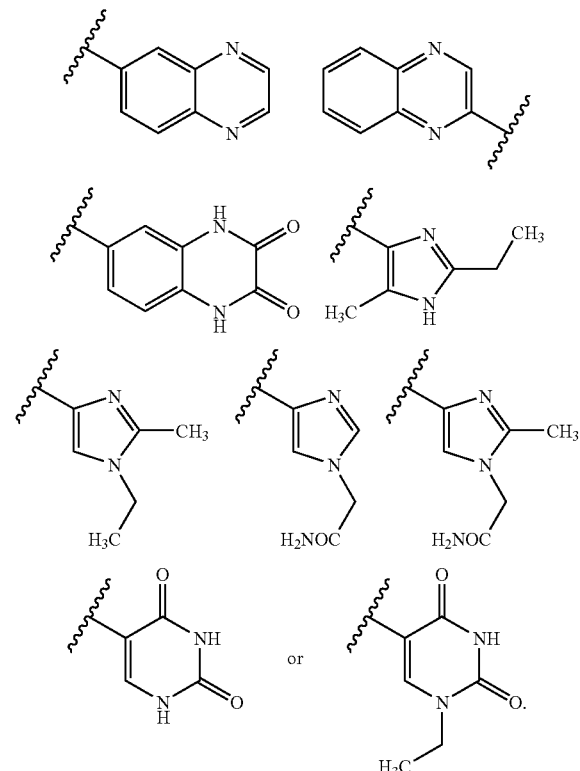

In one embodiment, $R_2$, $R_5$, $R_{18}$, $R_{19}$, $R_{20}$, $R_{21}$, $R_{22}$, $R_{24}$, $R_{25}$, $R_{26}$, and $R_{27}$ are each hydrogen; $R_1$ and $R_4$ are each independently hydrogen, methyl, or ethyl; Ar is phenyl; $R_6$ is attached at the 4-position of phenyl; $R_6$ is ethyl, t-butyl, —$N(CH_2CH_3)_2$, pyrrolidine, 2-hydroxymethylpyrrolidine, or isopropyl; and $R_3$ is

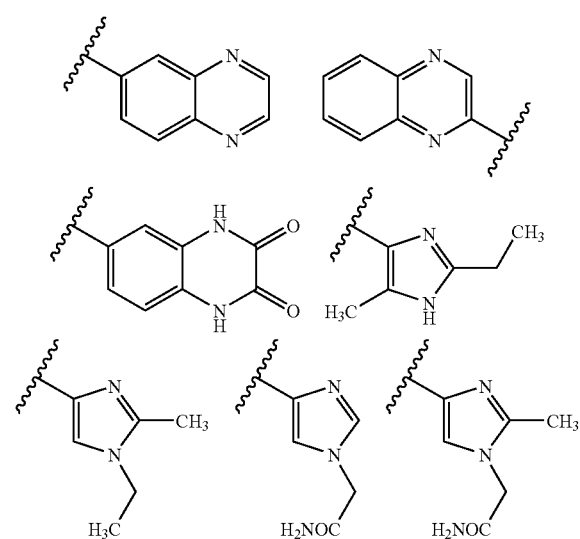

-continued

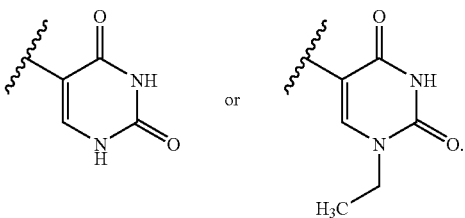

Compounds of the Formula (IC)

In one embodiment, the invention is directed to compounds of the Formula (IC):

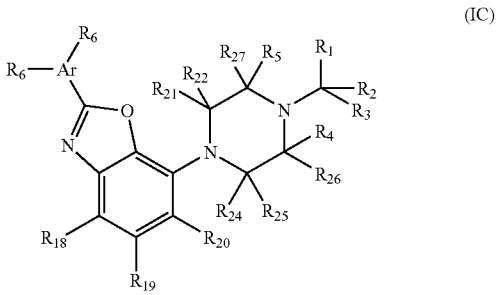

(IC)

and pharmaceutically acceptable salts thereof,
wherein
Ar is phenyl, 2-thiophenyl or 3-thiophenyl;
$R_1$ and $R_2$ are each independently hydrogen; or linear or branched $(C_1-C_6)$-alkyl, $(C_2-C_6)$-alkenyl, or $(C_2-C_6)$-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; or $R_1$ and $R_2$ may together form a three- to seven-membered cycloalkyl group, wherein the cycloalkyl group formed by $R_1$ and $R_2$ is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)OR_{23}$;
$R_3$ is one of the following:

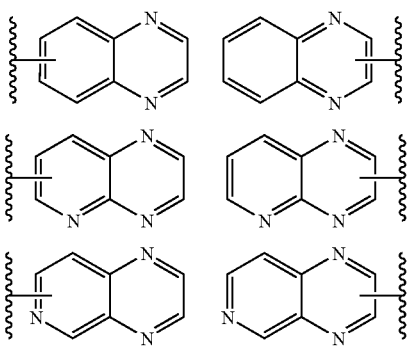

each $R_3$ also having up to three $R_{10}$ substituents attached to the ring of $R_3$ containing at least one N;

$R_4$, $R_5$, $R_{10}$, $R_{21}$, $R_{22}$, $R_{23}$, $R_{24}$, $R_{25}$, $R_{26}$, and $R_{27}$ are each independently hydrogen; or linear or branched $(C_1-C_6)$-alkyl, $(C_2-C_6)$-alkenyl, or $(C_2-C_6)$-alkynyl;

each $R_6$ is independently hydrogen; linear or branched $(C_1-C_6)$-alkyl, $(C_2-C_6)$-alkenyl, or $(C_2-C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, or $-CON(R_{23})_2$; $-NR_{13}R_{14}$; $-C(OH)(CF_3)_2$; $-CH(CF_3)_2$; $-C(CF_3)_3$; $-XR_{13}$; or $-COR_{13}$; and when two $R_6$ are ortho to each other, they may together form a five- to seven-membered cyclic group containing up to 3 heteroatoms selected from N, O, or S, and wherein the cyclic group formed by the ortho $R_6$ groups is optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, $-CON(R_{23})_2$, or $-(CH_2)_nOR_{23}$;

$R_7$ and $R_9$ are each independently hydrogen; linear or branched $(C_1-C_6)$-alkyl, $(C_2-C_6)$-alkenyl, or $(C_2-C_6)$-alkynyl; $-(CH_2)_nXR_{12}$; $-(CH_2)_nR_{17}$; $-COXR_{11}$; $-XR_{11}$; $-CO_2R_{11}$; or $-CONR_{11}R_{12}$;

$R_8$ is hydrogen; linear or branched $(C_1-C_6)$-alkyl, $(C_2-C_6)$-alkenyl, or $(C_2-C_6)$-alkynyl; $-(CH_2)_nCO_2R_{11}$; or $-(CH_2)_mCONR_{11}R_{12}$;

$R_{11}$ and $R_{12}$ are each independently hydrogen; linear or branched $(C_1-C_6)$-alkyl, $(C_2-C_6)$-alkenyl, or $(C_2-C_6)$-alkynyl; or $R_{11}$ and $R_{12}$ may together form a three- to seven-membered heterocyclic group containing up to 3 heteroatoms selected from N, O, or S;

$R_{13}$ and $R_{14}$ are each independently hydrogen; linear or branched $(C_1-C_6)$-alkyl, $(C_2-C_6)$-alkenyl, or $(C_2-C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-R_{23}CO_2R_{23}$, $-NR_{23}COR_{23}$, $-NR_{23}CON(R_{23})_2$, or $-CON(R_{23})_2$; aryl; or aryl optionally substituted with one to three substituents selected from halogen, $R_{15}$, $-OR_{15}$, or $-NR_{15}R_{16}$; or $R_{13}$ and $R_{14}$ may together form a three- to seven-membered heterocyclic group containing up to 3 heteroatoms selected from N, O, or S, and wherein the heterocyclic group formed by $R_{13}$ and $R_{14}$ is optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, $-CON(R_{23})_2$, or $-(CH_2)_nOR_{23}$;

$R_{15}$ and $R_{16}$ are each independently hydrogen; or linear or branched $(C_1-C_6)$-alkyl, $(C_2-C_6)$-alkenyl, or $(C_2-C_6)$-alkynyl; or both $R_{15}$ and $R_{16}$ may together form a three- to seven-membered heterocyclic group containing up to 3 heteroatoms selected from N, O, or S;

$R_{17}$ is phenyl, 2-pyridyl, 3-pyridyl, or 4-pyridyl;

$R_{18}$, $R_{19}$, and $R_{20}$ are each independently hydrogen; linear or branched $(C_1-C_6)$-alkyl, $(C_2-C_6)$-alkenyl, or $(C_2-C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, or $-CON(R_{23})_2$; halogen; $-NR_{13}R_{14}$; $-C(OH)(CF_3)_2$; $-CH(CF_3)_2$; $-C(CF_3)_3$; $-XR_{13}$; $-COR_{13}$; $-CO_2R_{13}$; or $-CON(R_{13})(R_{14})$;

X is $-O-$, $-NR_{12}-$, or $-SO_m-$;

each m is independently 0, 1, or 2; and each n is independently 0, 1, 2, 3, or 4.

In one embodiment, Ar is phenyl.

In another embodiment, one $R_6$ substituent is attached at the 4 position of phenyl.

In one embodiment, $R_1$ and $R_2$ are each independently hydrogen; linear or branched ($C_1$-$C_6$)-alkyl; or $R_1$ and $R_2$ may together form a three- to seven-membered cycloalkyl group.

In another embodiment, $R_1$ and $R_2$ are hydrogen.

In one embodiment, $R_1$ is linear or branched ($C_1$-$C_6$)-alkyl and $R_2$ is hydrogen.

In one embodiment, $R_1$ is methyl and $R_2$ is hydrogen.

In one embodiment, when $R_1$ and $R_2$ are different, the compound or pharmaceutically acceptable salt of the compound is the S-enantiomer with respect to the carbon to which $R_1$ and $R_2$ are bound.

In another embodiment, when $R_1$ and $R_2$ are different, the compound or pharmaceutically acceptable salt of the compound is the R-enantiomer with respect to the carbon to which $R_1$ and $R_2$ are bound.

In one embodiment, $R_4$ and $R_5$ are each independently hydrogen, or linear or branched ($C_1$-$C_6$)-alkyl.

In one embodiment, $R_4$ and $R_5$ are hydrogen.

In another embodiment, $R_4$ is linear or branched ($C_1$-$C_6$)-alkyl and $R_5$ is hydrogen.

In one embodiment, $R_4$ is methyl or ethyl and $R_5$ is hydrogen.

In another embodiment, when $R_4$ is other than hydrogen, the compound or pharmaceutically acceptable salt of the compound is the S-enantiomer with respect to the carbon to which $R_4$ is bound.

In one embodiment, when $R_1$ and $R_2$ are different, the compound or pharmaceutically acceptable salt of the compound is the S-enantiomer with respect to the carbon to which $R_1$ and $R_2$ are bound, and when $R_4$ is other than hydrogen, the compound or pharmaceutically acceptable salt of the compound is the S-enantiomer with respect to the carbon to which $R_4$ is bound.

In another embodiment, when $R_1$ and $R_2$ are different, the compound or pharmaceutically acceptable salt of the compound is the R-enantiomer with respect to the carbon to which $R_1$ and $R_2$ are bound, and when $R_4$ is other than hydrogen, the compound or pharmaceutically acceptable salt of the compound is the S-enantiomer with respect to the carbon to which $R_4$ is bound.

In one embodiment, $R_6$ is hydrogen, linear or branched ($C_1$-$C_6$)-alkyl, —$N(R_{23})_2$, or —$NR_{13}R_{14}$; $R_{23}$ is linear or branched ($C_1$-$C_6$)-alkyl; and $R_{13}$ and $R_{14}$ are each independently linear or branched ($C_1$-$C_6$)-alkyl, each optionally substituted with —$OR_{23}$, —$SR_{23}$, or —$N(R_{23})_2$; or $R_{13}$ and $R_{14}$ may be taken together to form a three- to seven-membered heterocyclic group containing one or two heteroatoms selected from N or O, and optionally substituted with —$OR_{23}$, —$SR_{23}$, —$N(R_{23})_2$, or —$(CH_2)_nOR_{23}$.

In one embodiment, $R_6$ is ethyl, t-butyl, —$N(CH_2CH_3)_2$, pyrrolidine, 2-hydroxymethylpyrrolidine, or isopropyl.

In one embodiment, $R_3$ is

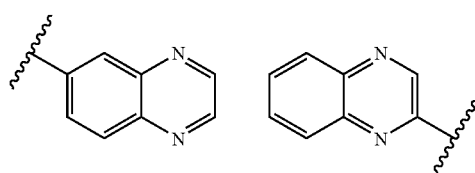

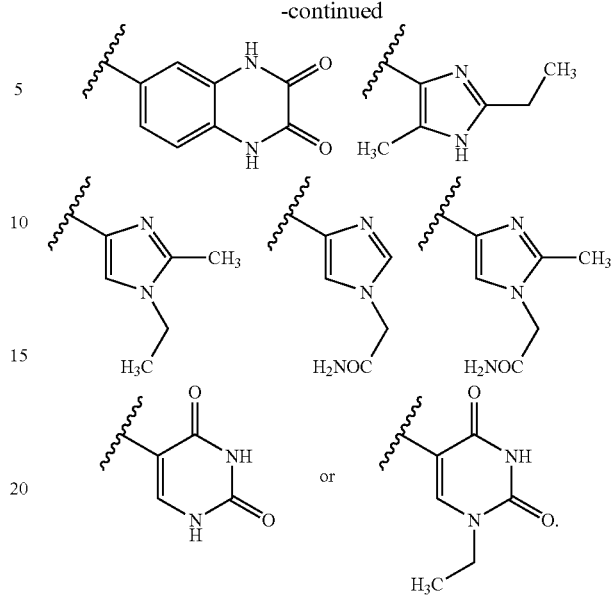

In another embodiment, $R_3$ is

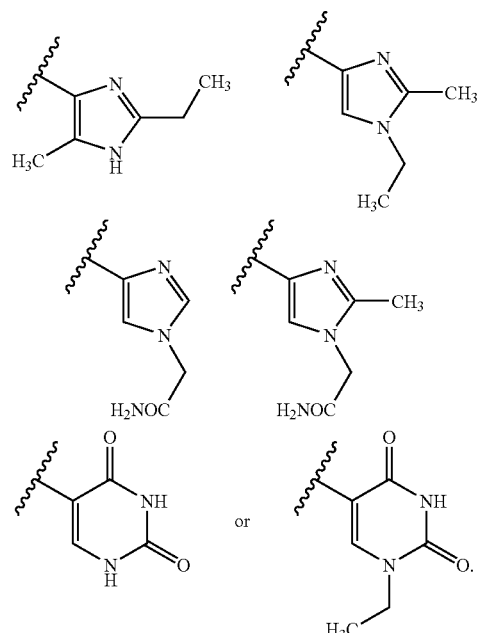

In one embodiment, $R_{18}$, $R_{19}$, $R_{20}$, $R_{21}$, $R_{22}$, $R_{24}$, $R_{25}$, $R_{26}$, and $R_{27}$ are each independently hydrogen, or linear or branched ($C_1$-$C_6$)-alkyl.

In another embodiment, $R_{18}$, $R_{19}$, $R_{20}$, $R_{21}$, $R_{22}$, $R_{24}$, $R_{25}$, $R_{26}$, and $R_{27}$ are each hydrogen.

In one embodiment, $R_{18}$, $R_{19}$, $R_{20}$, $R_{21}$, $R_{22}$, $R_{24}$, $R_{25}$, $R_{26}$, and $R_{27}$ are each hydrogen; $R_1$, $R_2$, $R_4$, and $R_5$ are each independently hydrogen, or linear or branched ($C_1$-$C_6$)-alkyl; Ar is phenyl; $R_6$ is attached at the 4-position of phenyl; $R_6$ is linear or branched ($C_1$-$C_6$)-alkyl, —$N(R_{23})_2$, or —$NR_{13}R_{14}$; $R_{23}$ is linear or branched ($C_1$-$C_6$)-alkyl; $R_{13}$ and $R_{14}$ are each independently linear or branched ($C_1$-$C_6$)-alkyl, each optionally substituted with —$OR_{23}$, —$SR_{23}$, or —$N(R_{23})_2$; or $R_{13}$ and $R_{14}$ may be taken together to form a three- to seven-membered heterocyclic group containing one or two heteroatoms selected from N or O, and optionally substituted with —$OR_{23}$, —$SR_{23}$, —$N(R_{23})_2$, or —$(CH_2)_nOR_{23}$; and $R_3$ is

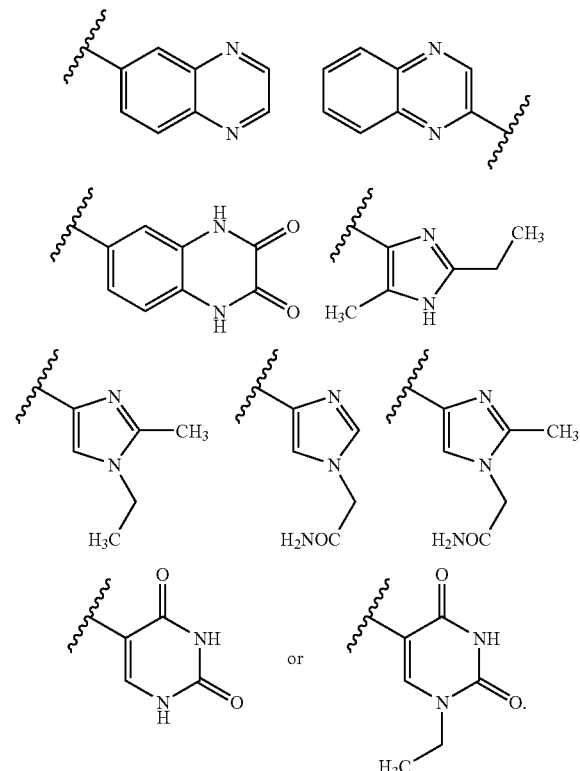

In one embodiment, $R_2$, $R_5$, $R_{18}$, $R_{19}$, $R_{20}$, $R_{21}$, $R_{22}$, $R_{24}$, $R_{25}$, $R_{26}$, and $R_{27}$ are each hydrogen; $R_1$ and $R_4$ are each independently hydrogen, methyl, or ethyl; Ar is phenyl; $R_6$ is attached at the 4-position of phenyl; $R_6$ is ethyl, t-butyl, —$N(CH_2CH_3)_2$, pyrrolidine, 2-hydroxymethylpyrrolidine, or isopropyl; and $R_3$ is

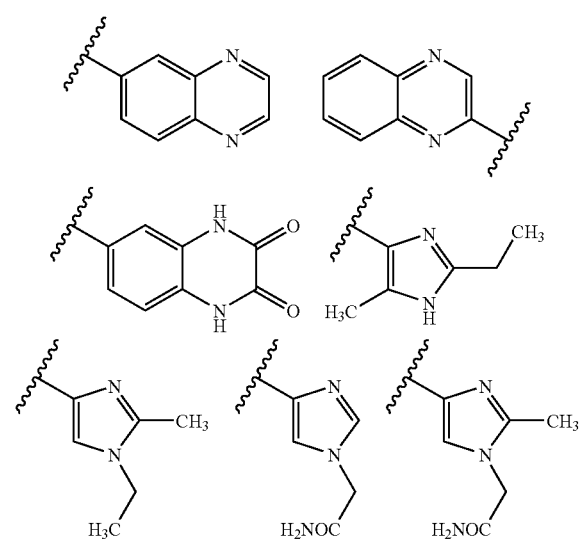

-continued

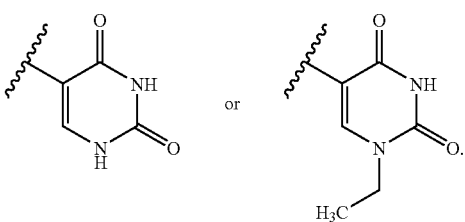

Compounds of the Formula (ID)

In one embodiment, the invention is directed to compounds of the Formula (ID):

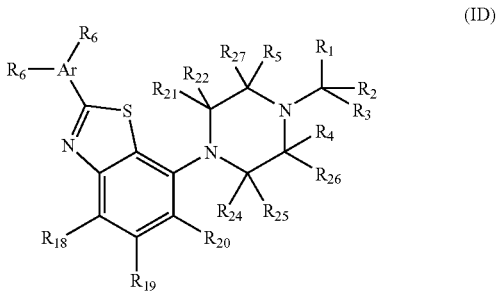

(ID)

and pharmaceutically acceptable salts thereof,
wherein

Ar is phenyl, 2-thiophenyl or 3-thiophenyl;

$R_1$ and $R_2$ are each independently hydrogen; or linear or branched $(C_1-C_6)$-alkyl, $(C_2-C_6)$-alkenyl, or $(C_2-C_6)$-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; or $R_1$ and $R_2$ may together form a three- to seven-membered cycloalkyl group, wherein the cycloalkyl group formed by $R_1$ and $R_2$ is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_3$ is one of the following:

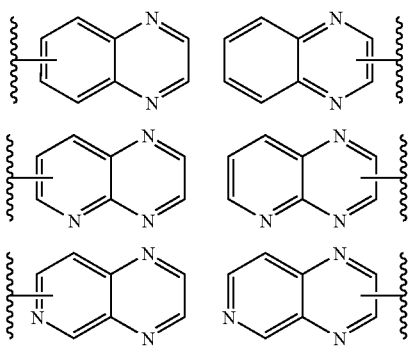

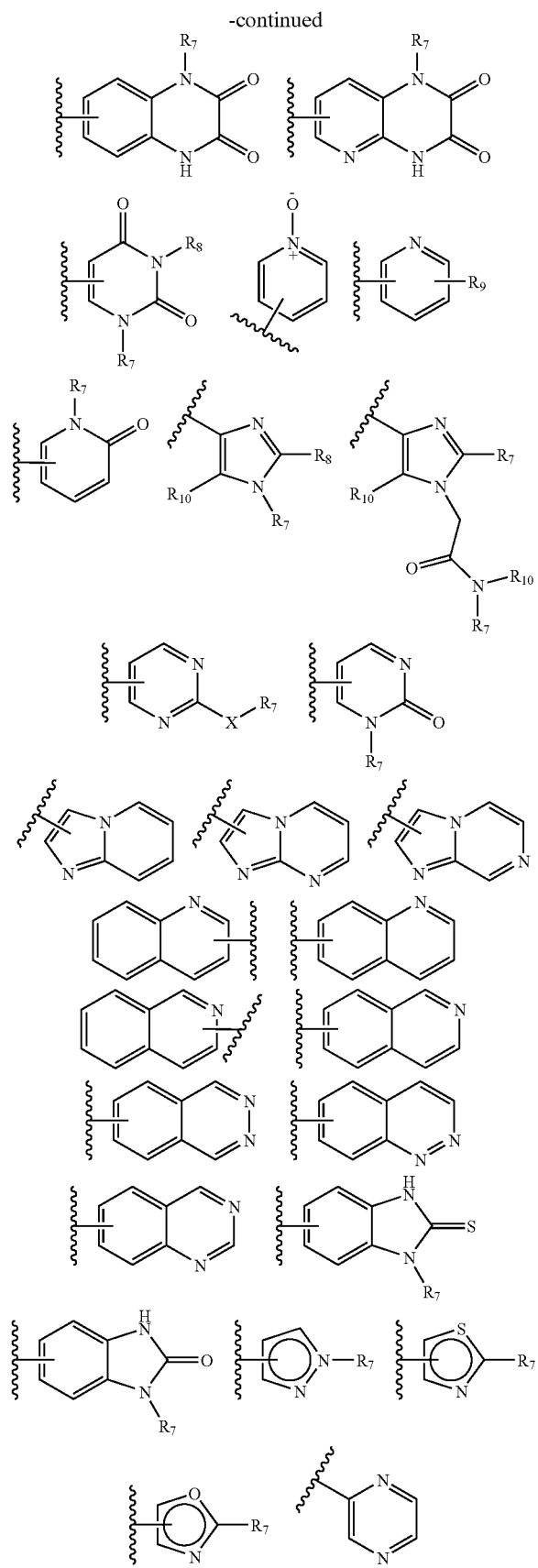

each $R_3$ also having up to three $R_{10}$ substituents attached to the ring of $R_3$ containing at least one N;

$R_4$, $R_5$, $R_{10}$, $R_{21}$, $R_{22}$, $R_{23}$, $R_{24}$, $R_{25}$, $R_{26}$, and $R_{27}$ are each independently hydrogen; or linear or branched $(C_1$-$C_6)$-alkyl, $(C_2$-$C_6)$-alkenyl, or $(C_2$-$C_6)$-alkynyl;

each $R_6$ is independently hydrogen; linear or branched $(C_1$-$C_6)$-alkyl, $(C_2$-$C_6)$-alkenyl, or $(C_2$-$C_6)$-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; —$NR_{13}R_{14}$; —C(OH)(CF$_3$)$_2$; —CH(CF$_3$)$_2$; —C(CF$_3$)$_3$; —$XR_{13}$; or —$COR_{13}$; and when two $R_6$ are ortho to each other, they may together form a five- to seven-membered cyclic group containing up to 3 heteroatoms selected from N, O, or S, and wherein the cyclic group formed by the ortho $R_6$ groups is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_7$ and $R_9$ are each independently hydrogen; linear or branched $(C_1$-$C_6)$-alkyl, $(C_2$-$C_6)$-alkenyl, or $(C_2$-$C_6)$-alkynyl; —$(CH_2)_nXR_{12}$; —$(CH_2)_nR_{17}$; —$COXR_{11}$; —$XR_{11}$; —$CO_2R_{11}$; or —$CONR_{11}R_{12}$;

$R_8$ is hydrogen; linear or branched $(C_1$-$C_6)$-alkyl, $(C_2$-$C_6)$-alkenyl, or $(C_2$-$C_6)$-alkynyl; —$(CH_2)_mCO_2R_{11}$; or —$(CH_2)_mCONR_{11}R_{12}$;

$R_{11}$ and $R_{12}$ are each independently hydrogen; linear or branched $(C_1$-$C_6)$-alkyl, $(C_2$-$C_6)$-alkenyl, or $(C_2$-$C_6)$-alkynyl; or $R_{11}$ and $R_{12}$ may together form a three- to seven-membered heterocyclic group containing up to 3 heteroatoms selected from N, O, or S;

$R_{13}$ and $R_{14}$ are each independently hydrogen; linear or branched $(C_1$-$C_6)$-alkyl, $(C_2$-$C_6)$-alkenyl, or $(C_2$-$C_6)$-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$R_{23}CO_2R_{23}$, —$NR_{23}COR_{23}$, —$NR_{23}CON(R_{23})_2$, or —$CON(R_{23})_2$; aryl; or aryl optionally substituted with one to three substituents selected from halogen, $R_{15}$, —$OR_{15}$, or —$NR_{15}R_{16}$; or $R_{13}$ and $R_{14}$ may together form a three- to seven-membered heterocyclic group containing up to 3 heteroatoms selected from N, O, or S, and wherein the heterocyclic group formed by $R_{13}$ and $R_{14}$ is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_{15}$ and $R_{16}$ are each independently hydrogen; or linear or branched $(C_1$-$C_6)$-alkyl, $(C_2$-$C_6)$-alkenyl, or $(C_2$-$C_6)$-alkynyl; or both $R_{15}$ and $R_{16}$ may together form a three- to seven-membered heterocyclic group containing up to 3 heteroatoms selected from N, O, or S;

$R_{17}$ is phenyl, 2-pyridyl, 3-pyridyl, or 4-pyridyl;

$R_{18}$, $R_{19}$, and $R_{20}$ are each independently hydrogen; linear or branched $(C_1$-$C_6)$-alkyl, $(C_2$-$C_6)$-alkenyl, or $(C_2$-$C_6)$-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; halogen; —$NR_{13}R_{14}$; —C(OH)(CF$_3$)$_2$; —CH(CF$_3$)$_2$; —C(CF$_3$)$_3$; —$XR_{13}$; —$COR_{13}$; —$CO_2R_{13}$; or —$CON(R_{13})(R_{14})$;

X is —O—, —$NR_{12}$—, or —$SO_m$—;

each m is independently 0, 1, or 2; and each n is independently 0, 1, 2, 3, or 4.

In one embodiment, Ar is phenyl.

In another embodiment, one $R_6$ substituent is attached at the 4 position of phenyl.

In one embodiment, $R_1$ and $R_2$ are each independently hydrogen; linear or branched $(C_1$-$C_6)$-alkyl; or $R_1$ and $R_2$ may together form a three- to seven-membered cycloalkyl group.

In another embodiment, $R_1$ and $R_2$ are hydrogen.

In one embodiment, $R_1$ is linear or branched $(C_1$-$C_6)$-alkyl and $R_2$ is hydrogen.

In one embodiment, $R_1$ is methyl and $R_2$ is hydrogen.

In one embodiment, when $R_1$ and $R_2$ are different, the compound or pharmaceutically acceptable salt of the compound is the S-enantiomer with respect to the carbon to which $R_1$ and $R_2$ are bound.

In another embodiment, when $R_1$ and $R_2$ are different, the compound or pharmaceutically acceptable salt of the compound is the R-enantiomer with respect to the carbon to which $R_1$ and $R_2$ are bound.

In one embodiment, $R_4$ and $R_5$ are each independently hydrogen, or linear or branched $(C_1$-$C_6)$-alkyl.

In one embodiment, $R_4$ and $R_5$ are hydrogen.

In another embodiment, $R_4$ is linear or branched $(C_1$-$C_6)$-alkyl and $R_5$ is hydrogen.

In one embodiment, $R_4$ is methyl or ethyl and $R_5$ is hydrogen.

In another embodiment, when $R_4$ is other than hydrogen, the compound or pharmaceutically acceptable salt of the compound is the S-enantiomer with respect to the carbon to which $R_4$ is bound.

In one embodiment, when $R_1$ and $R_2$ are different, the compound or pharmaceutically acceptable salt of the compound is the S-enantiomer with respect to the carbon to which $R_1$ and $R_2$ are bound, and when $R_4$ is other than hydrogen, the compound or pharmaceutically acceptable salt of the compound is the S-enantiomer with respect to the carbon to which $R_4$ is bound.

In another embodiment, when $R_1$ and $R_2$ are different, the compound or pharmaceutically acceptable salt of the compound is the R-enantiomer with respect to the carbon to which $R_1$ and $R_2$ are bound, and when $R_4$ is other than hydrogen, the compound or pharmaceutically acceptable salt of the compound is the S-enantiomer with respect to the carbon to which $R_4$ is bound.

In one embodiment, $R_6$ is hydrogen, linear or branched $(C_1$-$C_6)$-alkyl, —$N(R_{23})_2$, or —$NR_{13}R_{14}$; $R_{23}$ is linear or branched $(C_1$-$C_6)$-alkyl; and $R_{13}$ and $R_{14}$ are each independently linear or branched $(C_1$-$C_6)$-alkyl, each optionally substituted with —$OR_{23}$, —$SR_{23}$, or —$N(R_{23})_2$; or $R_{13}$ and $R_{14}$ may be taken together to form a three- to seven-membered heterocyclic group containing one or two heteroatoms selected from N or O, and optionally substituted with —$OR_{23}$, —$SR_{23}$, —$N(R_{23})_2$, or —$(CH_2)_nOR_{23}$.

In one embodiment, $R_6$ is ethyl, t-butyl, —$N(CH_2CH_3)_2$, pyrrolidine, 2-hydroxymethylpyrrolidine, or isopropyl.

In one embodiment, $R_3$ is

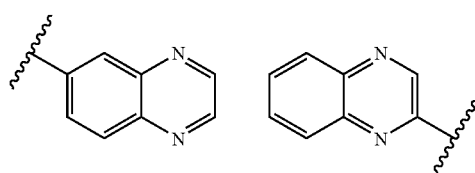

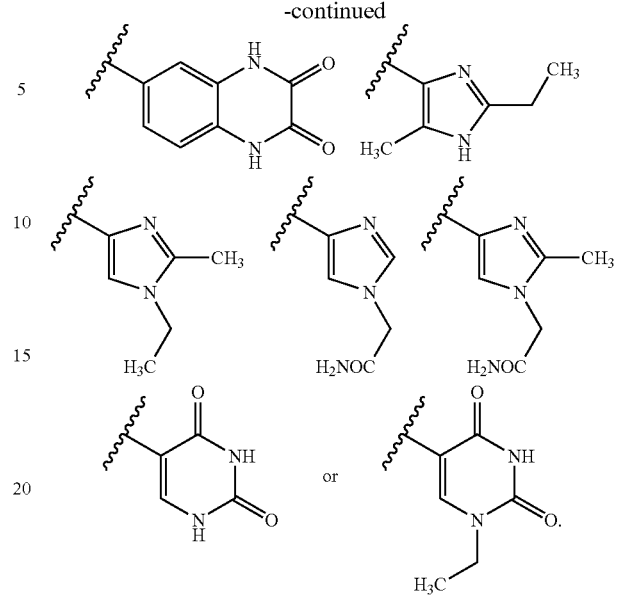

In another embodiment, $R_3$ is

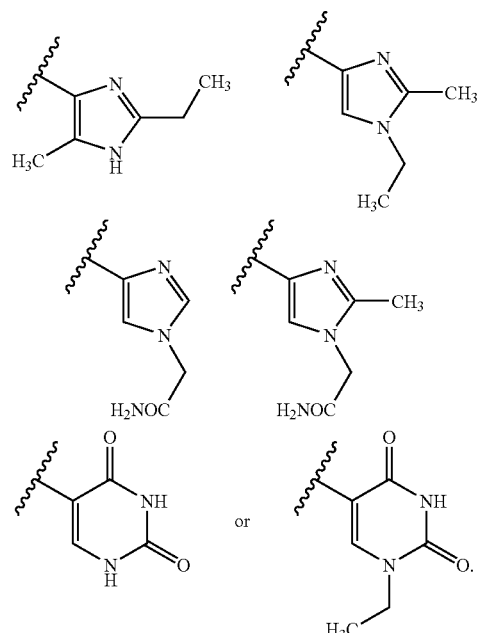

In one embodiment, $R_{18}$, $R_{19}$, $R_{20}$, $R_{21}$, $R_{22}$, $R_{24}$, $R_{25}$, $R_{26}$, and $R_{27}$ are each independently hydrogen, or linear or branched $(C_1$-$C_6)$-alkyl.

In another embodiment, $R_{18}$, $R_{19}$, $R_{20}$, $R_{21}$, $R_{22}$, $R_{24}$, $R_{25}$, $R_{26}$, and $R_{27}$ are each hydrogen.

In one embodiment, $R_{18}$, $R_{19}$, $R_{20}$, $R_{21}$, $R_{22}$, $R_{24}$, $R_{25}$, $R_{26}$, and $R_{27}$ are each hydrogen; $R_1$, $R_2$, $R_4$, and $R_5$ are each independently hydrogen, or linear or branched $(C_1$-$C_6)$-alkyl; Ar is phenyl; $R_6$ is attached at the 4-position of phenyl; $R_6$ is linear or branched $(C_1$-$C_6)$-alkyl, —$N(R_{23})_2$, or —$NR_{13}R_{14}$; $R_{23}$ is linear or branched $(C_1$-$C_6)$-alkyl; $R_{13}$ and $R_{14}$ are each independently linear or branched $(C_1$-$C_6)$-alkyl, each optionally substituted with —$OR_{23}$, —$SR_{23}$, or —$N(R_{23})_2$; or $R_{13}$ and $R_{14}$ may be taken together to form a three- to seven-membered heterocyclic group containing one or two heteroatoms selected from N or O, and optionally substituted with —$OR_{23}$, —$SR_{23}$, —$N(R_{23})_2$, or —$(CH_2)_nOR_{23}$; and $R_3$ is

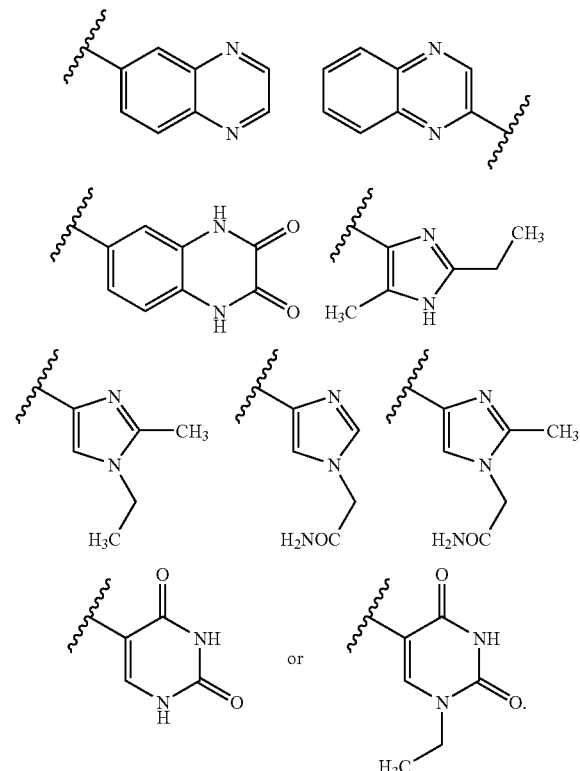

In one embodiment, $R_2$, $R_5$, $R_{18}$, $R_{19}$, $R_{20}$, $R_{21}$, $R_{22}$, $R_{24}$, $R_{25}$, $R_{26}$, and $R_{27}$ are each hydrogen; $R_1$ and $R_4$ are each independently hydrogen, methyl, or ethyl; Ar is phenyl; $R_6$ is attached at the 4-position of phenyl; $R_6$ is ethyl, t-butyl, —$N(CH_2CH_3)_2$, pyrrolidine, 2-hydroxymethylpyrrolidine, or isopropyl; and $R_3$ is

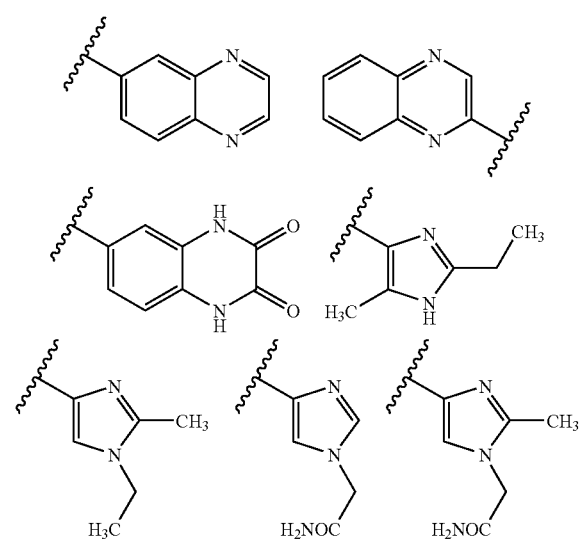

-continued

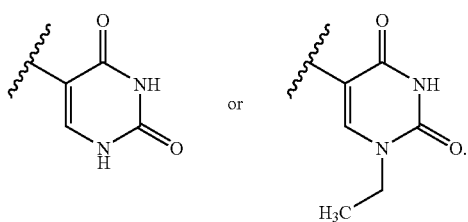

Compounds of the Formula (II)

In another embodiment, the invention provides compounds of the Formula (II):

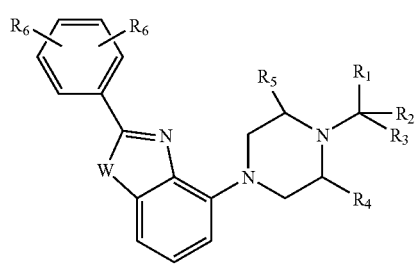

(II)

and pharmaceutically acceptable salts thereof,
wherein
W is O or S;
$R_1$ and $R_2$ are each independently hydrogen; or linear or branched $(C_1-C_6)$-alkyl, $(C_2-C_6)$-alkenyl, or $(C_2-C_6)$-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; or $R_1$ and $R_2$ may together form a three- to seven-membered cycloalkyl group, wherein the cycloalkyl group formed by $R_1$ and $R_2$ is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;
$R_3$ is one of the following:

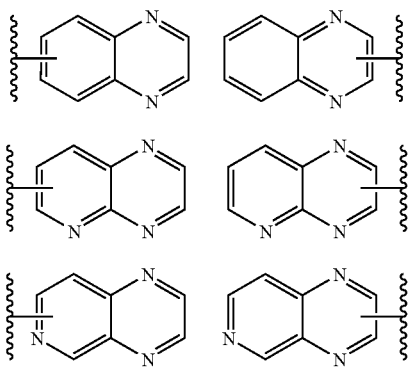

each $R_3$ also having up to three $R_{10}$ substituents attached to the ring of $R_3$ containing at least one N;

$R_4$, $R_5$, $R_{10}$, and $R_{23}$ are each independently hydrogen; or linear or branched $(C_1\text{-}C_6)$-alkyl, $(C_2\text{-}C_6)$-alkenyl, or $(C_2\text{-}C_6)$-alkynyl;

each $R_6$ is independently hydrogen; linear or branched $(C_1\text{-}C_6)$-alkyl, $(C_2\text{-}C_6)$-alkenyl, or $(C_2\text{-}C_6)$-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; —$NR_{13}R_{14}$; —$C(OH)(CF_3)_2$; —$CH(CF_3)_2$; —$C(CF_3)_3$; —$XR_{13}$; or —$COR_{13}$; and when two $R_6$ are ortho to each other, they may together form a five- to seven-membered cyclic group containing up to 3 heteroatoms selected from N, O, or S, and wherein the cyclic group formed by the ortho $R_6$ groups is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_7$ and $R_9$ are each independently hydrogen; linear or branched $(C_1\text{-}C_6)$-alkyl, $(C_2\text{-}C_6)$-alkenyl, or $(C_2\text{-}C_6)$-alkynyl; —$(CH_2)_nXR_{12}$; —$(CH_2)_nR_{17}$; —$COXR_{11}$; —$XR_{11}$—$CO_2R_{11}$; or —$CONR_{11}R_{12}$;

$R_8$ is hydrogen; linear or branched $(C_1\text{-}C_6)$-alkyl, $(C_2\text{-}C_6)$-alkenyl, or $(C_2\text{-}C_6)$-alkynyl; —$(CH_2)_mCO_2R_{11}$; or —$(CH_2)_mCONR_{11}R_{12}$;

$R_{11}$, and $R_{12}$ are each independently hydrogen; linear or branched $(C_1\text{-}C_6)$-alkyl, $(C_2\text{-}C_6)$-alkenyl, or $(C_2\text{-}C_6)$-alkynyl; or $R_{11}$ and $R_{12}$ may together form a three- to seven-membered heterocyclic group containing up to 3 heteroatoms selected from N, O, or S;

$R_{13}$ and $R_{14}$ are each independently hydrogen; linear or branched $(C_1\text{-}C_6)$-alkyl, $(C_2\text{-}C_6)$-alkenyl, or $(C_2\text{-}C_6)$-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; aryl; or aryl optionally substituted with one to three substituents selected from halogen, $R_{15}$, —$OR_{15}$, or —$NR_{15}R_{16}$; or $R_{13}$ and $R_{14}$ may together form a three- to seven-membered heterocyclic group containing up to 3 heteroatoms selected from N, O, or S, and wherein the heterocyclic group formed by $R_{13}$ and $R_{14}$ is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_{15}$ and $R_{16}$ are each independently hydrogen; or linear or branched $(C_1\text{-}C_6)$-alkyl, $(C_2\text{-}C_6)$-alkenyl, or $(C_2\text{-}C_6)$-alkynyl; or both $R_{15}$ and $R_{16}$ may together form a three- to seven-membered heterocyclic group containing up to 3 heteroatoms selected from N, O, or S;

$R_{17}$ is phenyl, 2-pyridyl, 3-pyridyl, or 4-pyridyl;

X is —O—, —$NR_{12}$—, or —$SO_m$—;

each m is independently 0, 1, or 2; and each n is independently 0, 1, 2, 3, or 4.

In one embodiment, W is O.

In another embodiment, W is S.

In one embodiment, one $R_6$ substituent is attached at the 4 position of phenyl.

In one embodiment, $R_1$ and $R_2$ are each independently hydrogen; linear or branched $(C_1\text{-}C_6)$-alkyl; or $R_1$ and $R_2$ may together form a three- to seven-membered cyclic group.

In another embodiment, $R_1$ and $R_2$ are hydrogen.

In one embodiment, $R_1$ is linear or branched $(C_1-C_6)$-alkyl and $R_2$ is hydrogen.

In one embodiment, $R_1$ is methyl and $R_2$ is hydrogen.

In one embodiment, when $R_1$ and $R_2$ are different, the compound or pharmaceutically acceptable salt of the compound is the S-enantiomer with respect to the carbon to which $R_1$ and $R_2$ are bound.

In another embodiment, when $R_1$ and $R_2$ are different, the compound or pharmaceutically acceptable salt of the compound is the R-enantiomer with respect to the carbon to which $R_1$ and $R_2$ are bound.

In one embodiment, $R_4$ and $R_5$ are each independently hydrogen, or linear or branched $(C_1-C_6)$-alkyl.

In one embodiment, $R_4$ and $R_5$ are hydrogen.

In another embodiment, $R_4$ is linear or branched $(C_1-C_6)$-alkyl and $R_5$ is hydrogen.

In one embodiment, $R_4$ is methyl or ethyl and $R_5$ is hydrogen.

In another embodiment, when $R_4$ is other than hydrogen, the compound or pharmaceutically acceptable salt of the compound is the S-enantiomer with respect to the carbon to which $R_4$ is bound.

In one embodiment, when $R_1$ and $R_2$ are different, the compound or pharmaceutically acceptable salt of the compound is the S-enantiomer with respect to the carbon to which $R_1$ and $R_2$ are bound, and when $R_4$ is other than hydrogen, the compound or pharmaceutically acceptable salt of the compound is the S-enantiomer with respect to the carbon to which $R_4$ is bound.

In another embodiment, when $R_1$ and $R_2$ are different, the compound or pharmaceutically acceptable salt of the compound is the R-enantiomer with respect to the carbon to which $R_1$ and $R_2$ are bound, and when $R_4$ is other than hydrogen, the compound or pharmaceutically acceptable salt of the compound is the S-enantiomer with respect to the carbon to which $R_4$ is bound.

In one embodiment, $R_6$ is hydrogen, linear or branched $(C_1-C_6)$-alkyl, $-N(R_{23})_2$, or $-NR_{13}R_{14}$; $R_{23}$ is linear or branched $(C_1-C_6)$-alkyl; and $R_{13}$ and $R_{14}$ are each independently linear or branched $(C_1-C_6)$-alkyl, each optionally substituted with $-OR_{23}$, $-SR_{23}$, or $-N(R_{23})_2$; or $R_{13}$ and $R_{14}$ may be taken together to form a three- to seven-membered heterocyclic group containing one or two heteroatoms selected from N or O, and optionally substituted with $-OR_{23}$, $-SR_{23}$, $-N(R_{23})_2$, or $-(CH_2)_nOR_{23}$.

In one embodiment, $R_6$ is ethyl, t-butyl, $-N(CH_2CH_3)_2$, pyrrolidine, 2-hydroxymethylpyrrolidine, or isopropyl.

In one embodiment, $R_3$ is

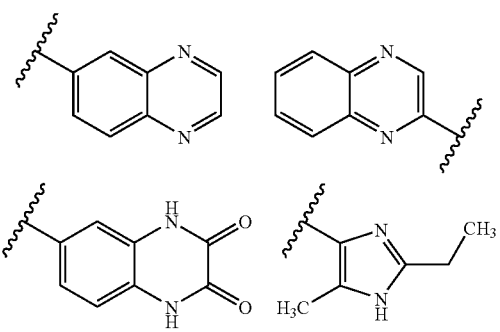

-continued

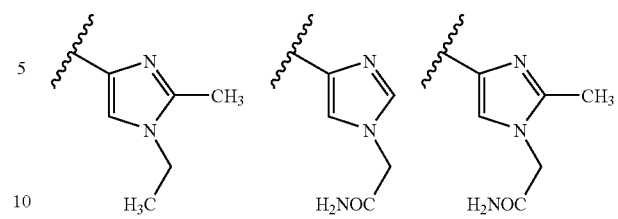

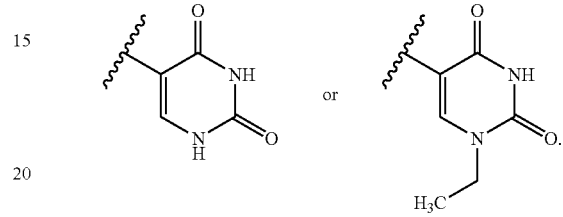

In another embodiment, $R_3$ is

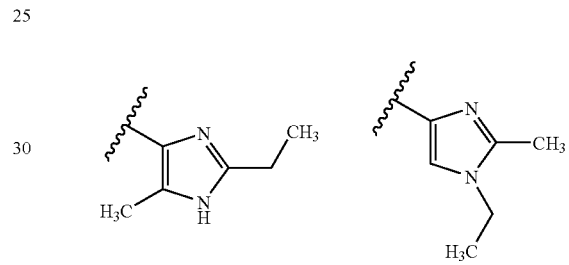

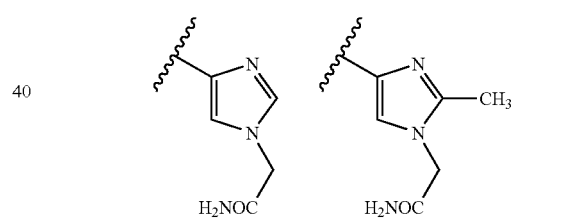

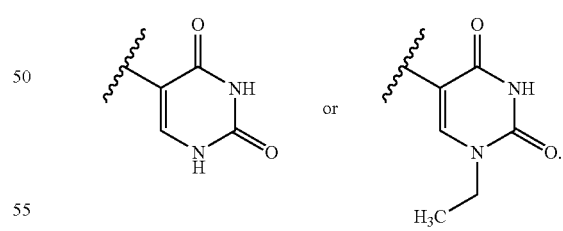

In one embodiment, $R_1$, $R_2$, $R_4$, and $R_5$ are each independently hydrogen, or linear or branched $(C_1-C_6)$-alkyl; $R_6$ is attached at the 4-position of phenyl; $R_6$ is linear or branched $(C_1-C_6)$-alkyl, $-N(R_{23})_2$, or $-NR_{13}R_{14}$; $R_{23}$ is linear or branched $(C_1-C_6)$-alkyl; $R_{13}$ and $R_{14}$ are each independently linear or branched $(C_1-C_6)$-alkyl, each optionally substituted with $-OR_{23}$, $-SR_{23}$, or $-N(R_{23})_2$; or $R_{13}$ and $R_{14}$ may be taken together to form a three- to seven-membered heterocy clic group containing one or two heteroatoms selected from N or O, and optionally substituted with —OR$_{23}$, —SR$_{23}$, —N(R$_{23}$)$_2$, or —(CH$_2$)$_n$OR$_{23}$; and R$_3$ is

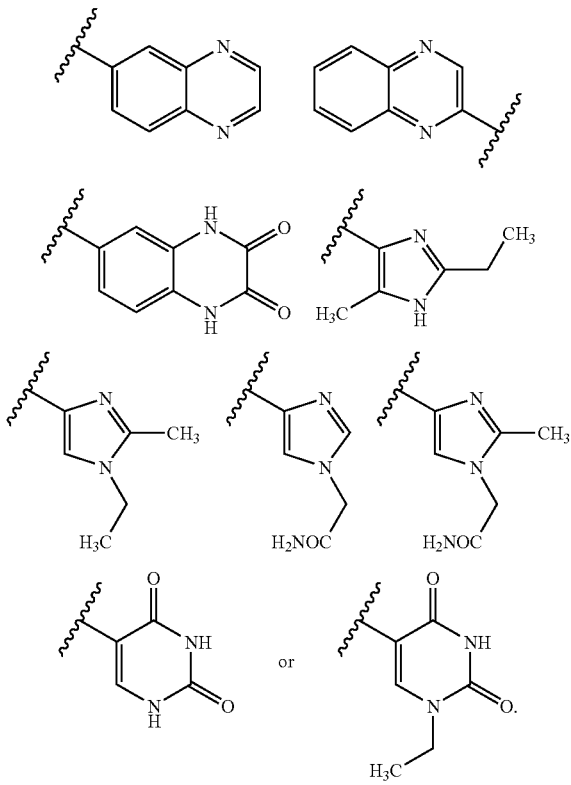

In one embodiment, R$_2$, and R$_5$ are each hydrogen; R$_1$ and R$_4$ are each independently hydrogen, methyl, or ethyl; R$_6$ is attached at the 4-position of phenyl; R$_6$ is ethyl, t-butyl, —N(CH$_2$CH$_3$)$_2$, pyrrolidine, 2-hydroxymethylpyrrolidine, or isopropyl; and R$_3$ is

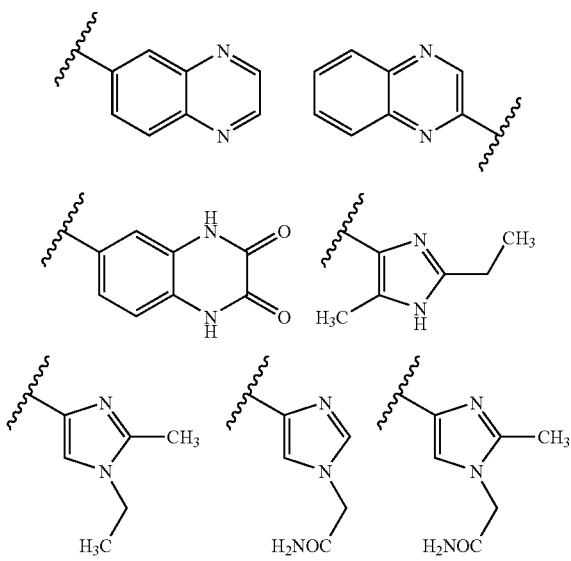

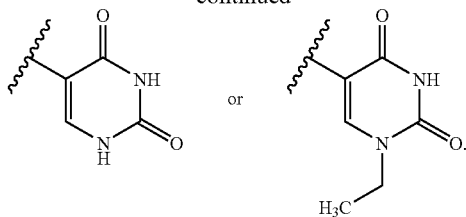

Methods for Making the Compounds and Pharmaceutically Acceptable Salts of Compounds of the Invention The compounds and pharmaceutically acceptable salts of compounds of the present invention can be prepared using a variety of methods starting from commercially available compounds, known compounds, or compounds prepared by known methods. General synthetic routes to many of the compounds of the invention are included in the following schemes. It is understood by those skilled in the art that protection and deprotection steps not shown in the Schemes may be required for these syntheses, and that the order of steps may be changed to accommodate functionality in the target molecule.

Scheme 1 demonstrates the synthesis of a compound or pharmaceutically acceptable salt of a compound of the Formula (IA), wherein Ar, R$_1$, R$_2$, R$_3$, R$_4$, R$_5$, R$_6$, R$_{18}$, R$_{19}$, R$_{20}$, R$_{21}$, R$_{22}$, R$_{24}$, R$_{25}$, R$_{26}$, and R$_{27}$ are as defined above and PG is hydrogen or an amine protecting group. A compound of the Formula (III) is first treated with a piperazine, thereby providing a compound having the Formula (IV), which is then treated under conditions effective to introduce a hydroxyl group, thereby providing a compound having the Formula (V). The compound of the Formula (V) is subsequently reacted under conditions effective to reduce the nitro group, bring about cyclization to form a benzooxazole ring, and deprotect the piperazine to provide a compound of the Formula (VI). The free amine of the compound of Formula (VI) is subsequently reacted under conditions effective to provide a compound of the Formula (IA).

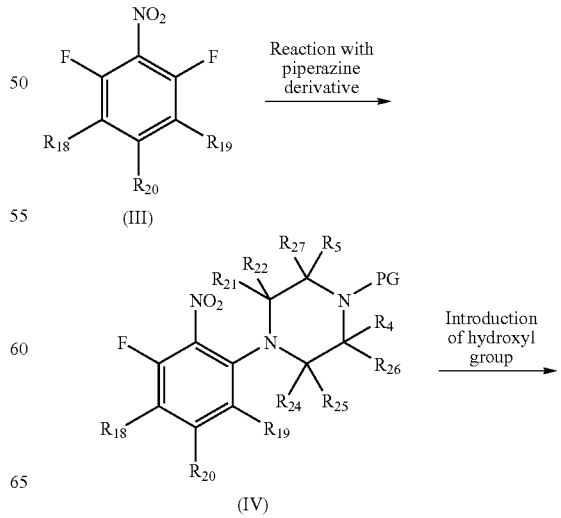

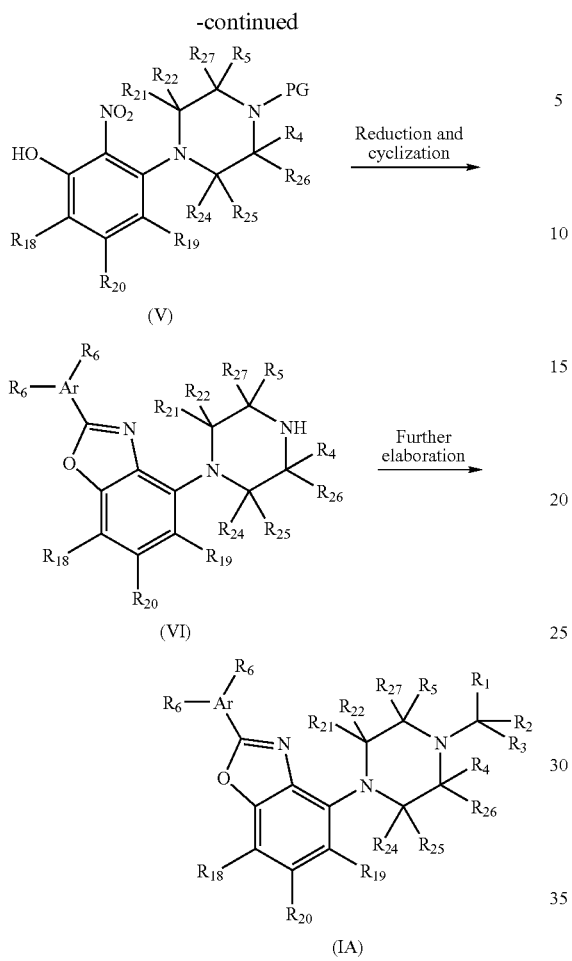

Scheme 2 provides the synthesis of a specific intermediate following the general procedures set forth in Scheme 1, which can be further elaborated to provide compounds of the Formula (IA). As shown in Scheme 2, 2,6-difluoronitrobenzene was first treated with Boc protected piperazine, then with methylsulfanyl ethoxide to introduce the piperazine ring and hyrdoxy groups, respectively. A one-pot Pd catalyzed reduction of the nitro group to the amino group, followed by imine formation and oxazole formation, followed by removal of the Boc protecting group afforded intermediate 1, with the yields for each step ranging from 68 to 92%.

Further elaboration of the intermediate 1, can include, for example, alkylation with 6-bromomethyl-quinoxaline heated in the presence of DIEA in a solvent such as acetonitrile, or reductive amination of an appropriate aldehyde in the presence of NaBH(OAc)$_3$ in a solvent such as NMP or DCE.

Scheme 2

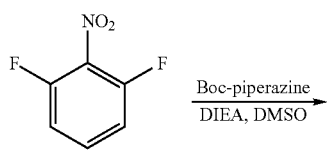

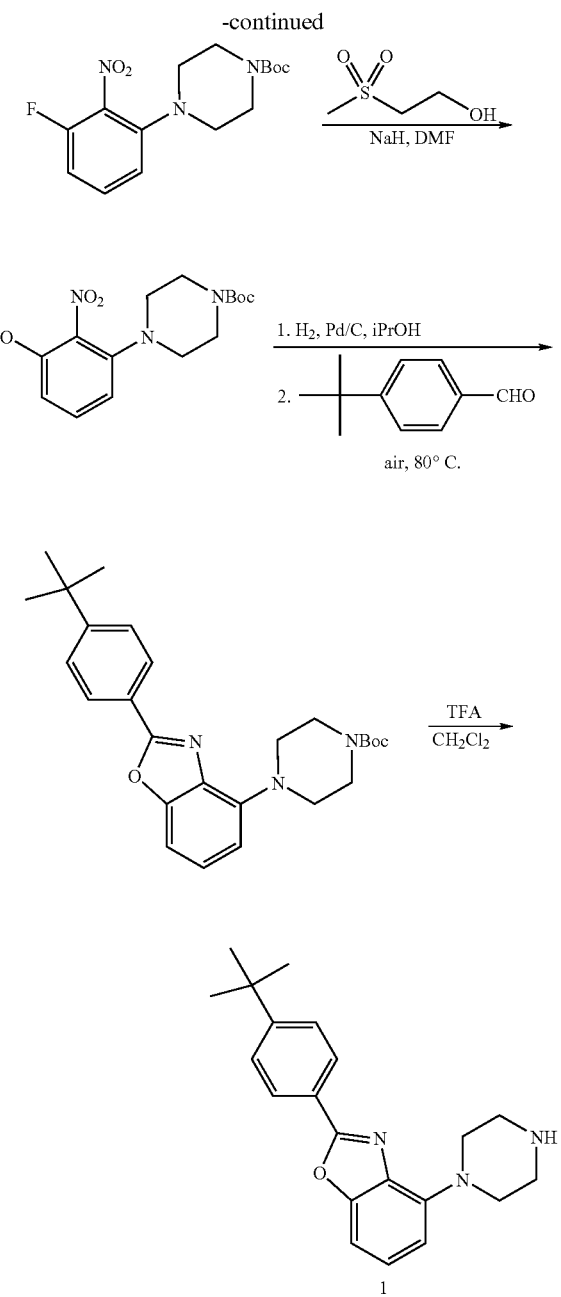

Scheme 3 demonstrates the synthesis of a compound or pharmaceutically acceptable salt of a compound of Formula (IC) wherein Ar, $R_1$, $R_2$, $R_3$, $R_4$, $R_5$, $R_6$, $R_{18}$, $R_{19}$, $R_{20}$, $R_{21}$, $R_{22}$, $R_{24}$, $R_{25}$, $R_{26}$, and $R_{27}$ are as defined above. As shown in Scheme 3, a compound of Formula (VII) is selectively reduced, thereby providing a compound having the Formula (VIII).

The compound of Formula (VIII) is then acylated to provide a compound of the Formula (IX), followed by cyclization to provide a compound of the Formula (X). Formation of the piperazine ring results in a compound of the Formula (XI). The free amine of the piperazine of the compound of Formula (XI) is subsequently reacted under conditions effective to provide a compound of the Formula (IC).

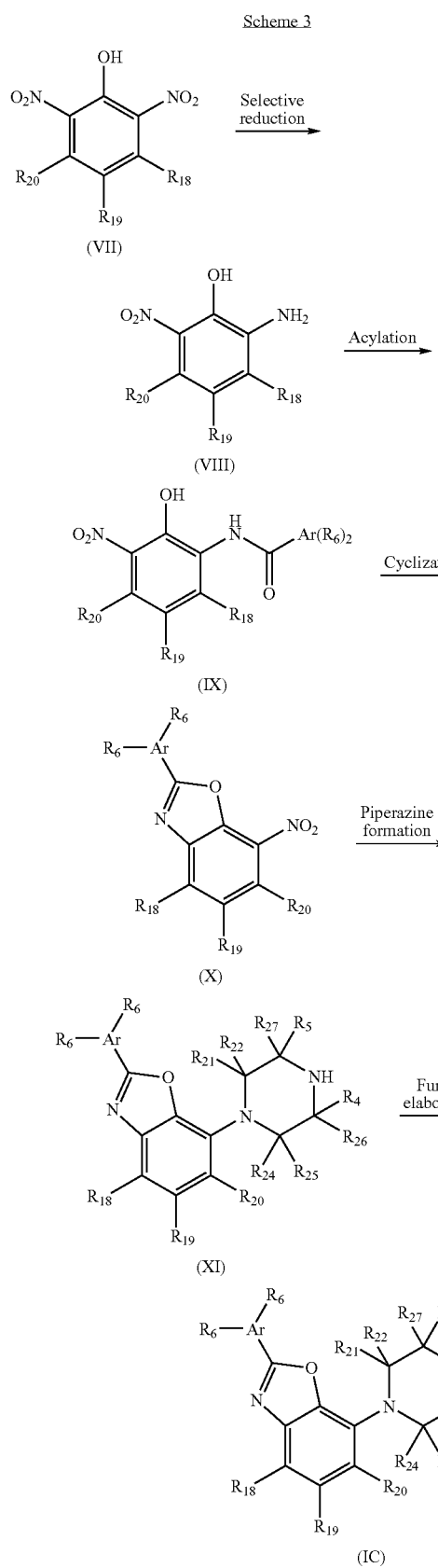

Scheme 3

Scheme 4 provides the synthesis of a specific intermediate following the general procedures set forth in Scheme 3, which can be further elaborated to provide compounds of the Formula (IC). As shown in Scheme 4, 2,6-dinitrophenol was selectively reduced to the mono aniline, which was treated with CDI-activated acid to form the amide. Acid-catalyzed ring closure formed the oxazole ring. The second nitro group was reduced to the aniline, which reacted with the dichloroamine to form the piperazine ring of intermediate 2, with the yields for each step ranging from 20 to 75%.

Further elaboration of the intermediate 2, can include, for example, alkylation with 6-bromomethyl-quinoxaline heated in the presence of DIEA in a solvent such as acetonitrile, or reductive amination of an appropriate aldehyde in the presence of $NaBH(OAc)_3$ in a solvent such as NMP or DCE.

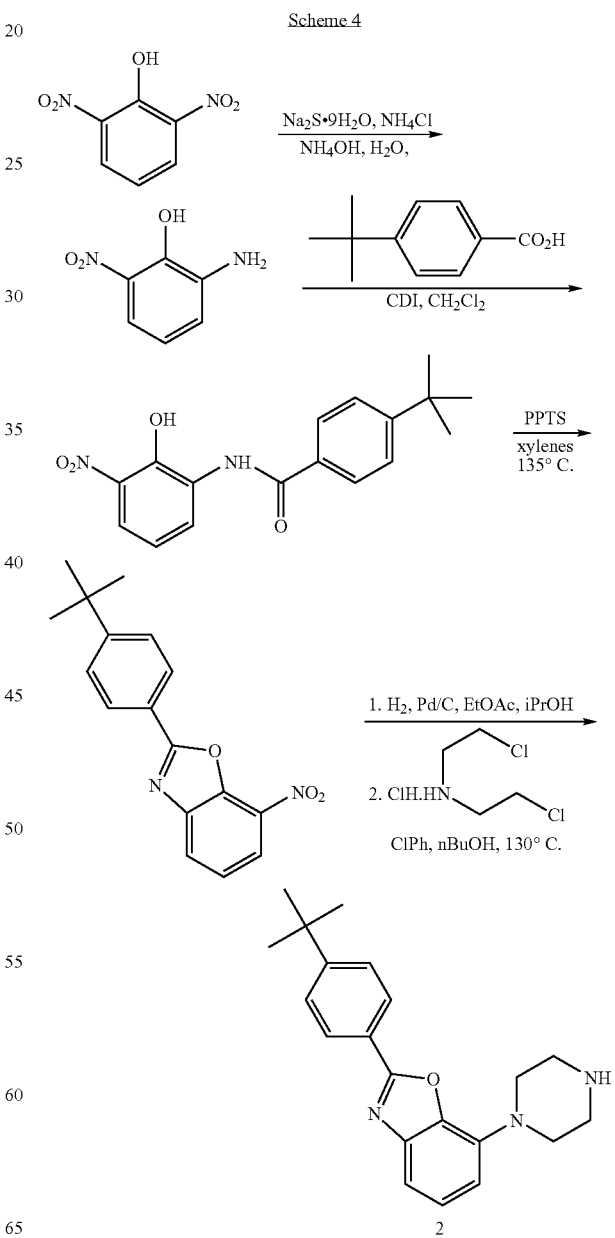

Scheme 4

Scheme 5 demonstrates the synthesis of a compound or pharmaceutically acceptable salt of a compound of the Formula (IB), wherein Ar, $R_1$, $R_2$, $R_3$, $R_4$, $R_5$, $R_6$, $R_{18}$, $R_{19}$, $R_{20}$, $R_{21}$, $R_{22}$, $R_{24}$, $R_{25}$, $R_{26}$, and $R_{27}$ are as defined above. As shown in Scheme 5, a compound of the Formula (XII) is acylated to provide a compound of the Formula (XIII), which is thiolated to provide a compound of the Formula (XIV). Cyclization and reaction with piperazine provides a compound of the Formula (XV). Subsequently reacting the free amine of the piperazine of the compound of the Formula (XV) provides a compound of the Formula (IB).

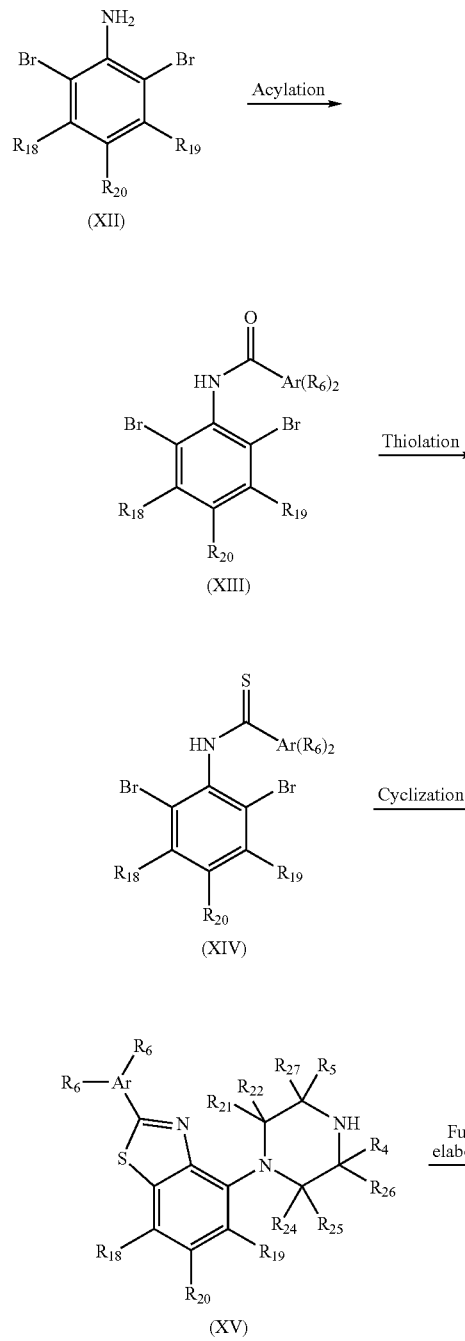

-continued

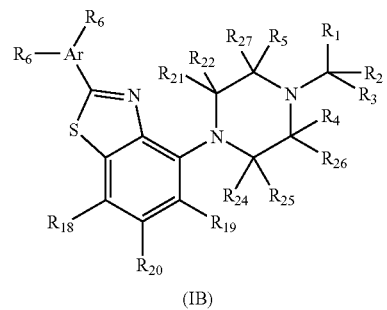

(IB)

Scheme 6 provides the synthesis of a specific intermediate following the general procedures set forth in Scheme 5, which can be further elaborated to provide compounds of the Formula (IB). As shown in Scheme 6, acylation of 2,6-dibromoaniline and conversion to the thioamide provided the dibromo intermediate. A one pot, two-step palladium catalyzed displacement/cyclization reaction followed by piperazine displacement of the second bromine afforded thiazole intermediate 3, with yields for each step ranging from 41 to 81%.

Further elaboration of the intermediate 3, can include, for example, alkylation with 6-bromomethyl-quinoxaline heated in the presence of DIEA in a solvent such as acetonitrile, or reductive amination of an appropriate aldehyde in the presence of $NaBH(OAc)_3$ in a solvent such as NMP or DCE.

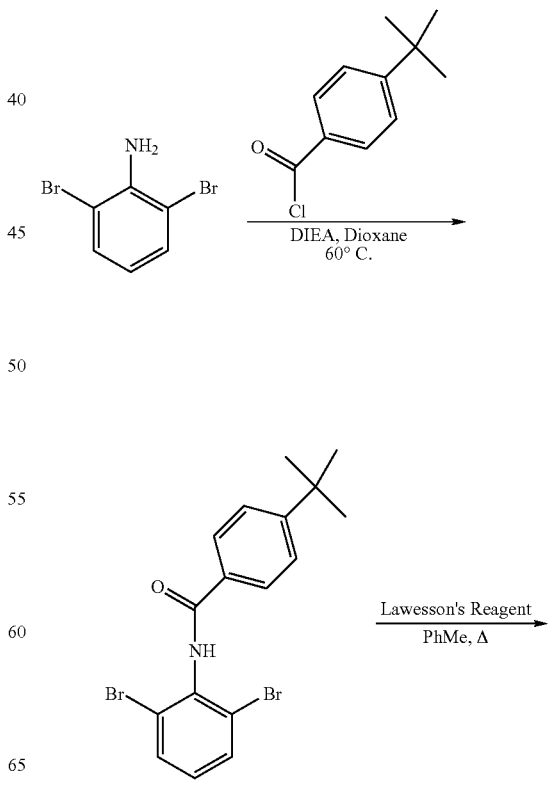

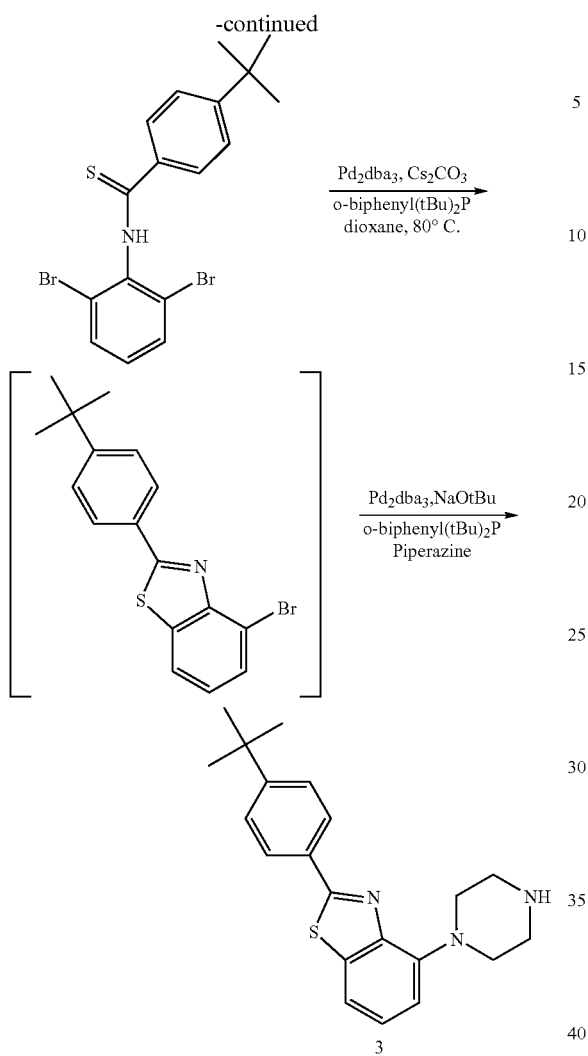

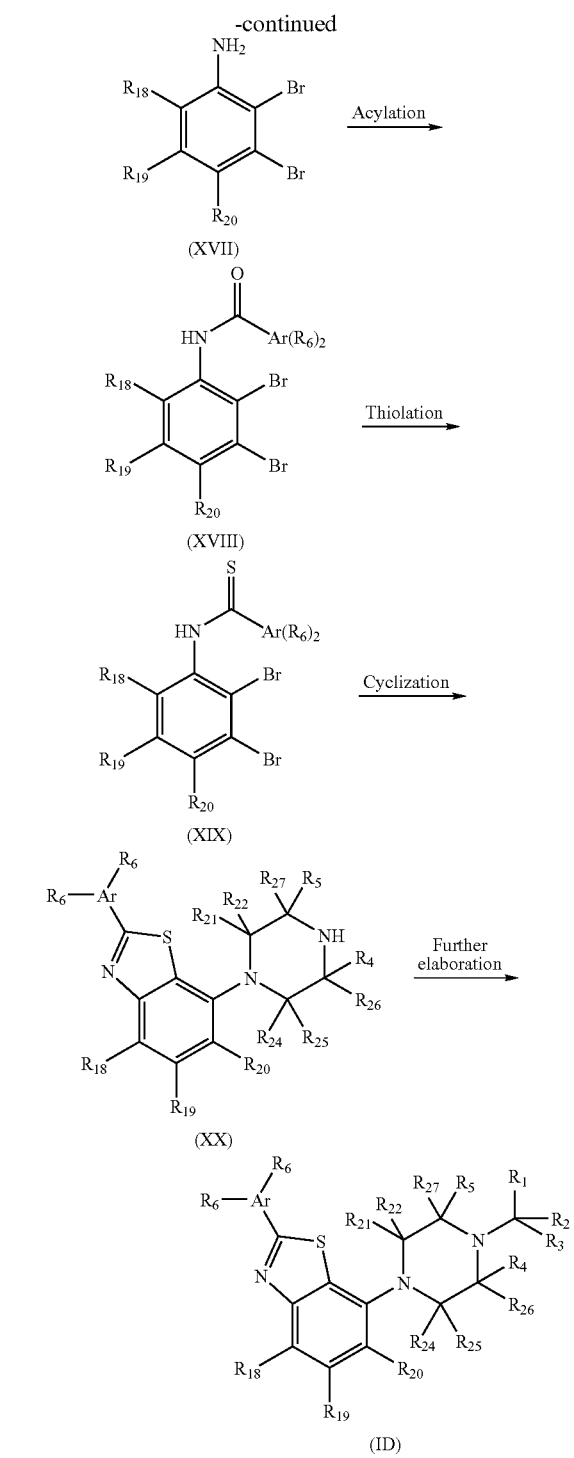

Scheme 7 shows the synthesis of a compound or pharmaceutically acceptable salt of a compound of the Formula (ID), wherein Ar, $R_1$, $R_2$, $R_3$, $R_4$, $R_5$, $R_6$, $R_{18}$, $R_{19}$, $R_{20}$, $R_{21}$, $R_{22}$, $R_{24}$, $R_{25}$, $R_{26}$, and $R_{27}$ are as defined above. As shown in Scheme 7, a compound of the Formula (XVI) is nitrated and then reduced to provide a compound of the Formula (XVII). The compound of the Formula (XVII) is then acylated to provide the compound of the Formula (XVIII), thiolated to provide a compound of the Formula (XIX), followed by cyclization to provide a compound of the Formula (XX). Subsequently reacting the free amine of the piperazine of the compound of the Formula (XX) provides a compound of the Formula (ID).

Scheme 7

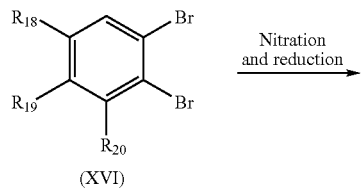

Scheme 8 provides the synthesis of a specific intermediate following the general procedures set forth in Scheme 7, which can be further elaborated to provide a compound of the Formula (ID). As shown in Scheme 8, nitration of 1,2-dibromobenzene, followed by separation of the two isomeric products to obtain the desired 2,3-dibromonitrobenzene, followed by tin (II) chloride reduction afforded the requisite 2,3-dibromoaniline. Acylation of the aniline, and conversion of the amide to the thioamide was followed by a one pot palladium catalyzed displacement/cyclization, followed by piperazine displacement of the second bromine afforded the regioisomeric benzothiazole intermediate 4, with yields for each step ranging from 14 to 81%.

Further elaboration of the intermediate 4, can include, for example, alkylation with 6-bromomethyl-quinoxaline heated in the presence of DIEA in a solvent such as acetonitrile, or reductive amination of an appropriate aldehyde in the presence of NaBH(OAc)$_3$ in a solvent such as NMP or DCE.

Scheme 8

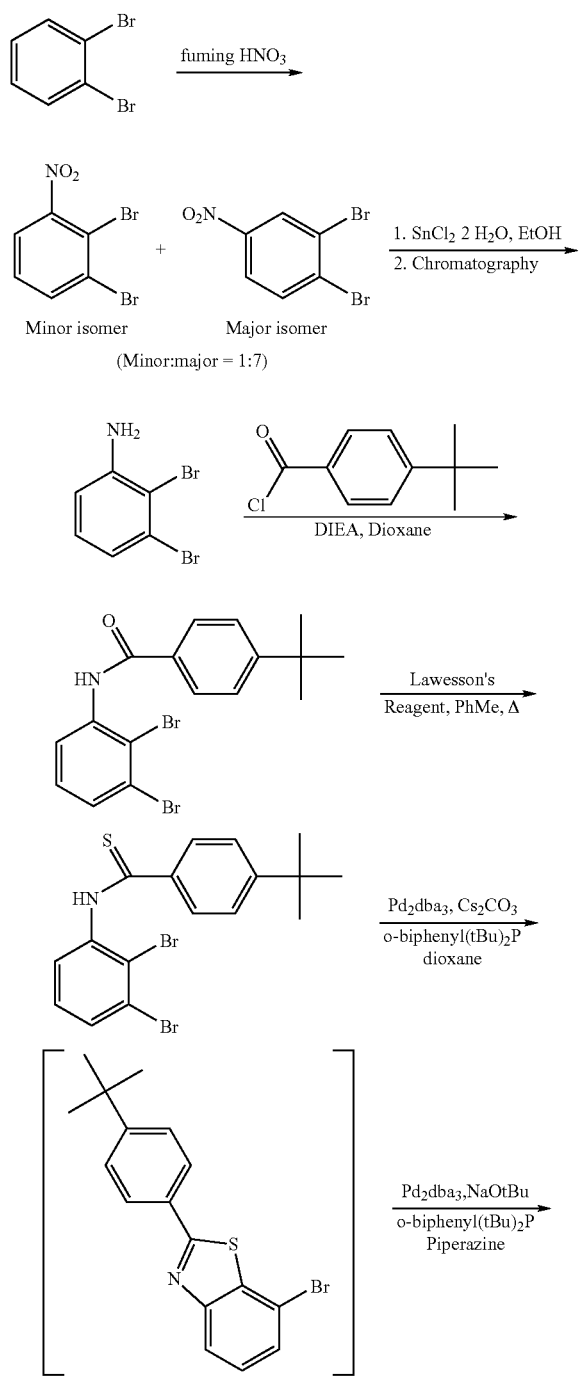

-continued

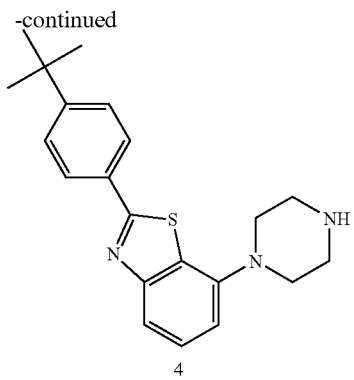

4

One of skill in the art will recognize that Schemes 1-8 can be adapted to produce the other compounds and pharmaceutically acceptable salts of compounds according to the present invention.

Therapeutic Administration

When administered to an animal, the compounds or pharmaceutically acceptable salts of the compounds of the invention can be administered neat or as a component of a composition that comprises a physiologically acceptable carrier or vehicle. A composition of the invention can be prepared using a method comprising admixing the compound or a pharmaceutically acceptable salt of the compound and a physiologically acceptable carrier, excipient, or diluent. Admixing can be accomplished using methods well known for admixing a compound or a pharmaceutically acceptable salt of the compound and a physiologically acceptable carrier, exipient, or diluent.

The present compositions, comprising compounds or pharmaceutically acceptable salts of the compounds of the invention can be administered orally. The compounds or pharmaceutically acceptable salts of compounds of the invention can also be administered by any other convenient route, for example, by infusion or bolus injection, by absorption through epithelial or mucocutaneous linings (e.g., oral, rectal, vaginal, and intestinal mucosa, etc.) and can be administered together with another therapeutic agent. Administration can be systemic or local. Various known delivery systems, including encapsulation in liposomes, microparticles, microcapsules, and capsules, can be used.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. In some instances, administration will result of release of the compound or a pharmaceutically acceptable salt of the compound into the bloodstream. The mode of administration is left to the discretion of the practitioner.

In one embodiment, the compound or a pharmaceutically acceptable salt of the compound is administered orally.

In another embodiment, the compound or a pharmaceutically acceptable salt of the compound is administered intravenously.

In another embodiment, it may be desirable to administer the compound or a pharmaceutically acceptable salt of the compound locally. This can be achieved, for example, by local infusion during surgery, topical application, e.g., in conjunction with a wound dressing after surgery, by injection, by means of a catheter, by means of a suppository or edema, or by means of an implant, said implant being of a porous, non-porous, or gelatinous material, including membranes, such as sialastic membranes, or fibers.

In certain embodiments, it can be desirable to introduce the compound or a pharmaceutically acceptable salt of the compound into the central nervous system, circulatory system or gastrointestinal tract by any suitable route, including intraventricular, intrathecal injection, paraspinal injection, epidural injection, enema, and by injection adjacent to the peripheral nerve. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compound or a pharmaceutically acceptable salt of the compound can be formulated as a suppository, with traditional binders and excipients such as triglycerides.

In another embodiment, the compound or a pharmaceutically acceptable salt of the compound can be delivered in a vesicle, in particular a liposome (see Langer, *Science* 249: 1527-1533 (1990) and Treat et al., *Liposomes in the Therapy of Infectious Disease and Cancer* 317-327 and 353-365 (1989)).

In yet another embodiment, the compound or a pharmaceutically acceptable salt of the compound can be delivered in a controlled-release system or sustained-release system (see, e.g., Goodson, in *Medical Applications of Controlled Release*, vol. 2, pp. 115-138 (1984)). Other controlled or sustained-release systems discussed in the review by Langer, *Science* 249:1527-1533 (1990) can be used. In one embodiment, a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 2:61 (1983); Levy et al., *Science* 228:190 (1935); During et al., *Ann. Neural.* 25:351 (1989); and Howard et al., *J. Neurosurg.* 71:105 (1989)).

In yet another embodiment, a controlled- or sustained-release system can be placed in proximity of a target of the compound or a pharmaceutically acceptable salt of the compound, e.g., the reproductive organs, thus requiring only a fraction of the systemic dose.

The present compositions can optionally comprise a suitable amount of a physiologically acceptable excipient.

Such physiologically acceptable excipients can be liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one embodiment the physiologically acceptable excipients are sterile when administered to an animal. The physiologically acceptable excipient should be stable under the conditions of manufacture and storage and should be preserved against the contaminating action of microorganisms. Water is a particularly useful excipient when the compound or a pharmaceutically acceptable salt of the compound is administered intravenously. Saline solutions and aqueous dextrose and glycerol solutions can also be employed as liquid excipients, particularly for injectable solutions. Suitable physiologically acceptable excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

Liquid carriers may be used in preparing solutions, suspensions, emulsions, syrups, and elixirs. The compound or pharmaceutically acceptable salt of the compound of this invention can be dissolved or suspended in a pharmaceutically acceptable liquid carrier such as water, an organic solvent, a mixture of both, or pharmaceutically acceptable oils or fat. The liquid carrier can contain other suitable pharmaceutical additives including solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and prenteral administration include water (particular containing additives as above, e.g., cellulose derivatives, including sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule. Other examples of suitable physiologically acceptable excipients are described in *Remington's Pharmaceutical Sciences* 1447-1676 (Alfonso R. Gennaro, ed., 19th ed. 1995).

In one embodiment, the compound or a pharmaceutically acceptable salt of the compound is formulated in accordance with routine procedures as a composition adapted for oral administration to humans. Compositions for oral delivery can be in the form of tablets, lozenges, buccal forms, troches, aqueous or oily suspensions or solutions, granules, powders, emulsions, capsules, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. In powders, the carrier can be a finely divided solid, which is an admixture with the finely divided compound or pharmaceutically acceptable salt of the compound. In tablets, the compound or pharmaceutically acceptable salt of the compound is mixed with a carrier having the necessary compression properties in suitable proportions and compacted in the shape and size desired. The powders and tablets can contain up to about 99% of the compound or pharmaceutically acceptable salt of the compound.

Capsules may contain mixtures of the compounds or pharmaceutically acceptable salts of the compounds with inert fillers and/or diluents such as pharmaceutically acceptable starches (e.g., corn, potato, or tapioca starch), sugars, artificial sweetening agents, powdered celluloses (such as crystalline and microcrystalline celluloses), flours, gelatins, gums, etc.

Tablet formulations can be made by conventional compression, wet granulation, or dry granulation methods and utilize pharmaceutically acceptable diluents, binding agents, lubricants, disintegrants, surface modifying agents (including surfactants), suspending or stabilizing agents (including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrroldine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine.

Moreover, when in a tablet or pill form, the compositions can be coated to delay disintegration and absorption in the gastrointestinal tract, thereby providing a sustained action over an extended period of time. Selectively permeable membranes surrounding an osmotically active driving compound or a pharmaceutically acceptable salt of the compound are also suitable for orally administered compositions. In these latter platforms, fluid from the environment surrounding the capsule can be imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment the excipients are of pharmaceutical grade.

In another embodiment, the compound or a pharmaceutically acceptable salt of the compound can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the compound or a pharmaceutically acceptable salt of the compound is to be administered by infusion, it can be dispensed, for example, with an infusion bottle containing sterile pharmaceutical grade water or saline. Where the compound or a pharmaceutically acceptable salt of the compound is administered by injection, an ampule of sterile water for injection or saline can be provided so that the ingredients can be mixed prior to administration.

In another embodiment, the compound or pharmaceutically acceptable salt of the compound can be administered transdermally thorugh the use of a transdermal patch. Transdermal administrations include administrations across the surface of the body and the inner linings of the bodily passages including epithelial and mucosal tissues. Such administrations can be carried out using the present compounds or pharmaceutically acceptable salts of the compounds, in lotions, creams, foams, patches, suspensions, solutions, and suppositories (e.g., rectal or vaginal).

Transdermal administration can be accomplished through the use of a transdermal patch containing the compound or pharmaceutically acceptable salt of the compound and a carrier that is inert to the compound or pharmaceutically acceptable salt of the compound, is non-toxic to the skin, and allows delivery of the agent for systemic absorption into the blood stream via the skin. The carrier may take any number of forms such as creams or ointments, pastes, gels, or occlusive devices. The creams or ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the compound or pharmaceutically acceptable salt of the compund into the blood stream, such as a semi-permeable membrane covering a reservoir containing the compound or pharmaceutically acceptable salt of the compound with or without a carrier, or a matrix containing the active ingredient.

The compounds or pharmaceutically acceptable salts of the compounds of the invention may be administered rectally or vaginally in the form of a conventional suppository. Suppository formulations may be made from traditional materials, including cocoa butter, with or without the addition of waxes to alter the suppository's melting point, and glycerin. Water-soluble suppository bases, such as polyethylene glycols of various molecular weights, may also be used.

The compound or a pharmaceutically acceptable salt of the compound can be administered by controlled-release or sustained-release means or by delivery devices that are known to those of ordinary skill in the art. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

In one embodiment a controlled- or sustained-release composition comprises a minimal amount of the compound or a pharmaceutically acceptable salt of the compound to treat or prevent a GnRH-related disorder in a minimal amount of time. Advantages of controlled- or sustained-release compositions include extended activity of the drug, reduced dosage frequency, and increased compliance by the animal being treated. In addition, controlled- or sustained-release compositions can favorably affect the time of onset of action or other characteristics, such as blood levels of the compound or a pharmaceutically acceptable salt of the compound, and can thus reduce the occurrence of adverse side effects.

Controlled- or sustained-release compositions can initially release an amount of the compound or a pharmaceutically acceptable salt of the compound that promptly produces the desired therapeutic or prophylactic effect, and gradually and continually release other amounts of the compound or a pharmaceutically acceptable salt of the compound to maintain this level of therapeutic or prophylactic effect over an extended period of time. To maintain a constant level of the compound or a pharmaceutically acceptable salt of the compound in the body, the compound or a pharmaceutically acceptable salt of the compound can be released from the dosage form at a rate that will replace the amount of the compound or a pharmaceutically acceptable salt of the compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

In certain embodiments, the present invention is directed to prodrugs of the compounds or pharmaceutically acceptable salts of compounds of the present invention. Various forms of prodrugs are known in the art, for example as discussed in Bundgaard (ed.), *Design of Prodrugs*, Elsevier (1985); Widder et al. (ed.), *Methods in Enzymology*, vol. 4, Academic Press (1985); Kgrogsgaard-Larsen et al. (ed.); "*Design and Application of Prodrugs*", *Textbook of Drug Design and Development*, Chapter 5, 113-191 (1991); Bundgaard et al., *Journal of Drug Delivery Reviews*, 8:1-38 (1992); Bundgaard et al., *J. Pharmaceutical Sciences*, 77:285 et seq. (1988); and Higuchi and Stella (eds.), *Prodrugs as Novel Drug Delivery Systems*, American Chemical Society (1975).

The amount of the compound or a pharmaceutically acceptable salt of the compound is an amount that is effective for treating or preventing a GnRH-related disorder. In addition, in vitro or in vivo assays can optionally be employed to help identify optimal dosage ranges. The precise dose to be employed can also depend on the route of administration, the condition, the seriousness of the condition being treated, as well as various physical factors related to the individual being treated, and can be decided according to the judgment of a health-care practitioner. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the judgment of a health-care practitioner. The effective dosage amounts described herein refer to total amounts administered; that is, if more than one compound or a pharmaceutically acceptable salt of the compound is administered, the effective dosage amounts correspond to the total amount administered.

The amount of the compound or a pharmaceutically acceptable salt of the compound that is effective for treating or preventing a GnRH-related disorder will typically range from about 0.001 mg/kg to about 250 mg/kg of body weight per day, in one embodiment, from about 1 mg/kg to about 250 mg/kg body weight per day, in another embodiment, from about 1 mg/kg to about 50 mg/kg body weight per day, and in another embodiment, from about 1 mg/kg to about 200 mg/kg of body weight per day.

In one embodiment, the pharmaceutical composition is in unit dosage form, e.g., as a tablet, capsule, powder, solution, suspension, emulsion, granule, or suppository. In such form, the composition is sub-divided in unit dose containing appropriate quantities of the active ingredient; the unit dosage form can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may be given in a single dose or in two or more divided doses.

The compound or a pharmaceutically acceptable salt of the compound can be assayed in vitro or in vivo for the desired therapeutic or prophylactic activity prior to use in humans. Animal model systems can be used to demonstrate safety and efficacy.

The present methods for treating or preventing a GnRH-related disorder, can further comprise administering another therapeutic agent to the animal being administered the compound or a pharmaceutically acceptable salt of the compound. In one embodiment the other therapeutic agent is administered in an effective amount.

Effective amounts of the other therapeutic agents are well known to those skilled in the art. However, it is well within the skilled artisan's purview to determine the other therapeutic agent's optimal effective amount range. The compound or a pharmaceutically acceptable salt of the compound and the other therapeutic agent can act additively or, in one embodiment, synergistically. In one embodiment of the invention, where another therapeutic agent is administered to an animal, the effective amount of the compound or a pharmaceutically acceptable salt of the compound is less than its effective amount would be where the other therapeutic agent is not administered. In this case, without being bound by theory, it is believed that the compound or a pharmaceutically acceptable salt of the compound and the other therapeutic agent act synergistically.

In one embodiment, the other therapeutic agent is selected from the group consisting of at least one of androgen, estrogen, progesterone, antiestrogen, antiprogestogen, testosterone, angiotensin-converting enzyme inhibitor (such as ENALPRIL or CAPTOPRIL), angiotensin II-receptor antagonist (such as LOSARTAN), renin inhibitor, bisphosphonate (bisphosphonic acids), growth hormone secretagogue (such as MK-0677), 5a-reductase 2 inhibitor (such as finasteride or epristeride), 5a-reductase 1 inhibitor (such as 4,7b-dimethyl-4-aza-5a-cholestan-3-one, 3-oxo-4-aza-4,7b-dimethyl-16b-(4-chlorophenoxy)-5a-androstane, and 3-oxo-4-aza-4,7b-dimethyl-16b-(phenoxy)-5a-androstane), a dual inhibitor of 5a-reductase 1 and 5a-reductase 2 (such as 3-oxo-4-aza-17b-(2,5-trifluoromethylphenyl-carbamoyl)-5a-androstan), antiandrogens (such as flutamide, casodex and cyproterone acetate), alpha-1 blockers (such as prazosin, terazosin, doxazosin, tamsulosin, and alftizosin), growth hormone, and luteinizing hormone releasing compounds (such as a peptide, including leuprorelin, gonadorelin, buserelin, triptorelin, goserelin, nafarelin, histrelin, deslorelin, meterlin and recirelin, or a natural hormone or analog thereof).

For example, when used with compounds or pharmaceutically acceptable salts of compounds of the present invention: androgens, estrogens, progesterones, antiestrogens and antiprogestogens find use in the treatment of endometriosis, fibroids, and in contraception; testosterone or other androgens or antiprogestogens find use in men as a contraceptive; angiotensin-converting enzyme inhibitors, angiotensin II-receptor antagonists, and renin inhibitor find use in the treatment of uterine fibroids; bisphosphonates (bisphosphonic acids) and growth hormone secretagogues find use in the treatment and prevention of disturbances of calcium, phosphate and bone metabolism, in particular, for the prevention of bone loss during therapy with the GnRH antagonist, and in combination with estrogens, progesterones, antiestrogens, antiprogesterones and/or androgens for the prevention or treatment of bones loss or hypogonadal symptoms such as hot flashes during therapy with the GnRH antagonist; and growth hormone, growth hormone releasing hormone or growth hormone secretagogues, to delay puberty in growth hormone deficient children. Additional therapeutic agents useful in combination with the compounds or pharmaceutically acceptable salts of compounds of the present invention include 5a-reductase 2 inhibitor, 5a-reductase 1 inhibitor, dual inhibitors of 5a-reductase 1 and 5a-reductase 2, antiandrogens, alpha-1 blockers, and compounds having luteinizing hormone releasing activity.

In one embodiment, the compound or a pharmaceutically acceptable salt of the compound is administered concurrently with another therapeutic agent.

In one embodiment, a composition comprising an effective amount of the compound or a pharmaceutically acceptable salt of the compound and an effective amount of another therapeutic agent within the same composition can be administered.

In another embodiment, a composition comprising an effective amount of the compound or a pharmaceutically acceptable salt of the compound and a separate composition comprising an effective amount of another therapeutic agent can be concurrently administered. In another embodiment, an effective amount of the compound or a pharmaceutically acceptable salt of the compound is administered prior to or subsequent to administration of an effective amount of another therapeutic agent. In this embodiment, the compound or a pharmaceutically acceptable salt of the compound is administered while the other therapeutic agent exerts its therapeutic effect, or the other therapeutic agent is administered while the compound or a pharmaceutically acceptable salt of the compound exerts its preventative or therapeutic effect for treating or preventing a GnRH-related disorder.

Thus, in one embodiment, the invention provides a composition comprising an effective amount of the compound or a pharmaceutically acceptable salt of the compound of the present invention and a pharmaceutically acceptable carrier.

In another embodiment, the composition further comprises a therapeutic agent selected from the group consisting of androgen, estrogen, progesterone, antiestrogen, antiprogestogen, testosterone, angiotensin-converting enzyme inhibitor, angiotensin II-receptor antagonist, renin inhibitor, bisphosphonate, growth hormone secretagogue, 5a-reductase 2 inhibitor, a 5a-reductase 1 inhibitor, a dual inhibitor of 5a-reductase 1 and 5a-reductase 2, antiandrogen, alpha-1 blockers, growth hormone, and luteinizing hormone releasing compound; or a combination thereof.

In another embodiment, the pharmaceutically acceptable carrier is suitable for oral administration and the composition comprises an oral dosage form.

Therapeutic or Prophylactic Uses

In one embodiment, the compounds or pharmaceutically acceptable salts of the compounds of the present invention are useful as GnRH receptor antagonists. Accordingly, the compounds and pharmaceutically acceptable salts of the compounds of the present invention are useful for treating a mammal with a GnRH-related disorder.

In one embodiment, the invention provides a method for treating a GnRH-related disorder, comprising administering to a mammal in need thereof a compound or a pharmaceutically acceptable salt of the compound of Formula (I) or Formula (II) in an amount effective to treat a GnRH-related disorder. In another embodiment, the compound or pharmaceutically acceptable salt of the compound is of the Formula (IA), (IB), (IC), or (ID).

In one embodiment, the GnRH-related disorder is a sex hormone-related condition.

In one embodiment, the GnRH-related disorder is a sex hormone-dependent cancer. In another embodiment, the GnRH-related disorder is prostate cancer, testicular cancer, uterine cancer, ovarian cancer, breast cancer, or pituitary gonadotrophe adenomas. In one embodiment, the GnRH-related disorder is breast cancer.

In another embodiment, the GnRH-related disorder is endometriosis, polycystic ovarian disease, uterine fibroids, primary hirsutism, luteinizing hormone surge, or precocious puberty.

In another embodiment, the invention provides a method for preventing pregnancy, comprising administering to a female mammal the compound or pharmaceutically acceptable salt of the compound of Formula (I) or Formula (II) in an amount effective to prevent pregnancy. In another embodiment, the compound or pharmaceutically acceptable salt of the compound is of the Formula (IA), (IB), (IC), or (ID).

In yet another embodiment, the methods of the present invention further comprise administering to the mammal a therapeutic agent selected from the group consisting of androgen, estrogen, progesterone, antiestrogen, antiprogestogen, testosterone, angiotensin-converting enzyme inhibitor, angiotensin II-receptor antagonist, renin inhibitor, bisphosphonate, growth hormone secretagogue, 5a-reductase 2 inhibitor, a 5a-reductase 1 inhibitor, a dual inhibitor of 5a-reductase 1 and 5a-reductase 2, antiandrogen, alpha-1 blockers, growth hormone, and luteinizing hormone releasing compound; or a combination thereof.

In one embodiment, the present invention is directed to a method for modulating the activity of a Gonadotropin Releasing Hormone receptor, comprising contacting the receptor with an effective amount of a compound or pharmaceutically acceptable salt of the compound of Formula (I) or Formula (II). In one embodiment, the method further comprises determining the activity of the receptor. In one embodiment, the step of determining the activity of the receptor is performed before the step of contacting the receptor with the compound or a pharmaceutically acceptable salt of the compound. In another embodiment, the step of determining the activity of the receptor is performed after the step of contacting the receptor with the compound or a pharmaceutically acceptable salt of the compound. In another embodiment, the compound or pharmaceutically acceptable salt of the compound is of the Formula (IA), (IB), (IC), or (ID).

The compounds and pharmaceutically acceptable salts of the compounds of Formula (I) or Formula (II) are also useful in the manufature of medicaments for treating a GnRH-related disorder in a mammal. In another embodiment, the compound or pharmaceutically acceptable salt of the compound is of the Formula (IA), (IB), (IC), or (ID).

Accordingly, in one embodiment, the invention provides the use of a compound or pharmaceutically acceptable salt of the compound of Formula (I) or Formula (II) for the manufacture of a medicament for treating a GnRH-related disorder.

In another embodiment, the compound or pharmaceutically acceptable salt of the compound is of the Formula (IA), (IB), (IC), or (ID).

In one embodiment, the GnRH-related disorder is a sex hormone-related condition.

In one embodiment, the GnRH-related disorder is a sex hormone-dependent cancer. In another embodiment, the GnRH-related disorder is prostate cancer, testicular cancer, uterine cancer, ovarian cancer, breast cancer, or pituitary gonadotrophe adenomas. In one embodiment, the GnRH-related disorder is breast cancer.

In another embodiment, the GnRH-related disorder is endometriosis, polycystic ovarian disease, uterine fibroids, primary hirsutism, luteinizing hormone surge, or precocious puberty.

In another embodiment, the invention provides the use of a compound or pharmaceutically acceptable salt of the compound of Formula (I) or Formula (II) in the manufacture of a medicament for preventing pregnancy in a female mammal. In another embodiment, the compound or pharmaceutically acceptable salt of the compound is of the Formula (IA), (IB), (IC), or (ID).

In yet another embodiment, the uses of the compounds or pharmaceutically acceptable salts of compounds of the present invention further comprise the use of a therapeutic agent selected from the group consisting of androgen, estrogen, progesterone, antiestrogen, antiprogestogen, testosterone, angiotensin-converting enzyme inhibitor, angiotensin II-receptor antagonist, renin inhibitor, bisphosphonate, growth hormone secretagogue, 5a-reductase 2 inhibitor, a 5a-reductase 1 inhibitor, a dual inhibitor of 5a-reductase 1 and 5a-reductase 2, antiandrogen, alpha-1 blockers, growth hormone, and luteinizing hormone releasing compound; or a combination thereof in the manufacture of the medicaments of the present invention.

In one embodiment, the present invention is directed to the use of a compound or pharmaceutically acceptable salt of the compound of Formula (I) or Formula (II) for the manufacture of a medicament for modulating the activity of a Gonadotropin Releasing Hormone receptor. In one embodiment, the medicament is also for determining the activity of the receptor. In another embodiment, the compound or pharmaceutically acceptable salt of the compound is of the Formula (IA), (IB), (IC), or (ID).

EXAMPLES

General Methods:

The following HPLC and LC/MS methods were used for the syntheses outlined in the Examples.

Method A: Column: Xterra MS C18, 5μ, 50×2.1 mm. Mobile phase: 90/10-5/95 water (0.1% formic acid)/acetonitrile (0.1% formic acid), 2 minutes, hold 1.5 minutes. Flow rate: 0.8 mL/min. Detection: 210-400 nm.

Method B: Column Xterra reverse phase 18, 3.5μ, 150×4.6 mm. Mobile phase: 85-15 to 5/95 ammonium formate buffer (pH=3.5)/acetonitrile and methanol (1:1) for 10 minutes, hold 4 minutes, 1.2 mL/minute. Detection: 210-370 nm.

Method C: Column Xterra reverse phase C18, 3.5μ, 150× 2.1 mm. Mobile phase: 78/22-5/95 phosphate buffer (pH=2.1) acetonitrile and methanol (1:1) for 10 minutes, hold 4 minutes, 1.2 mL/minute. Detection: 210-370 nm.

Method D: Column: Xterra reverse phase 18, 3.5μ, 150× 4.6 mm. Mobile phase: 85/15 to 5/95 phosphate buffer (pH=2.1)/acetonitrile and methanol (1:1) for 10 minutes, hold 4 minutes, 1.2 mL/minute. Detection: 210-370 nm.

Example 1

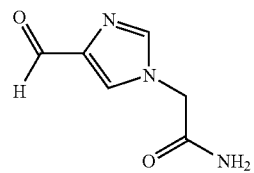

2-(4-Formyl-imidazol-1-yl)-acetamide: A solution of 1H-imidazole-4-carbaldehyde (1.92 g, 20 mmol) in anhydrous THF (32 mL) and DMF (8 mL) was treated with sodium hydride (60% dispersion in mineral oil, 880 mg, 22 mmol) for 5 mins. 2-Bromoacetamide (3.59 g, 26 mmol) was added and the reaction was stirred continuously overnight. The THF was concentrated, loaded on a silica column, and eluted with 20% methanol in dichloromethane. The solvent was evaporated to yield 2.70 g of the product as a white solid (88.2%). HPLC Method D, r.t.=1.5 min, (96.4% purity at 256 nm). LC/MS calculated mass=153.14, [M–H]⁻=152, [M+H]⁺=154.

Example 2

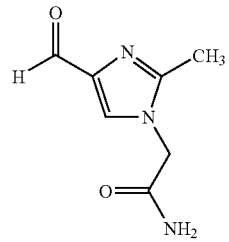

2-(4-Formyl-2-methyl-1H-imidazol-1-yl)acetamide: 2-(4-Formyl-2-methyl-1H-imidazol-1-yl)acetamide was prepared as set forth in Example 1, except that 2-methyl-1H-imidazole-4-carbaldehyde was used in place of 1H-imidazole-4-carbaldehyde. MS (ESI-POS): [M+H]⁺=168.

Example 3

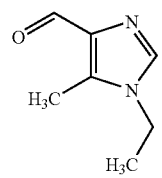

1-Ethyl-5-methyl-1H-imidazole-4-carbaldehyde: 5-Methyl-1H-imidazole-4-carbaldehyde (940 mg, 8.5 mmol) was dissolved in THF (40 ml) with DMF (5 ml). NaH (380 mg of a 60% dispersion in mineral oil) was added carefully and the reaction mixture was allowed to stir for 5 min. under nitrogen. Ethyl iodide (1.65 g, 9.7 mmol) was added and it was allowed to stir for 1 h, at which time the reaction was judged complete. The solvent was removed under vacuum, and the crude was purified on silica eluted with 100% ethyl acetate—1% MeOH/ethyl acetate to yield the title product (390 mg) as the main isomer. MS (ESI-POS): [M+H]$^+$=139.

Example 4

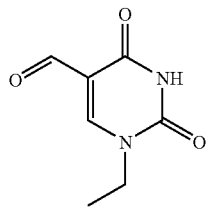

1-Ethyl-2,4-dioxo-1,2,3,4-tetrahydropyrimidine-5-carbaldehyde: A suspension of 5-formyluracil (0.84 g, 6.0 mmol) in anhydrous dimethylformamide (12 mL) under a nitrogen atmosphere was cooled to −40° C. The reaction mixture was treated with sodium hydride (60% mineral oil dispersion, 0.26 g, 6.6 mmol), stirred 30 min., then treated with iodoethane (0.53 mL, 6.6 mmol). The mixture warmed to 20° C. over 3 h., then was brought to 40° C. for 48 h. At this time the reaction mixture was cooled to room temperature, treated with methanol (5 mL) and evaporated to dryness under reduced pressure. The residue was purified by chromatography on silica gel eluted with a gradient of ethyl acetate in hexanes (1:3 to 1:2 to 1:1) to leave the product (0.25 g) as a white powder. MS (ESI-POS): [M+H]$^+$=169.

Example 5

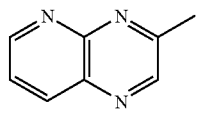

3-Methyl-pyrido[2,3-b]pyrazine: Pyridine-2,3-diamine (2.50 g, 22.9 mmol) was stirred in methanol (100 mL) and cooled in an ice bath and pyruvic aldehyde (40% wt., 4.20 mL, 27.5 mmol) was added, dropwise, and the solution was allowed to warm to room temperature and stirred, under nitrogen for 18 h. The solvent was removed in vacuo to give a black oil (4.23 g). This material was adsorbed onto silica gel and purified by column chromatography, eluting with a solution of 95:5 chloroform:acetone to afford a dark red solid (2.96 g, 89% Yield). HPLC Method B, 99.2% purity@210-370 nm, 99.8% @238 nM, r.t.=3.2 min. Calculated mass=145.06, [M+H]$^+$=146.

Example 6

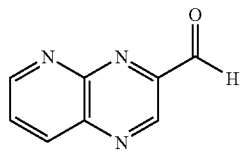

Pyrido[2,3-b]pyrazine-3-carbaldehyde: 3-Methyl-pyrido[2,3-b]pyrazine (1.00 g, 6.89 mmol) and selenium dioxane (800 mg, 7.2 mmol) were heated to reflux in 1,4-dioxane (70 mL) and distilled water (2 mL), under nitrogen, for 4 h. The reaction mixture was cooled to room temperature, allowed to stand for 16 h, filtered through diatomaceous earth, washed with ethyl acetate (50 mL) and the filtrate concentrated under reduced pressure. The residue was treated with dichloromethane (75 mL) and stirred for 30 mins. The DCM soluble portion was added to a column of silica gel and eluted with ethyl acetate to leave the product aldehyde as a light brown solid (254 mg). LC/MS Method A, r.t.=0.37 mins., purity=97.8%, calculated mass=159, [M+H]$^+$=160.

Example 7

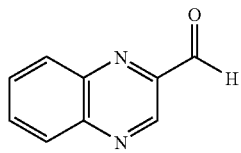

Quinoxaline-2-carbaldehyde: 2-Methyl-quinoxaline (1.00 mL, 7.75 mmol) and selenium dioxane (946 mg, 8.53 mmol) were heated to 90° C. (oil bath temperature) in 1,4-dioxane (6 mL) and distilled water (4 mL), under nitrogen, for 18 h. The solvent was removed in vacuo, and the material dissolved in ethyl acetate (100 mL) and solid selenium precipitate formed and was filtered out of solution. The organic phase was washed with saturated sodium bicarbonate solution (3×100 mL). The bicarbonate washings were combined and extracted with ethyl acetate (2×100 mL). The organic extracts were combined and washed with brine (150 mL), dried (MgSO$_4$), filtered and the solvent removed in vacuo to give a red solid (440 mg). This material was adsorbed onto silica gel and purified by column chromatography, eluting with a solution of 4:1 hexane:ethyl acetate to afford a tan solid (180 mg, 15% Yield). $^1$H NMR 300 MHz (DMSO): δ=0.20 (s, 1H), 9.40 (s, 1H), 8.35 (dd, 1H, J=7.9 Hz, J=1.5 Hz), 8.25 (dd, 1H, J=7.7 Hz, J=1.1 Hz), 8.08 (m, 2H).

Example 8

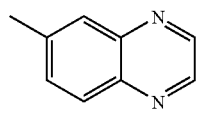

6-Methylquinoxaline: A solution of 4-methyl-1,2-phenylenediamine (5.0 g, 41 mmol) in methanol (250 mL) was treated with a solution of 40% aqueous glyoxal and stirred for 16 h. The solvent was evaporated and the residue was distilled under vacuum (2 mm Hg, 85-88° C.) to leave a colorless oil (1.5 g, 25%). LC/MS Method A, r.t.=1.02 mins., purity=99.5%.

Example 9

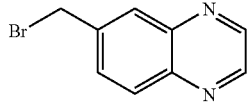

6-Bromomethylquinoxaline: A mixture of 6-methylquinoxaline (1.5 g, 10.4 mmol), N-bromosuccinimide (2.2 g, 12.5 mmol) and benzoylperoxide (0.30 g, 1.25 mmol) in benzene (35 mL) was stirred rapidly and heated to reflux for 5 h. Upon cooling the mixture was diluted with ethyl acetate (25 mL), washed with 1N sodium hydroxide solution (50 mL) and saturated sodium chloride solution (50 mL). The organic layer was dried (MgSO$_4$) and evaporated to a crystalline solid (2.5 g, 77% desired product, 23% α,α-dibrominated product as determined by $^1$H NMR). The mixture was used in subsequent reactions.

Example 10

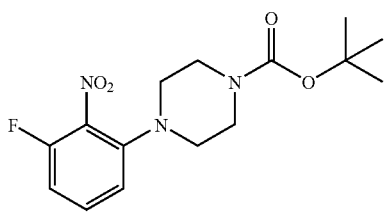

4-(3-Fluoro-2-nitro-phenyl)-piperazine-1-carboxylic acid tert-butyl ester: To a solution of 1,3-difluoro-2-nitro-benzene (10 g, 62.9 mmol), ethyldiisopropylamine (27 mL, 157 mmol), in anhydrous DMSO (40 mL) was added piperazine-1-carboxylic acid tert-butyl ester (13.3 g, 69.1 mmol) and the solution stirred at room temperature, under nitrogen, for 18 h. The reaction was transferred to a separatory funnel with ethyl acetate (100 mL) and washed with distilled water (100 mL×3). The aqueous washings were combined and extracted with ethyl acetate (100 mL×2). The organic extracts were combined, washed with 1M aqueous citric acid solution (150 mL×2), saturated aqueous sodium bicarbonate solution (150 mL), brine (150 mL), decolorizing carbon and filtered. The filtrate was dried with anhydrous sodium sulfate, filtered and the solvent removed in vacuo to give a black liquid which solidified upon standing to give a dark yellow tinted crystalline solid (18.5 g). This material was adsorbed onto silica and purified by column chromatography, eluting with a solution of 33% ethyl acetate in hexane to afford an orange crystalline solid (13.9 g, 68%). Mass Spectrum (+ESI): 226 [M+H-Boc]$^+$

Example 11

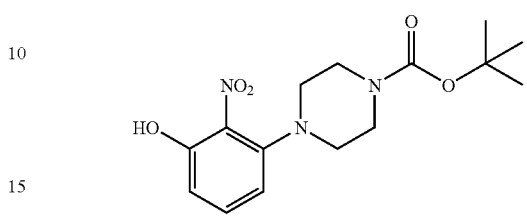

4-(3-Hydroxy-2-nitro-phenyl)-piperazine-1-carboxylic acid tert-butyl ester: To a cooled stirring solution of 4-(3-fluoro-2-nitro-phenyl)-piperazine-1-carboxylic acid tert-butyl ester (1.50 g, 4.61 mmol), and 2-(methylsulfonyl)ethanol (876 mg, 6.92 mmol) in anhydrous DMF (15 mL), under nitrogen, was added, portionwise, sodium hydride (553 mg, 13.8 mmol, 60% oil dispersion). The solution foamed upon the sodium hydride addition. The resulting dark orange solution was stirred, at 0° C., for 30 minutes upon completion of sodium hydride addition. The reaction solution became viscous and additional DMF (5 mL) was added, via syringe, the ice bath removed and the dark solution stirred at room temperature, under nitrogen, for 2 h. The reaction was cooled in an ice bath, quenched with 0.1N hydrochloric acid solution, and transferred to a separatory funnel with ethyl acetate (100 mL). This organic phase was washed with brine (75 mL×3). The aqueous washings were combined and extracted with ethyl acetate (75 mL×3). The organic extracts were combined and washed with saturated aqueous sodium bicarbonate solution (100 mL), brine (100 mL), dried with anhydrous sodium sulfate, filtered and the solvent removed to give an amber colored oil (2.21 g). This oil was adsorbed onto silica and purified by column chromatography, eluting with 50% ethyl acetate in hexane to afford the product as a light yellow colored solid (1.37 g, 92%). Mass Spectrum (+ESI): 324 [M+H]$^+$, 322 [M−H]$^−$.

Example 12

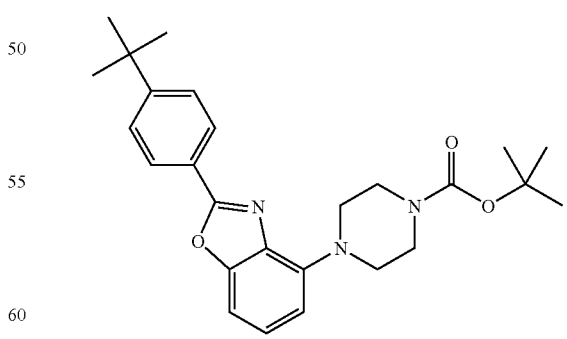

4-[2-(4-tert-Butyl-phenyl)-benzooxazol-4-yl]-piperazine-1-carboxylic acid tert-butyl ester: 4-(3-hydroxy-2-nitro-phenyl)-piperazine-1-carboxylic acid tert-butyl ester (1.00 g, 3.09 mmol) was charged to a 250 mL round bottom flask containing 10% Pd/C, stir bar and septum. Under a positive stream of N$_2$, 2-propanol (80 mL) was added via syringe. The flask was evacuated and fitted with a balloon containing H$_2$ and stirred, under H$_2$, at room temperature for 18 h. LC-MS indicated only aniline present. 4-tert-Butyl-benzaldehyde (800 μL, 4.64 mmol) was added, the balloon was replaced with an air condenser and the stirring solution was heated to 80° C. for 48 h. The reaction was cooled to room temperature and filtered through celite to remove the catalyst and the solvent removed in vacuo to give a brown oil. This oil was adsorbed onto silica and purified by column chromatography, eluting with 11% ethyl acetate in hexane to afford the product as a clear waxy material (1.09 g, 81%). Mass Spectrum (+ESI): 436 [M+H]$^+$.

Example 13

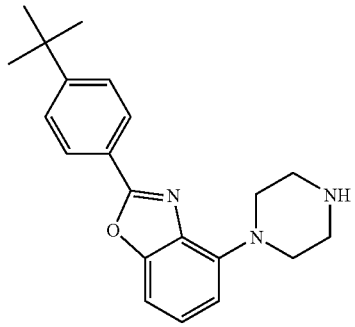

2-(4-tert-Butyl-phenyl)-4-piperazin-1-yl-benzooxazole: 4-[2-(4-tert-butyl-phenyl)-benzooxazol-4-yl]-piperazine-1-carboxylic acid tert-butyl ester (900 mg, 2.07 mmol) was stirred in a solution of concentrated trifluoroacetic acid (20 mL) and methylene chloride (20 mL) under N$_2$ at room temperature for 5 h. The solvent was removed in vacuo and the oil was transferred to a separatory funnel with ethyl acetate (150 mL) and washed with 1M aqueous potassium carbonate solution (100 mL×2). The aqueous washings were combined and extracted with ethyl acetate (150 mL). The organic extracts were combined and washed with brine (100 mL), dried (Na$_2$SO$_4$), filtered and the filtrate concentrated to give a clear oil which was concentrated in vacuo with hexane several times to give a waxy material which was placed on a drying pistol overnight to afford the product as an amber colored wax (550 mg, 79%). Mass Spectrum (+ESI): 336 [M+H]$^+$.

Example 14

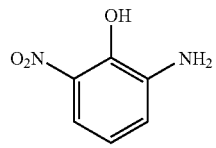

2-Amino-6-nitro phenol: Ref.: WO 96/11917. A slurry of 2,6-dinitro phenol (20% in H$_2$O, 5 g, 0.0271 mol), NH$_4$Cl (14.30 g, 0.267 mol), and ammonium hydroxide solution (3 mL) was heated in a 70° C. bath. A warm solution of Na$_2$S-9H$_2$O (24.19 g, 0.1 mol) in H$_2$O (23 mL) was added to the slurry and the resulting orange suspension was heated with stirring for 3 h, then allowed to cool to room temperature. The mixture was cooled in an ice bath and slowly acidified with 6 N HCl to pH 2. The mixture was filtered and the filtrate was extracted with CHCl$_3$ (3×75 mL). The combined organic extracts were concentrated in vacuo and the crude material was adsorbed onto silica gel. Purification by silica gel chromatography, eluting with 25% hexane/CH$_2$Cl$_2$ then CH$_2$Cl$_2$, afforded the title compound (1.47 g) as a brick red powder. MS (ESI-POS): [M+H]$^+$=155.

Example 15

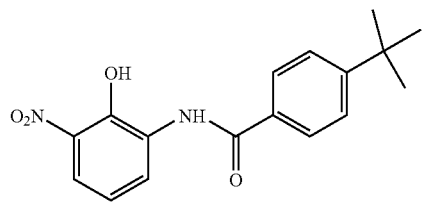

4-tert-butyl-N-(2-hydroxy-3-nitrophenyl)benzamide: Ref.: WO 96/11917. To a solution of 4-tert-butyl benzoic acid (0.81 g, 4.57 mmol) in CH$_2$Cl$_2$ (10 mL) cooled in an ice bath was added 1,1'-carbonyldiimidazole (0.94 g, 5.80 mmol). The solution was stirred for 5 min., then the bath was removed and the reaction was stirred at room temperature for 1.5 h. To a solution of 2-amino-6-nitro phenol (0.829 g, 5.38 mmol) in CH$_2$Cl$_2$ (40 mL) cooled in an ice bath was added the activated acid solution dropwise. The reaction was allowed to stir and gradually come to room temperature overnight. To the solution was added CH$_2$Cl$_2$ (50 mL) and H$_2$O (25 mL) and the layers were separated. The aqueous layer was extracted with CH$_2$Cl$_2$ (2×30 mL). The combined organic layers were washed with H$_2$O (25 mL), 1 N HCl (25 mL), and brine (25 mL), dried (Na$_2$SO$_4$), filtered, and concentrated under reduced pressure. The crude material was adsorbed onto silica gel and purified by silica gel chromatography, eluting with 66% CH$_2$Cl$_2$/hexane to 75% CH$_2$Cl$_2$/hexane to afford the title compound (0.579 g) as a golden solid. MS (ESI-POS): [M+H]$^+$=315; Anal. Calc'd for C$_{17}$H$_{18}$N$_2$O$_4$: C, 64.96; H, 5.77; N, 8.91. Found: C, 64.98; H, 5.78; N, 8.89.

Example 16

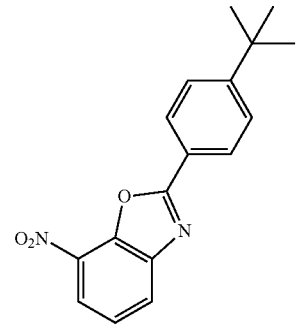

2-(4-tert-butylphenyl)-7-nitro-1,3-benzooxazole: A solution of 4-tert-butyl-N-(2-hydroxy-3-nitrophenyl)benzamide (0.35 g, 1.11 mmol) and pyridinium p-toluenesulfonate (200 mg, 0.8 mmol) in xylenes (25 mL) was heated in a 135° C. bath for 72 h. The solution was cooled to room temperature, and $CH_2Cl_2$ (100 mL) and $H_2O$ (25 mL) were added. The layers were separated, and the aqueous layer was extracted with $CH_2Cl_2$ (50 mL). The combined organic layers were washed with brine (25 mL), dried ($Na_2SO_4$), filtered, and concentrated under reduced pressure to afford the title compound (0.260 g) as a golden solid. MS (ESI-POS): $[M+H]^+$= 297; Anal. Calcd for $C_{17}H_{16}N_2O_3$: C, 68.91; H, 5.44; N, 9.45. Found: C, 69.02; H, 5.43; N, 9.00.

Example 17

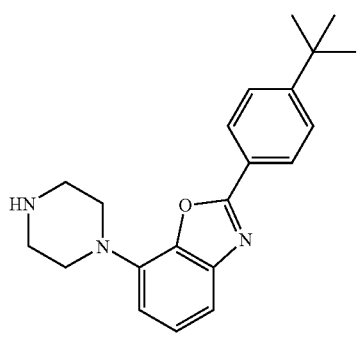

2-(4-tert-butylphenyl)-7-piperazin-1-yl-1,3-benzooxazole: A solution of 2-(4-tert-butylphenyl)-7-nitro-1,3-benzooxazole (1.272 g, 4.29 mmol) in isopropanol (30 mL) and EtOAc (40 mL) was reduced over a catalytic amount of 5% Pd/C under a balloon of hydrogen over 4 h. The reaction mixture was filtered through diatomaceous earth on a fritted funnel. The filtrate was concentrated in vacuo to afford a golden oil (1.03 g), which was dissolved in chlorobenzene (20 mL) and n-butanol (20 mL). To the solution was added $K_2CO_3$ (0.588 g, 4.25 mmol) and bis (2-chloroethyl)amine hydrochloride (0.69 g, 3.86 mmol) and the mixture was heated in a 130° C. bath overnight. Additional $K_2CO_3$ (0.588 g, 4.25 mmol) and bis(2-chloroethyl)amine hydrochloride (0.69 g, 3.86 mmol) were added and the reaction was heated for another 6 h. The reaction was cooled to room temperature and concentrated in vacuo. To the residue was added 1 N NaOH (25 mL) and EtOAc (100 mL), and the layers were separated. The aqueous layer was extracted with EtOAc (2×60 mL). The combined organic layers were dried ($Na_2SO_4$), filtered, and concentrated under reduced pressure to afford a dark oil which was adsorbed onto silica gel. Silica gel chromatography from 5% $MeOH/CH_2Cl_2$ then 60% $MeOH/CH_2Cl_2$ provided a brown foam on concentration of polar fractions. The material was purified on RP HPLC (10% to 100% $CH_3CN/H_2O$) and the product fractions were concentrated. To the aqueous residue was added 1 N NaOH (10 mL) and $CH_2Cl_2$ (75 mL) and the layers were separated. The aqueous layer was extracted with $CH_2Cl_2$ (3×25 mL). The combined organic layers were washed with brine (15 mL), dried ($Na_2SO_4$), filtered, and concentrated under reduced pressure to afford the title compound (135 mg) as a gummy solid. MS (ESI-POS): $[M+H]^+$=336.

Example 18

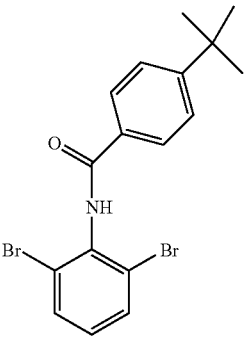

4-tert-butyl-N-(2,6-dibromophenyl)benzamide: 2,6-Dibromoaniline (1.0 g, 3.98 mmol) was dissolved in dioxane (20 mL) and treated with diisopropylethylamine (1.39 mL, 7.96 mmol) followed by 4-tert-Butylbenzoyl chloride (1.70 g, 7.96 mmol). The solution was warmed to 60° C. and stirred overnight. The mixture was concentrated under reduced pressure and the residue was re-dissolved in ethyl acetate (50 mL). The organic solution was washed with 10% HCl (2×50 mL), saturated sodium carbonate (50 mL) and saturated sodium chloride (50 mL). The organic layer was dried (magnesium sulfate), filtered, and concentrated under reduced pressure. The residue was purified by flash silica gel chromatography, eluting with 20% acetone/hexane to yield 1.33 g (81%) of product. MS (ESI) m/z 409.9772; HPLC Method B, purity 92.3% at 210-370 nm, 10.4 min.; 89.7% at 232 nm, 10.4 min.; HRMS: calcd for $C_{17}H_{17}Br_2NO+H+$, 409.97496; found (ESI, $[M+H]^+$), 409.9772.

Example 19

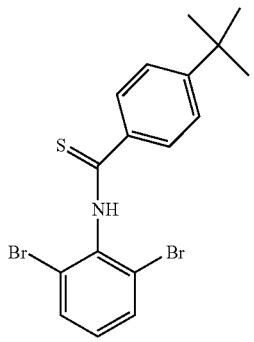

4-tert-butyl-N-(2,6-dibromophenyl)benzenecarbothioamide: 4-tert-butyl-N-(2,6-dibromophenyl)benzamide prepared as in Example 18 (1.20 g, 2.92 mmol) was dissolved in toluene (45 mL) and treated with Lawesson's reagent (1.18 g, 2.92 mmol.) The solution was heated to reflux for 2 h and then cooled. The solvent was removed under reduced pressure, and the residue was adsorbed onto silica gel. Elution with 10% to 20% acetone/hexane gave 0.509 g (41%) of product. MS (ESI) m/z 425.952; HPLC Method B, purity 85.7% at 210-370 nm, 11.1 min.; 91.1% at 262 nm, 11.1 min.; HRMS: calcd for $C_{17}H_{17}Br_2NS+H+$, 425.95212; found (ESI, [M+H]⁺), 425.952.

Example 20

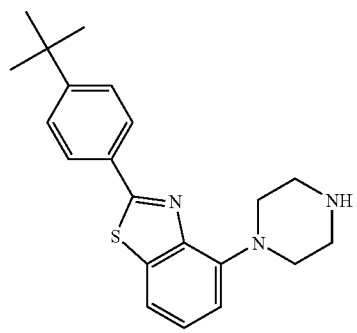

2-(4-tert-butylphenyl)-4-piperazin-1-yl-1,3-benzothiazole: 4-tert-butyl-N-(2,6-dibromophenyl)benzenecarbothioamide prepared as in Example 19 (0.200 g, 0.468 mmol) was dissolved in dioxane (4 mL) and treated with $Pd_2 dba_3$ (4.3 mg, 0.0468 mmol), o-biphenyl(tBu)₂P (15.4 mg, 0.0515 mmol) and $Cs_2CO_3$ (0.229 g, 0.702 mmol). The mixture was heated to 80° C. for 2 h until the starting material was consumed and cooled. To the reaction mixture was then added toluene (2 mL), $Pd_2 dba_3$ (4.3 mg, 0.0468 mmol), o-biphenyl (tBu)₂P (15.4 mg, 0.0515 mmol), sodium tert-butoxide (0.090 g, 0.936 mmol) and piperazine (0.403 g, 4.68 mmol). The mixture was heated at 80° C. for 1 h and filtered through celite. The filtrate was diluted with dichloromethane, washed with water and saturated sodium chloride, and concentrated. The crude material was purified by reverse-phase HPLC to yield 69.5 mg (42%) of the product. MS (ES) m/z 352.1; HPLC Method B, purity 100% at 210-370 nm, 9.8 min.; 99.4% at 310 nm, 9.8 min.; HRMS: calcd for $C_{21}H_{25}N_3S+H+$, 352.18419; found (ESI, [M+H]⁺), 352.1841.

Example 21

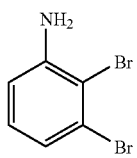

2,3-dibromoaniline: Ref: *J. Org. Chem.* 1990, 55(9) 2736-2742; *Tetrahedron Lett.*, 1984, 25, 839-42. 1,2-Dibromobenzene (5.0 g, 21.2 mmol) was cooled in an ice bath and treated dropwise with fuming nitric acid (9.75 mL). The mixture was stirred vigorously for 15 minutes and then pipetted portionwise into a flask of crushed ice. The pale yellow solid was removed by filtration, washed with water and air dried to yield 7.613 g of a mixture of regioisomers. The crude material (0.666 g, 2.37 mmol) was dissolved in ethanol (14 mL) and treated with tin(II) chloride hydrate. The solution was refluxed for 1 h and poured into ice water and the pH was adjusted to 9 with 2N NaOH. The mixture was extracted with ether (2×25 mL). The organic extracts were washed with saturated sodium chloride, dried over magnesium sulfate, filtered and concentrated under reduced pressure to yield 0.544 g of crude material as a mixture of regioisomers. The material was dry-mounted on silica gel and flash chromatographed using 10% to 20% ether/hexane to elute the minor product (higher $R_f$ component) as white solid (0.082 g, 13.7%) ES+: 249.8 (M+H)⁺; HRMS: 249.8876 (M+H)+.

Example 22

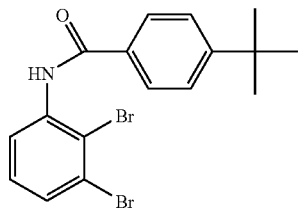

4-tert-butyl-N-(2,3-dibromophenyl)benzamide: The amide was prepared according to Example 18 from 2,3-dibromoaniline, 4-tert-butylbenzoyl chloride and diisopropylethylamine in dioxane. MS (ESI) m/z 408; HPLC Method B, purity 80.6% at 210-370 nm, 11.4 min.; 74.9% at 240 nm, 11.4 min.; HRMS: calcd for $C_{17}H_{17}Br_2NO+H+$, 409.97496; found (ESI, [M+H]⁺), 409.9775.

Example 23

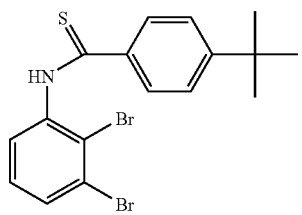

4-tert-butyl-N-(2,3-dibromophenyl)benzenecarbothioamide: The thioamide was prepared according to Example 19 using the 4-tert-butyl-N-(2,3-dibromophenyl)benzamide of Example 22, and Lawesson's reagent in toluene. MS (ESI) m/z 426; HPLC Method B, purity 96.3% at 210-370 nm, 11.4 min.; 98.3% at 262 nm, 11.4 min.; HRMS: calcd for $C_{17}H_{17}Br_2NS+H+$, 425.95212; found (ESI, [M+H]⁺), 425.9527.

Example 24

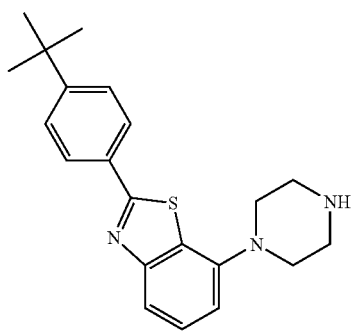

2-(4-tert-Butylphenyl)-7-piperazin-1-yl-1,3-benzothiazole: The piperazine template was prepared according to Example 20 from the 4-tert-butyl-N-(2,3-dibromophenyl)benzenecarbothioamide of Example 23. MS (ESI) m/z 352; HPLC Method B, purity 95.7% at 210-370 nm, 9.2 min.; 97.3% at 304 nm, 9.2 min.; HRMS: calcd for $C_{21}H_{25}N_3S$+ H+, 352.18419; found (ESI, [M+H]$^+$), 352.1839.

Example 25

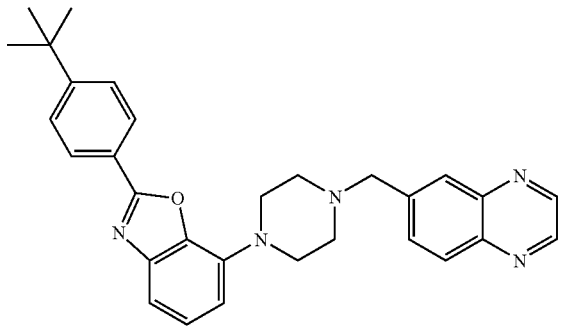

6-({4-[2-(4-tert-butylphenyl)-1,3-benzoxazol-7-yl]piperazin-1-yl}methyl)quinoxaline: To a suspension of 2-(4-tert-butylphenyl)-7-piperazin-1-yl-1,3-benzooxazole 23.5 mg, 0.070 mmol) and 6-bromomethylquinoxaline (17.2 mg, 0.077 mmol) in CH$_3$CN (anh., 10 mL) was added ethyldiisopropylamine (0.015 mL, 0.084 mmol). The mixture was heated in a 95° C. bath overnight. The reaction was cooled to room temperature and concentrated in vacuo. The residue was adsorbed onto silica gel. Silica gel chromatography using a gradient of 25% EtOAc/hexane to 50% EtOAc/hexane then 100% EtOAc afforded the title compound (23.2 mg) as an ivory powder. MS (ESI) m/z 478 [M+H]+; HPLC Method C, r.t.=10.9 min (98.9% @210-370 nm; 97.4% @ 236 nm).

Example 26

The following compounds were prepared according to the procedure of Example 25.

| Example | Name | [M + H]$^+$ |
|---|---|---|
| 26-A | 6-{4-[2-(4-tert-Butyl-phenyl)-benzooxazol-4-yl]-piperazin-1-ylmethyl}-quinoxaline | 478 |
| 26-B | 6-{4-[2-(4-tert-Butyl-phenyl)-benzothiazol-4-yl]-piperazin-1-ylmethyl}-quinoxaline | 494 |
| 26-C | 6-{4-[2-(4-tert-Butyl-phenyl)-benzothiazol-7-yl]-piperazin-1-ylmethyl}-quinoxaline | 494 |

Example 27

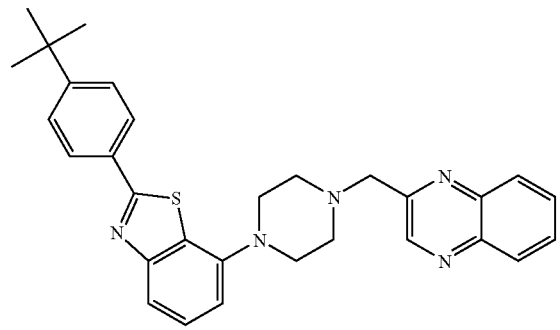

2-({4-[2-(4-tert-butylphenyl)-1,3-benzothiazol-7-yl]piperazin-1-yl}methyl) quinoxaline: The piperazine template (0.075 g, 0.213 mmol) of Example 24 was dissolved in 1,2-dichloroethane (3 mL) and treated with quinoxaline-2-carbaldehyde (0.044 g, 0.277 mmol) and glacial acetic acid (2 drops). Sodium triacetoxyborohydride (0.090 g, 0.426 mmol) was added, and the mixture was stirred at room temperature until the reaction was complete by LCMS analysis. The solvent was removed under reduced pressure, and the resulting residue was purified by RP-HPLC to yield the free base (0.0578 g, 55% yield). MS (ESI) m/z 494.

Example 28

The following compounds were prepared according to the procedure set forth in Example 27.

| Example | Name | [M + H]$^+$ |
|---|---|---|
| 28-A | 2-(4-{4-[2-(4-tert-Butyl-phenyl)-benzooxazol-4-yl]-piperazin-1-ylmethyl}-imidazol-1-yl)-acetamide | 473 |
| 28-B | 2-(4-tert-Butyl-phenyl)-4-[4-(2-ethyl-5-methyl-1H-imidazol-4-ylmethyl)-piperazin-1-yl]-benzooxazole | 458 |
| 28-C | 2-(4-{4-[2-(4-tert-Butyl-phenyl)-benzooxazol-4-yl]-piperazin-1-ylmethyl}-2-methyl-imidazol-1-yl)-acetamide | 487 |
| 28-D | 2-(4-{4-[2-(4-tert-Butyl-phenyl)-benzooxazol-7-yl]-piperazin-1-ylmethyl}-imidazol-1-yl)-acetamide | 473 |
| 28-E | 2-(4-{4-[2-(4-tert-Butyl-phenyl)-benzooxazol-7-yl]-piperazin-1-ylmethyl}-2-methyl-imidazol-1-yl)-acetamide | 487 |

-continued

| Example | Name | [M + H]⁺ |
|---|---|---|
| 28-F | 2-(4-tert-Butyl-phenyl)-7-[4-(2-ethyl-5-methyl-1H-imidazol-4-ylmethyl)-piperazin-1-yl]-benzooxazole | 458 |
| 28-G | 5-{4-[2-(4-tert-Butyl-phenyl)-benzothiazol-4-yl]-piperazin-1-ylmethyl}-1-ethyl-1H-pyrimidine-2,4-dione | 504 |
| 28-H | 5-{4-[2-(4-tert-Butyl-phenyl)-benzothiazol-4-yl]-piperazin-1-ylmethyl}-1H-pyrimidine-2,4-dione | 476 |
| 28-I | 2-(4-tert-Butyl-phenyl)-4-[4-(2-ethyl-5-methyl-1H-imidazol-4-ylmethyl)-piperazin-1-yl]-benzothiazole | 474 |
| 28-J | 2-(4-tert-Butyl-phenyl)-4-[4-(1-ethyl-5-methyl-1H-imidazol-4-ylmethyl)-piperazin-1-yl]-benzothiazole | 474 |
| 28-K | 3-{4-[2-(4-tert-Butyl-phenyl)-benzothiazol-4-yl]-piperazin-1-ylmethyl}-pyrido[2,3-b]pyrazine | 495 |
| 28-L | 2-{4-[2-(4-tert-Butyl-phenyl)-benzothiazol-4-yl]-piperazin-1-ylmethyl}-quinoxaline | 494 |
| 28-M | 3-{4-[2-(4-tert-Butyl-phenyl)-benzothiazol-7-yl]-piperazin-1-ylmethyl}-pyrido[2,3-b]pyrazine | 495 |
| 28-N | 2-(4-tert-Butyl-phenyl)-7-[4-(2-ethyl-5-methyl-1H-imidazol-4-ylmethyl)-piperazin-1-yl]-benzothiazole | 474 |
| 28-O | 2-(4-tert-Butyl-phenyl)-7-[4-(1-ethyl-5-methyl-1H-imidazol-4-ylmethyl)-piperazin-1-yl]-benzothiazole | 474 |
| 28-P | 5-{4-[2-(4-tert-Butyl-phenyl)-benzothiazol-7-yl]-piperazin-1-ylmethyl}-1-ethyl-1H-pyrimidine-2,4-dione | 504 |
| 28-Q | 5-{4-[2-(4-tert-Butyl-phenyl)-benzothiazol-7-yl]-piperazin-1-ylmethyl}-1H-pyrimidine-2,4-dione | 476 |

Example 29

Biological Evaluation

COS cell membranes containing human GnRH receptors were incubated with radioactively labeled D-trp6 GnRH in the presence of increasing concentrations of test compound. Membrane bound radioactivity was measured after separating the free radioactivity by filtration method, and $IC_{50}$ values were calculated using SAS analysis system. (See, "Receptor-binding Affinity of Gonadotropin-releasing Hormone Analogs: Analysis by Radioligand-receptor assay" *Endocrinology*, 106:1154-1159 (1980)).

All compounds tested had hGnRH binding $IC_{50}$'s between 25 nm and 100 µM.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound of the formula (I):

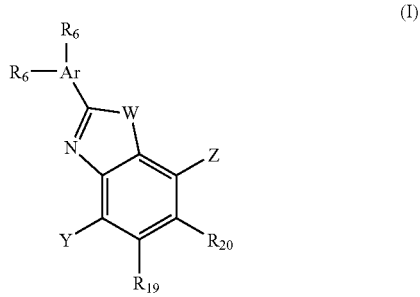

or a pharmaceutically acceptable salt thereof, wherein
W is O or S;
Y is Q and Z is $R_{18}$; or Y is $R_{18}$ and Z is Q, wherein Q is

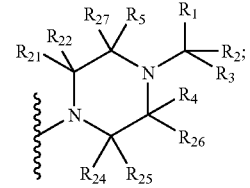

Ar is phenyl, 2-thiophenyl or 3-thiophenyl;

$R_1$ and $R_2$ are each independently hydrogen; or linear or branched $(C_1-C_6)$-alkyl, $(C_2-C_6)$-alkenyl, or $(C_2-C_6)$-alkynyl, each optionally substituted with halogen, $—N_3$, $—NO_2$, $—CN$, $—OR_{23}$, $—SR_{23}$, $—SO_2R_{23}$, $—SO_2N(R_{23})_2$, $—N(R_{23})_2$, $—COR_{23}$, $—CO_2R_{23}$, $—NR_{23}CO_2R_{23}$, $—NR_{23}COR_{23}$, $—NR_{23}CON(R_{23})_2$, or $—CON(R_{23})_2$; or $R_1$ and $R_2$ may together form a three- to seven-membered cycloalkyl group, wherein the cycloalkyl group formed by $R_1$ and $R_2$ is optionally substituted with halogen, $—N_3$, $—NO_2$, $—CN$, $—OR_{23}$, $—SR_{23}$, $—SO_2R_{23}$, $—SO_2N(R_{23})_2$, $—N(R_{23})_2$, $—COR_{23}$, $—CO_2R_{23}$, $—NR_{23}CO_2R_{23}$, $—NR_{23}COR_{23}$, $—NR_{23}CON(R_{23})_2$, $—CON(R_{23})_2$, or $—(CH_2)_nOR_{23}$;

$R_3$ is one of the following:

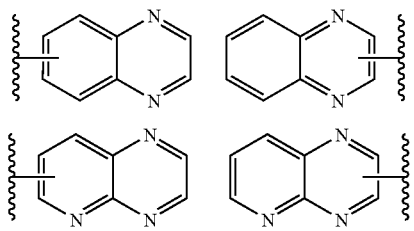

-continued

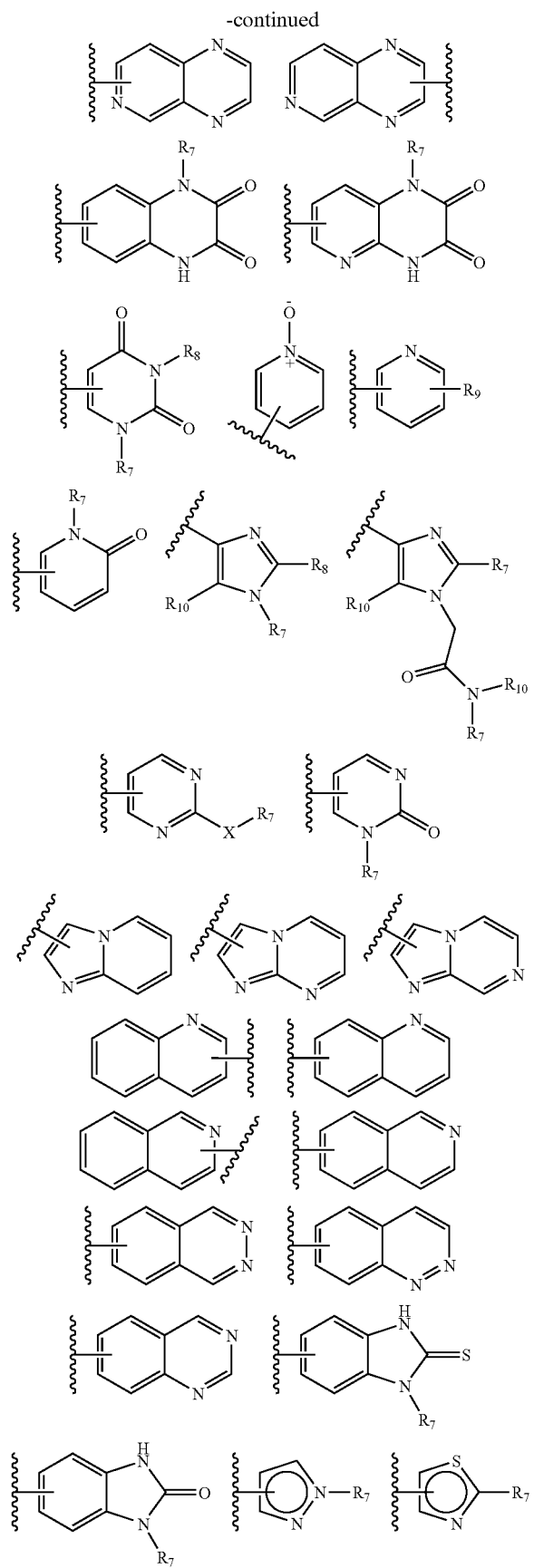
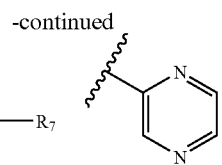

each $R_3$ also having up to three $R_{10}$ substituents attached to the ring of $R_3$ containing at least one N;

$R_4$, $R_5$, $R_{10}$, $R_{21}$, $R_{22}$, $R_{23}$, $R_{24}$, $R_{25}$, $R_{26}$, and $R_{27}$ are each independently hydrogen; or linear or branched ($C_1$-$C_6$)-alkyl, ($C_2$-$C_6$)-alkenyl, or ($C_2$-$C_6$)-alkynyl;

each $R_6$ is independently hydrogen; linear or branched ($C_1$-$C_6$)-alkyl, ($C_2$-$C_6$)-alkenyl, or ($C_2$-$C_6$)-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; —$NR_{13}R_{14}$; —C(OH)($CF_3$)$_2$; —CH($CF_3$)$_2$; —C($CF_3$)$_3$—$XR_{13}$; or —$COR_{13}$; and when the two $R_6$ are ortho to each other, they may together form a five- to seven-membered cyclic group containing up to 3 heteroatoms selected from N, O, or S, and wherein the cyclic group formed by the ortho $R_6$ groups is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_7$ and $R_9$ are each independently hydrogen; linear or branched ($C_1$-$C_6$)-alkyl, ($C_2$-$C_6$)-alkenyl, or ($C_2$-$C_6$)-alkynyl; —$(CH_2)_nXR_{12}$; —$(CH_2)_nR_{17}$; —$COXR_{11}$; —$XR_{11}$; —$CO_2R_{11}$; or —$CONR_{11}R_{12}$;

$R_8$ is hydrogen; linear or branched ($C_1$-$C_6$)-alkyl, ($C_2$-$C_6$)-alkenyl, or ($C_2$-$C_6$)-alkynyl; —$(CH_2)_mCO_2R_{11}$; or —$(CH_2)_mCONR_{11}R_{12}$;

$R_{11}$ and $R_{12}$ are each independently hydrogen; linear or branched ($C_1$-$C_6$)-alkyl, ($C_2$-$C_6$)-alkenyl, or ($C_2$-$C_6$)-alkynyl; or $R_{11}$ and $R_{12}$ may together form a three- to seven-membered heterocyclic group containing up to 3 heteroatoms selected from N, O, or S;

$R_{13}$ and $R_{14}$ are each independently hydrogen; linear or branched ($C_1$-$C_6$)-alkyl, ($C_2$-$C_6$)-alkenyl, or ($C_2$-$C_6$)-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$R_{23}CO_2R_{23}$, —$NR_{23}COR_{23}$, —$NR_{23}CON(R_{23})_2$, or —$CON(R_{23})_2$; aryl; or aryl optionally substituted with one to three substituents selected from halogen, $R_{15}$, —$OR_{15}$, or —$NR_{15}R_{16}$; or $R_{13}$ and $R_{14}$ may together form a three- to seven-membered heterocyclic group containing up to 3 heteroatoms selected from N, O, or S, and wherein the heterocyclic group formed by $R_{13}$ and $R_{14}$ is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_{15}$ and $R_{16}$ are each independently hydrogen; or linear or branched ($C_1$-$C_6$)-alkyl, ($C_2$-$C_6$)-alkenyl, or ($C_2$-$C_6$)-alkynyl; or both $R_{15}$ and $R_{16}$ may together form a three- to seven-membered heterocyclic group containing up to 3 heteroatoms selected from N, O, or S;

$R_{17}$ is phenyl, 2-pyridyl, 3-pyridyl, or 4-pyridyl;

$R_{18}$, $R_{19}$, and $R_{20}$ are each independently hydrogen; linear or branched ($C_1$-$C_6$)-alkyl, ($C_2$-$C_6$)-alkenyl, or ($C_2$-$C_6$)-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; halogen; —$NR_{13}R_{14}$; —C(OH)($CF_3$)$_2$; —CH($CF_3$)$_2$; —C($CF_3$)$_3$; —$XR_{13}$; —$COR_{13}$; —$CO_2R_{13}$; or —$CON(R_{13})(R_{14})$;

X is —O—, —$NR_{12}$—, or —$SO_m$—;

each m is independently 0, 1, or 2; and each n is independently 0, 1, 2, 3, or 4.

2. The compound of claim 1 of the formula (IA):

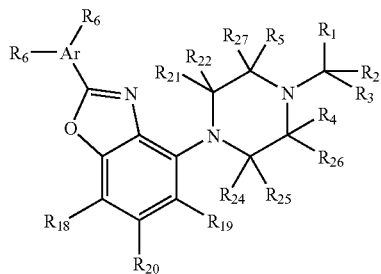

(IA)

or a pharmaceutically acceptable salt thereof, wherein Ar, $R_1$, $R_2$, $R_3$, $R_4$, $R_5$, $R_6$, $R_{18}$, $R_{19}$, $R_{20}$, $R_{21}$, $R_{22}$, $R_{24}$, $R_{25}$, $R_{26}$, and $R_{27}$ are as in claim 1.

3. The compound of claim 1 of the formula (IB):

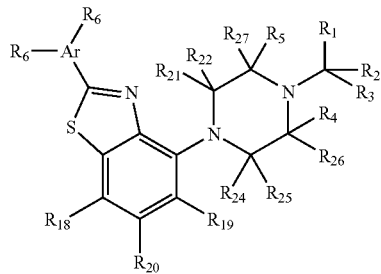

(IB)

or a pharmaceutically acceptable salt thereof, wherein Ar, $R_1$, $R_2$, $R_3$, $R_4$, $R_5$, $R_6$, $R_{18}$, $R_{19}$, $R_{20}$, $R_{21}$, $R_{22}$, $R_{24}$, $R_{25}$, $R_{26}$, and $R_{27}$ are as in claim 1.

4. The compound or pharmaceutically acceptable salt of the compound of claim 1, wherein Ar is phenyl.

5. The compound or pharmaceutically acceptable salt of the compound of claim 4, wherein one $R_6$ substituent is attached at the 4 position of phenyl.

6. The compound or pharmaceutically acceptable salt of the compound of claim 1, wherein $R_1$ is methyl and $R_2$ is hydrogen.

7. The compound or pharmaceutically acceptable salt of the compound of claim 1, wherein $R_4$ is methyl or ethyl and $R_5$ is hydrogen.

8. The compound or pharmaceutically acceptable salt of the compound of claim 1, wherein when $R_4$ is other than hydrogen, the compound or pharmaceutically acceptable salt of the compound is the S-enantiomer with respect to the carbon to which $R_4$ is bound.

9. The compound or pharmaceutically acceptable salt of the compound of claim 5, wherein the one $R_6$ substituent is ethyl, t-butyl, —N($CH_2CH_3$)$_2$, pyrrolidine, 2-hydroxymethylpyrrolidine, or isopropyl.

10. The compound or pharmaceutically acceptable salt of the compound of claim 1, wherein $R_3$ is

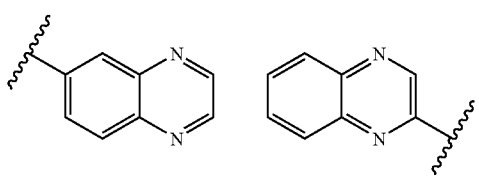

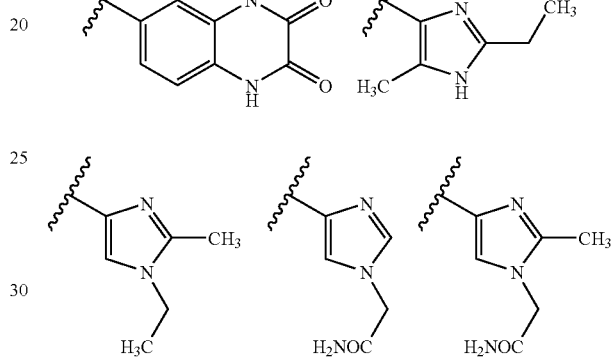

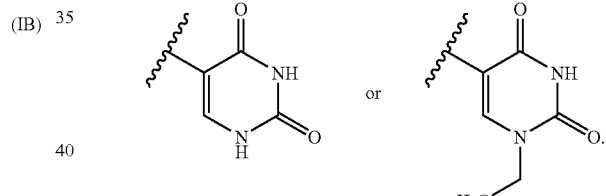

11. The compound or pharmaceutically acceptable salt of the compound of claim 1, wherein $R_3$ is

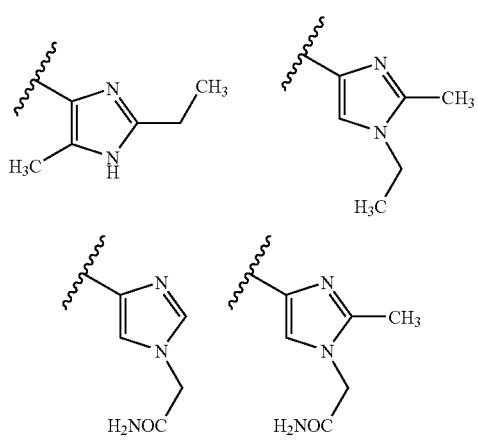

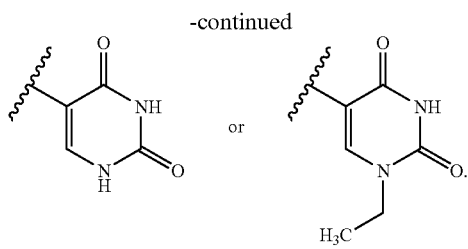

12. The compound or pharmaceutically acceptable salt of the compound of claim 1, wherein R$_2$, R$_5$, R$_{18}$, R$_{19}$, R$_{20}$, R$_{21}$, R$_{22}$, R$_{24}$, R$_{25}$, R$_{26}$, and R$_{27}$ are each hydrogen;

R$_1$ and R$_4$ are each independently hydrogen, methyl, or ethyl;

Ar is phenyl;

one R$_6$ is attached at the 4-position of phenyl and is ethyl, t-butyl, —N(CH$_2$CH$_3$)$_2$, pyrrolidine, 2-hydroxymethylpyrrolidine, or isopropyl; and R$_3$ is

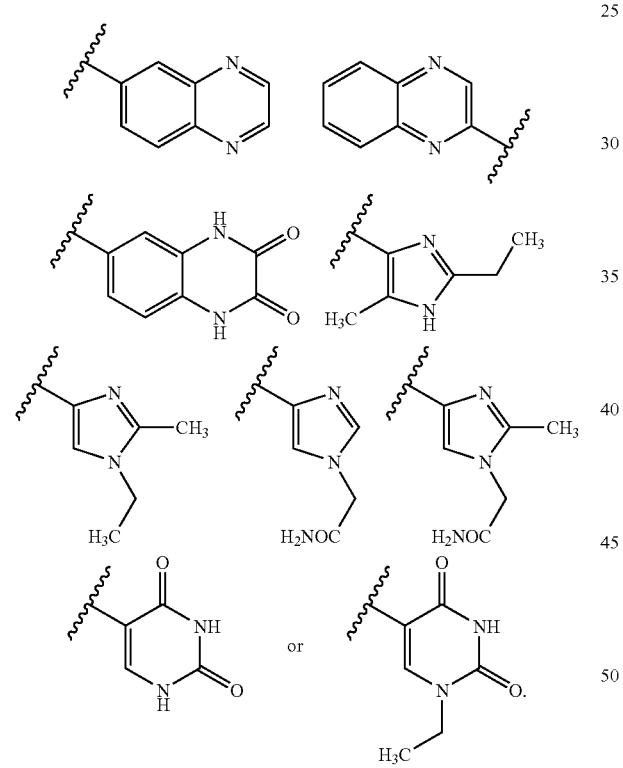

13. The compound or pharmaceutically acceptable salt of the compound of claim 1, wherein the compound is 2-(4-{4-[2-(4-tert-Butyl-phenyl)-benzooxazol-4-yl]-piperazin-1-ylmethyl}-imidazol-1-yl)-acetamide;

2-(4-{4-[2-(4-tert-Butyl-phenyl)-benzooxazol-4-yl]-piperazin-1-ylmethyl}-2-methyl-imidazol-1-yl)-acetamide;

2-(4-{4-[2-(4-tert-Butyl-phenyl)-benzooxazol-7-yl]-piperazin-1-ylmethyl}-2-methyl-imidazol-1-yl)-acetamide;

2-(4-{4-[2-(4-tert-Butyl-phenyl)-benzooxazol-7-yl]-piperazin-1-ylmethyl}-imidazol-1-yl)-acetamide;

2-(4-tert-Butyl-phenyl)-7-[4-(2-ethyl-5-methyl-1H-imidazol-4-ylmethyl)-piperazin-1-yl]-benzooxazole;

2-(4-tert-Butyl-phenyl)-4-[4-(2-ethyl-5-methyl-1H-imidazol-4-ylmethyl)-piperazin-1-yl]-benzooxazole;

2-(4-tert-Butyl-phenyl)-4-[4-(2-ethyl-5-methyl-1H-imidazol-4-ylmethyl)-piperazin-1-yl]-benzothiazole;

2-(4-tert-Butyl-phenyl)-7-[4-(2-ethyl-5-methyl-1H-imidazol-4-ylmethyl)-piperazin-1-yl]-benzothiazole;

3-{4-[2-(4-tert-Butyl-phenyl)-benzothiazol-7-yl]-piperazin-1-ylmethyl}-pyrido[2,3-b]pyrazine;

3-{4-[2-(4-tert-Butyl-phenyl)-benzothiazol-4-yl]-piperazin-1-ylmethyl}-pyrido[2,3-b]pyrazine;

2-{4-[2-(4-tert-Butyl-phenyl)-benzothiazol-4-yl]-piperazin-1-ylmethyl}-quinoxaline;

5-{4-[2-(4-tert-Butyl-phenyl)-benzothiazol-4-yl]-piperazin-1-ylmethyl}-1-ethyl-1H-pyrimidine-2,4-dione;

5-{4-[2-(4-tert-Butyl-phenyl)-benzothiazol-4-yl]-piperazin-1-ylmethyl}-1H-pyrimidine-2,4-dione;

2-(4-tert-Butyl-phenyl)-4-[4-(1-ethyl-5-methyl-1H-imidazol-4-ylmethyl)-piperazin-1-yl]-benzothiazole;

2-(4-tert-Butyl-phenyl)-7-[4-(1-ethyl-5-methyl-1H-imidazol-4-ylmethyl)-piperazin-1-yl]-benzothiazole;

5-{4-[2-(4-tert-Butyl-phenyl)-benzothiazol-7-yl]-piperazin-1-ylmethyl}-1-ethyl-1H-pyrimidine-2,4-dione;

5-{4-[2-(4-tert-Butyl-phenyl)-benzothiazol-7-yl]-piperazin-1-ylmethyl}-1H-pyrimidine-2,4-dione;

6-{4-[2-(4-tert-Butyl-phenyl)-benzooxazol-4-yl]-piperazin-1-ylmethyl}-quinoxaline;

6-{4-[2-(4-tert-Butyl-phenyl)-benzooxazol-7-yl]-piperazin-1-ylmethyl}-quinoxaline;

6-{4-[2-(4-tert-Butyl-phenyl)-benzothiazol-4-yl]-piperazin-1-ylmethyl}-quinoxaline;

6-{4-[2-(4-tert-Butyl-phenyl)-benzothiazol-7-yl]-piperazin-1-ylmethyl}-quinoxaline; or 2-{4-[2-(4-tert-Butyl-phenyl)-benzothiazol-7-yl]-piperazin-1-ylmethyl}-quinoxaline.

14. A compound of the formula (II):

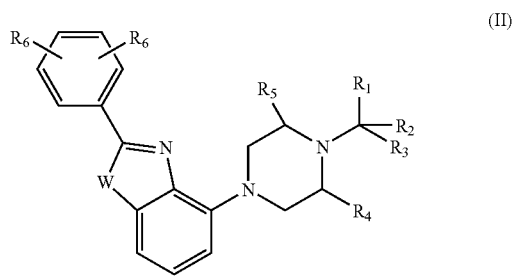

or a pharmaceutically acceptable salt thereof, wherein

W is O or S;

R$_1$ and R$_2$ are each independently hydrogen; or linear or branched (C$_1$-C$_6$)-alkyl, (C$_2$-C$_6$)-alkenyl, or (C$_2$-C$_6$)-alkynyl, each optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, or —CON(R$_{23}$)$_2$; or R$_1$ and R$_2$ may together form a three- to seven-membered cycloalkyl group, wherein the cycloalkyl group formed by R$_1$ and R$_2$ is optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —(CH$_2$)$_n$OR$_{23}$;

R₃ is one of the following:

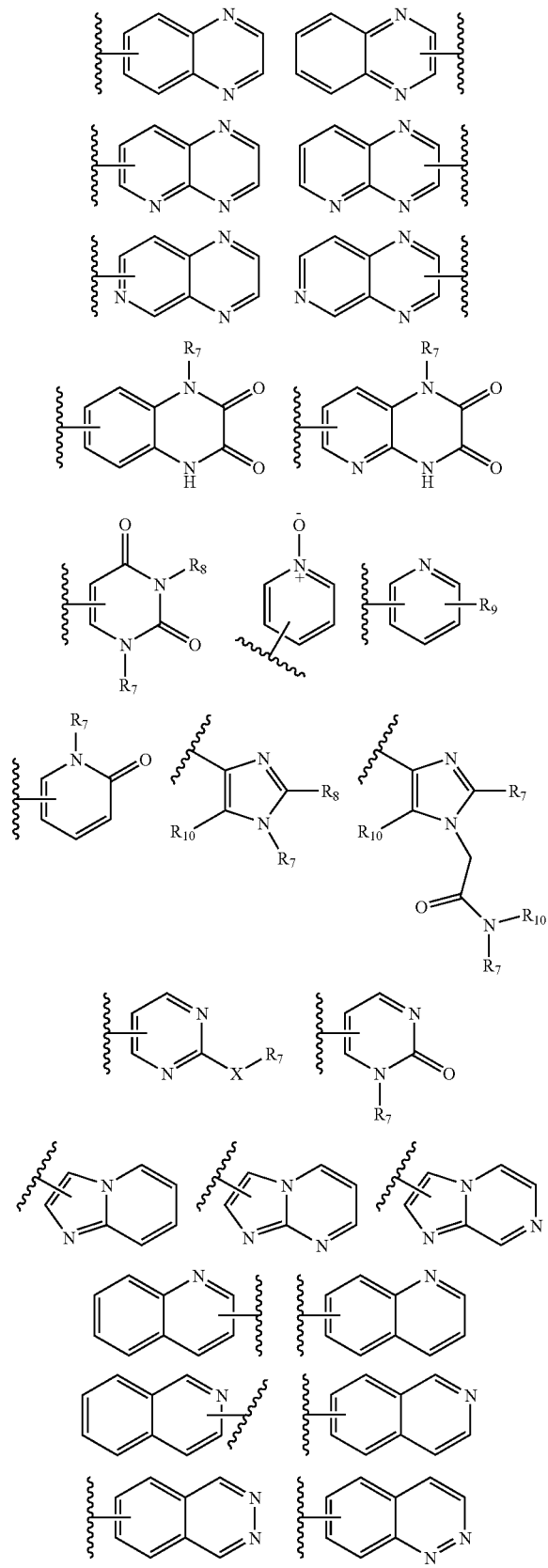

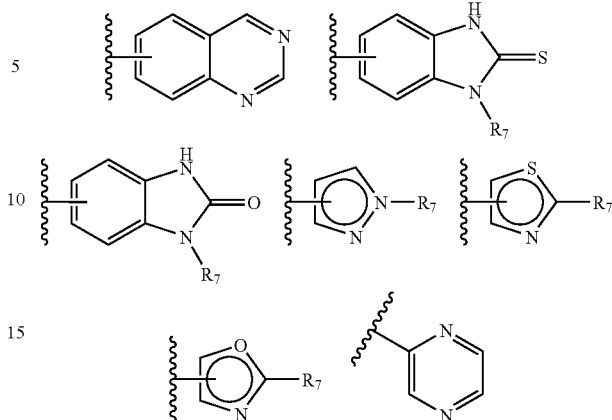

each R₃ also having up to three R₁₀ substituents attached to the ring of R₃ containing at least one N;

R₄, R₅, R₁₀, and R₂₃ are each independently hydrogen; or linear or branched $(C_1$-$C_6)$-alkyl, $(C_2$-$C_6)$-alkenyl, or $(C_2$-$C_6)$-alkynyl;

each R₆ is independently hydrogen; linear or branched $(C_1$-$C_6)$-alkyl, $(C_2$-$C_6)$-alkenyl, or $(C_2$-$C_6)$-alkynyl, each optionally substituted with halogen, —N₃, —NO₂, —CN, —OR₂₃, —SR₂₃, —SO₂R₂₃, —SO₂N(R₂₃)₂, —N(R₂₃)₂, —COR₂₃, —CO₂R₂₃, —NR₂₃CO₂R₂₃, —NR₂₃COR₂₃, —NR₂₃CON(R₂₃)₂, or —CON(R₂₃)₂; —NR₁₃R₁₄; —C(OH)(CF₃)₂; —CH(CF₃)₂; —C(CF₃)₃; —XR₁₃; or —COR₁₃; and the when the two R₆ are ortho to each other, they may together form a five- to seven-membered cyclic group containing up to 3 heteroatoms selected from N, O, or S, and wherein the cyclic group formed by the ortho R₆ groups is optionally substituted with halogen, —N₃, —NO₂, —CN, —OR₂₃, —SR₂₃, —SO₂R₂₃, —SO₂N(R₂₃)₂, —N(R₂₃)₂, —COR₂₃, —CO₂R₂₃, —NR₂₃CO₂R₂₃, —NR₂₃COR₂₃, —NR₂₃CON(R₂₃)₂, —CON(R₂₃)₂, or —(CH₂)ₙOR₂₃;

R₇ and R₉ are each independently hydrogen; linear or branched $(C_1$-$C_6)$-alkyl, $(C_2$-$C_6)$-alkenyl, or $(C_2$-$C_6)$-alkynyl; —(CH₂)ₙXR₁₂; —(CH₂)ₙR₁₇; —COXR₁₁; —XR₁₁; —CO₂R₁₁; or —CONR₁₁R₁₂;

R₈ is hydrogen; linear or branched $(C_1$-$C_6)$-alkyl, $(C_2$-$C_6)$-alkenyl, or $(C_2$-$C_6)$-alkynyl; —(CH₂)ₘCO₂R₁₁; or —(CH₂)ₘCONR₁₁R₁₂;

R₁₁ and R₁₂ are each independently hydrogen; linear or branched $(C_1$-$C_6)$-alkyl, $(C_2$-$C_6)$-alkenyl, or $(C_2$-$C_6)$-alkynyl; or R₁₁ and R₁₂ may together form a three- to seven-membered heterocyclic group containing up to 3 heteroatoms selected from N, O, or S;

R₁₃ and R₁₄ are each independently hydrogen; linear or branched $(C_1$-$C_6)$-alkyl, $(C_2$-$C_6)$-alkenyl, or $(C_2$-$C_6)$-alkynyl, each optionally substituted with halogen, —N₃, —NO₂, —CN, —OR₂₃, —SR₂₃, —SO₂R₂₃, —SO₂N(R₂₃)₂, —N(R₂₃)₂, —COR₂₃, —CO₂R₂₃, —NR₂₃CO₂R₂₃, —NR₂₃COR₂₃, —NR₂₃CON(R₂₃)₂, or —CON(R₂₃)₂; aryl; or aryl optionally substituted with one to three substituents selected from halogen, R₁₅, —OR₁₅, or —NR₁₅R₁₆; or R₁₃ and R₁₄ may together form a three- to seven-membered heterocyclic group containing up to 3 heteroatoms selected from N, O, or S, and wherein the heterocyclic group formed by R₁₃ and R₁₄ is optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —(CH$_2$)$_n$OR$_{23}$;

R$_{15}$ and R$_{16}$ are each independently hydrogen; or linear or branched (C$_1$-C$_6$)-alkyl, (C$_2$-C$_6$)-alkenyl, or (C$_2$-C$_6$)-alkynyl; or both R$_{15}$ and R$_{16}$ may together form a three- to seven-membered heterocyclic group containing up to 3 heteroatoms selected from N, O, or S;

R$_{17}$ is phenyl, 2-pyridyl, 3-pyridyl, or 4-pyridyl;

X is —O—, —NR$_{12}$—, or —SO$_m$—;

each m is independently 0, 1, or 2; and each n is independently 0, 1, 2, 3, or 4.

15. The compound or pharmaceutically acceptable salt of the compound of claim 14, wherein R$_1$ and R$_4$ are each independently hydrogen, methyl, or ethyl;

R$_2$ and R$_5$ are hydrogen;

one R$_6$ is attached at the 4-position of phenyl and is ethyl, t-butyl, —N(CH$_2$CH$_3$)$_2$, pyrrolidine, 2-hydroxymethylpyrrolidine, or isopropyl; and R$_3$ is

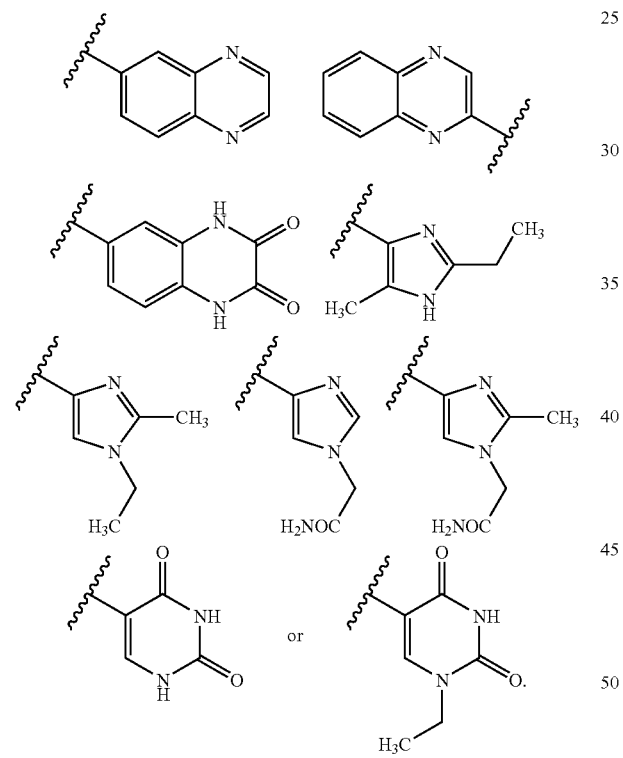

16. A composition comprising an effective amount of the compound or a Pharmaceutically acceptable salt of the compound of claim 1 and a pharmaceutically acceptable carrier.

17. The composition of claim 16, further comprising a therapeutic agent selected from the group consisting of androgen, estrogen, progesterone, antiestrogen, antiprogestogen, testosterone, angiotensin-converting enzyme inhibitor, angiotensin II-receptor antagonist, renin inhibitor, bisphosphonate, growth hormone secretagogue, 5a-reductase 2 inhibitor, a 5a-reductase 1 inhibitor, a dual inhibitor of 5a-reductase 1 and 5a-reductase 2, antiandrogen, alpha-1 blockers, growth hormone, and luteinizing hormone releasing compound; or a combination thereof.

18. The composition of claim 16, wherein the pharmaceutically acceptable carrier is suitable for oral administration and the composition comprises an oral dosage form.

19. A method for treating a GnRH-related disorder, wherein the GnRH-related disorder is prostate cancer, testicular cancer, uterine cancer, ovarian cancer, breast cancer, pituitary gonadotrophe adenomas, endometriosis, polycystic ovarian disease, uterine fibroids, primary hirsutism, luteinizing hormone surge, or precocious puberty, comprising administering to a mammal in need thereof a compound of the formula. (I):

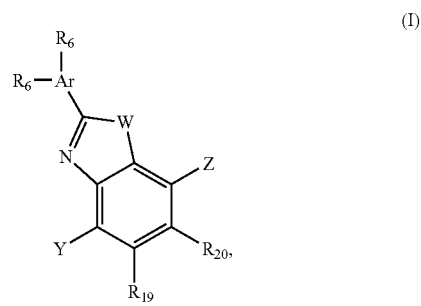

or a pharmaceutically acceptable salt thereof, in an amount effective to treat the GnRH-related disorder;

wherein

W is O or S;

Y is Q and Z is R$_{18}$; or Y is R$_{18}$ and Z is Q, wherein Q is

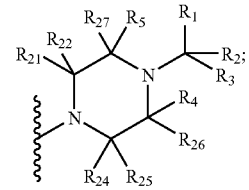

Ar is phenyl, 2-thiophenyl or 3-thiophenyl;

R$_1$ and R$_2$ are each independently hydrogen; or linear or branched (C$_1$-C$_6$)-alkyl, (C$_2$-C$_6$)-alkenyl, or (C$_2$-C$_6$)-alkynyl, each optionally substituted with halogen, —N$_3$, —NO$_2$, —CN, —OR$_{23}$, —SR$_{23}$, —SO$_2$R$_{23}$, —SO$_2$N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, or —CON(R$_{23}$)$_2$; or R$_1$ and R$_2$ may together form a three- to seven-membered cycloalkyl group, wherein the cycloalkyl group formed by R$_1$ and R$_2$ is optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —(CH$_2$)$_n$OR$_{23}$;

R$_3$ is one of the following:

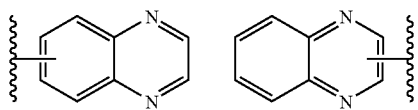

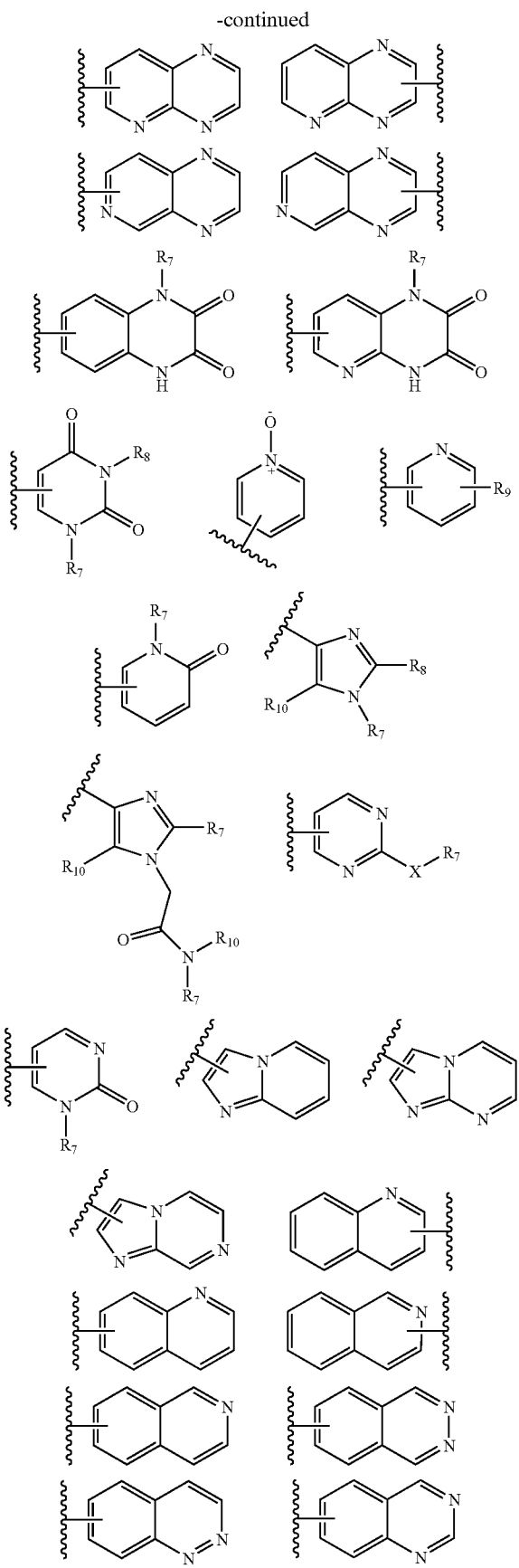

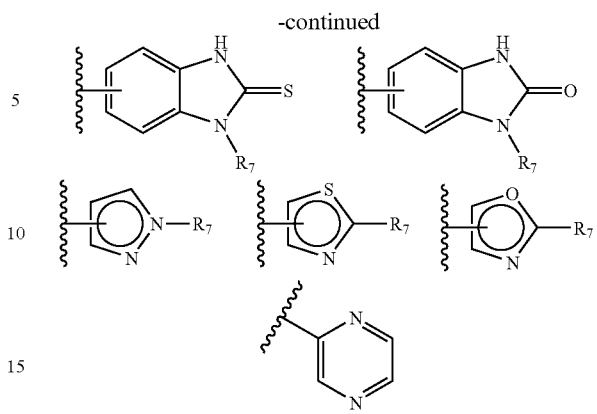

each $R_3$ also having up to three $R_{10}$ substituents attached to the ring of $R_3$ containing at least one N;

$R_4$, $R_5$, $R_{10}$, $R_{21}$, $R_{22}$, $R_{23}$, $R_{24}$, $R_{25}$, $R_{26}$, and $R_{27}$ are each independently hydrogen; or linear or branched $(C_1-C_6)$-alkyl, $(C_2-C_6)$-alkenyl, or $(C_2-C_6)$-alkynyl;

each $R_6$ is independently hydrogen; linear or branched $(C_1-C_6)$-alkyl, $(C_1-C_6)$-alkenyl, or $(C_2-C_6)$-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; —$NR_{13}R_{14}$; —$C(OH)(CF_3)_2$; —$CH(CF_3)_2$; —$C(CF_3)_3$; —$XR_{13}$; or —$COR_{13}$; and when the two $R_6$ are ortho to each other, they may together form a five- to seven-membered cyclic group containing up to 3 heteroatoms selected from N, O, or S, and wherein the cyclic group formed by the ortho $R_6$ groups is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{232}$, —$CON(R_{23})_2$, or —$(CH_2)_nOR_{23}$;

$R_7$ and $R_9$ are each independently hydrogen; linear or branched $(C_1-C_6)$-alkyl, $(C_2-C_6)$-alkenyl, or $(C_2-C_6)$-alkynyl; —$(CH_2)_nXR_{12}$; —$(CH_2)_nR_{17}$; —$COXR_{11}$; —$XR_{11}$; —$CO_2R_{11}$; or —$CONR_{11}R_{12}$;

$R_8$ is hydrogen; linear or branched $(C_1-C_6)$-alkyl, $(C_2-C_6)$-alkenyl, or $(C_2-C_6)$-alkynyl —$(CH_2)_mCO_2R_{11}$; or —$(CH_2)_mCONR_{11}R_{12}$;

$R_{11}$ and $R_{12}$ are each independently hydrogen; linear or branched $(C_1-C_6)$-alkyl, $(C_2-C_6)$-alkenyl, or $(C_2-C_6)$-alkynyl or $R_{11}$ and $R_{12}$ may together form a three- to seven-membered heterocyclic group containing up to 3 heteroatoms selected from N, O, or S;

$R_{13}$ and $R_{14}$ are each independently hydrogen; linear or branched $(C_1-C_6)$-alkyl, $(C_2-C_6)$-alkenyl, or $(C_2-C_6)$-alkynyl, each optionally substituted with halogen, —$N_3$, —$NO_2$, —CH, —$OR_{23}$, —$SR_{23}$, —$SO_2R_{23}$, —$SO_2N(R_{23})_2$, —$N(R_{23})_2$, —$COR_{23}$, —$CO_2R_{23}$, —$R_{23}CO_2R_{23}$, —$NR_{23}COR_{23}$, —$NR_{23}CON(R_{23})_2$, or —$CON(R_{23})_2$; aryl or aryl optionally substituted with one to three substituents selected from halogen, $R_{15}$, —$OR_{15}$, or —$NR_{15}R_{16}$; or $R_{13}$ and $R_{14}$ may together form a three- to seven-membered heterocyclic group containing up to 3 heteroatoms selected from N, O, or S, and wherein the heterocyclic group formed by $R_{13}$ and $R_{14}$ is optionally substituted with halogen, —$NO_3$, —$NO_2$, —CH, —$OR_{23}$, —$SR_{23}$, —$SO_2R_{23}$, —$SO_2N(R_{23})_2$, —$N(R_{23})_2$, —$COR_{23}$, —$CO_2R_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —(CH$_2$)$_n$OR$_{23}$;

R$_{15}$ and R$_{16}$ are each independently hydrogen; or linear or branched (C$_1$-C$_6$)-alkyl, (C$_2$-C$_6$)-alkenyl, or (C$_2$-C$_6$)-alkynyl or both R$_{15}$ and R$_{16}$ may together form a three- to seven-membered heterocyclic group containing up to 3 heteroatoms selected from N, O, or S;

R$_{17}$ is phenyl, 2-pyridyl, 3-pyridyl, or 4-pyridyl;

R$_{18}$, R$_{19}$, and R$_{20}$ are each independently hydrogen; linear or branched (C$_1$-C$_6$)-alkyl, (C$_2$-C$_6$)-alkenyl, or (C$_2$-C$_6$)-alkynyl, each optionally substituted with halogen, —N$_3$, —NO$_2$, —CH, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$; or —CON(R$_{23}$)$_2$; halogen; —NR$_{13}$R$_{14}$; —C(OH)(CF$_3$)$_2$; —CH(CF$_3$)$_2$; —C(CF$_3$)$_3$; —XR$_{13}$; —COR$_{13}$; —CO$_2$R$_{13}$; or —CON(R$_{13}$)(R$_{14}$);

X is —O—, —NR$_{12}$—, or —SO$_m$—;

each m is independently 0, 1, or 2; and each n is independently 0, 1, 2, 3, or 4.

20. The method of claim 19, wherein the GnRH-related disorder is breast cancer.

21. A method for preventing pregnancy, comprising administering to a female mammal the compound or pharmaceutically acceptable salt of the compound of claim 1 in an amount effective to prevent pregnancy.

22. The method of claim 21, further comprising administering to the mammal a therapeutic agent selected from the group consisting of androgen, estrogen, progesterone, antiestrogen, antiprogestogen, testosterone, angiotensin-converting enzyme inhibitor, angiotensin II-receptor antagonist, renin inhibitor, bisphosphonate, growth hormone secretagogue, 5a-reductase 2 inhibitor, 5a-reductase 1 inhibitor, a dual inhibitor of 5a-reductase 1 and 5a-reductase 2, antiandrogen, alpha-1 blockers, growth hormone, and luteinizing hormone releasing compound; or a combination thereof.

23. A method of synthesizing a compound comprising:
a) treating a compound of the formula (III):

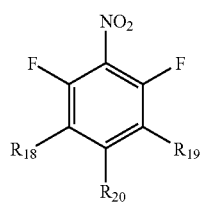

(III)

wherein R$_{18}$, R$_{19}$, and R$_{20}$ are each independently hydrogen; linear or branched (C$_1$-C$_6$)-alkyl, (C$_2$-C$_6$)-alkenyl, or (C$_2$-C$_6$)-alkynyl, each optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, or —CON(R$_{23}$)$_2$; halogen; —NR$_{13}$R$_{14}$; —C(OH)(CF$_3$)$_2$; —CH(CF$_3$)$_2$; —C(CF$_3$)$_3$; —XR$_{13}$; —COR$_{13}$; —CO$_2$R$_{13}$; or —CON(R$_{13}$)(R$_{14}$);

R$_{13}$ and R$_{14}$ are each independently hydrogen; linear or branched (C$_1$-C$_6$)-alkyl, (C$_2$-C$_6$)-alkenyl, or (C$_2$-C$_6$)-alkynyl, each optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —R$_{23}$CO$_2$R$_{23}$, —NR$_{23}$COR$_{23}$, —NR$_{23}$CON(R$_{23}$)$_2$, or —CON(R$_{23}$)$_2$; aryl; or aryl optionally substituted with one to three substituents selected from halogen, R$_{15}$, —OR$_{15}$, or —NR$_{15}$R$_{16}$; or R$_{13}$ and R$_{14}$ may together form a three- to seven-membered heterocyclic group containing up to 3 heteroatoms selected from N, O, or S, and wherein the heterocyclic group formed by R$_{13}$ and R$_{14}$ is optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —(CH$_2$)$_n$OR$_{23}$;

R$_{15}$ and R$_{16}$ are each independently hydrogen; or linear or branched (C$_1$-C$_6$)-alkyl, (C$_2$-C$_6$)-alkenyl, or (C$_2$-C$_6$)-alkynyl; or both R$_{15}$ and R$_{16}$ may together form a three- to seven-membered heterocyclic group containing up to 3 heteroatoms selected from N, O, or S;

R$_{23}$ is hydrogen; or linear or branched (C$_1$-C$_6$)-alkyl, (C$_2$-C$_6$)-alkenyl, or (C$_2$-C$_6$)-alkynyl;

X is —O—, —NR$_{12}$—, or —SO$_m$—;

R$_{12}$ is hydrogen; or linear or branched (C$_1$-C$_6$)-alkyl, (C$_2$-C$_6$)-alkenyl, or (C$_2$-C$_6$)-alkynyl;

each m is independently 0, 1, or 2;

each n is independently 0, 1, 2, 3, or 4;

with a protected piperazine, thereby providing a compound having the formula (IV):

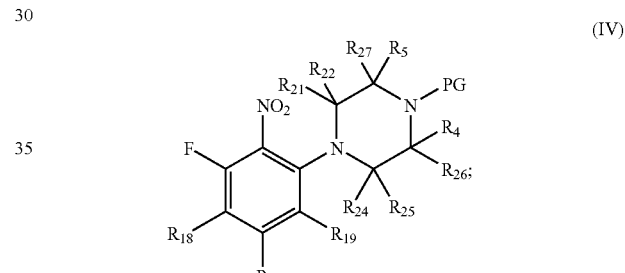

(IV)

wherein

PG is hydrogen or an amine protecting group;

R$_4$, R$_5$, R$_{21}$, R$_{22}$, R$_{24}$, R$_{25}$, R$_{26}$, and R$_{27}$ are each independently hydrogen; or linear or branched (C$_1$-C$_6$)-alkyl, (C$_2$-C$_6$)-alkenyl, or (C$_2$-C$_6$)-alkynyl;

b) treating the compound of the formula (IV) under conditions effective to introduce a hydroxyl group, thereby providing a compound having the formula (V):

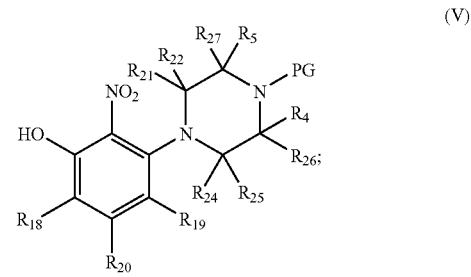

(V)

c) reacting the compound of the formula (V) under conditions effective to reduce the nitro group, bring about cyclization to form a benzooxazole ring, and deprotect the piperazine to provide a compound of the formula (VI):

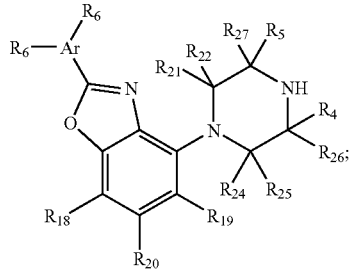

(VI)

wherein

Ar is phenyl, 2-thiophenyl or 3-thiophenyl; and each $R_6$ is independently hydrogen; linear or branched $(C_1-C_6)$-alkyl, $(C_2-C_6)$-alkenyl, or $(C_2-C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, or $-CON(R_{23})_2$; $-NR_{13}R_{14}$; $-C(OH)(CF_3)_2$; $-CH(CF_3)_2$; $-C(CF_3)_3$; $-XR_{13}$; or $-COR_{13}$; and when the two $R_6$ are ortho to each other, they may together form a five- to seven-membered cyclic group containing up to 3 heteroatoms selected from N, O, or S, and wherein the cyclic group formed by the ortho $R_6$ groups is optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, $-CON(R_{23})_2$, or $-(CH_2)_nOR_{23}$; and d) reacting the free amine of the piperazine of the compound of formula (VI) under conditions effective to provide a compound of the formula (IA):

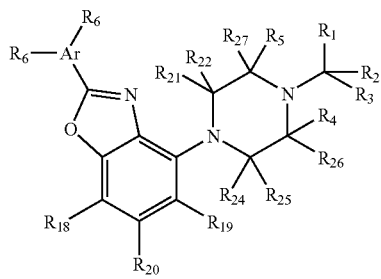

(IA)

wherein $R_1$ and $R_2$ are each independently hydrogen; or linear or branched $(C_1-C_6)$-alkyl, $(C_2-C_6)$-alkenyl, or $(C_2-C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, or $-CON(R_{23})_2$; or $R_1$ and $R_2$ may together form a three- to seven-membered cycloalkyl group, wherein the cycloalkyl group formed by $R_1$ and $R_2$ is optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, $-CON(R_{23})_2$, or $-(CH_2)_nOR_{23}$;

$R_3$ is one of the following:

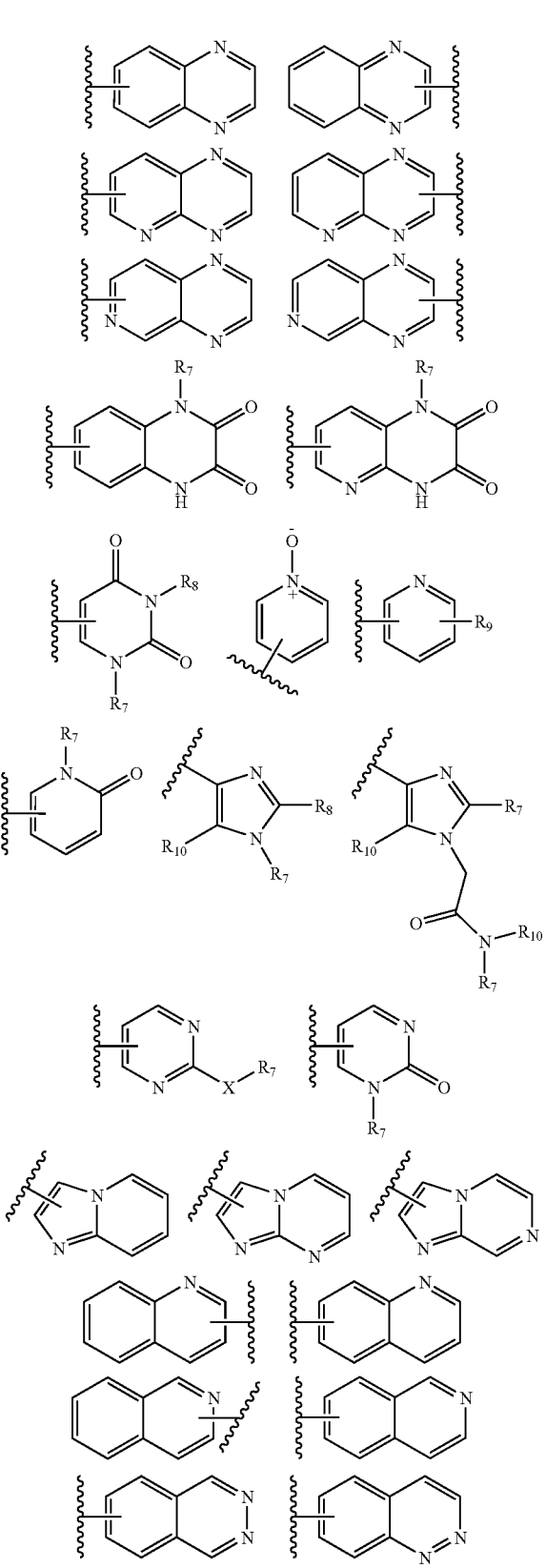

-continued

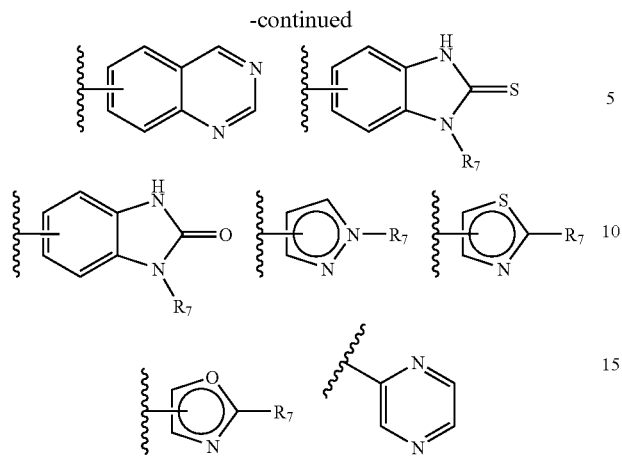

each $R_3$ also having up to three $R_{10}$ substituents attached to the ring of $R_3$ containing at least one N;

$R_7$ and $R_9$ are each independently hydrogen; linear or branched $(C_1-C_6)$-alkyl, $(C_2-C_6)$-alkenyl, or $(C_2-C_6)$-alkynyl; $-(CH_2)_n XR_{12}$; $-(CH_2)_n R_{17}$; $-COXR_{11}$; $-XR_{11}$; $-CO_2 R_{11}$; or $-CONR_{11}R_{12}$;

$R_8$ is hydrogen; linear or branched $(C_1-C_6)$-alkyl, $(C_2-C_6)$-alkenyl, or $(C_2-C_6)$-alkynyl; $-(CH_2)_m CO_2 R_{11}$; or $-(CH_2)_m CONR_{11}R_{12}$; and each $R_{10}$ is independently hydrogen; or linear or branched $(C_1-C_6)$-alkyl, $(C_2-C_6)$-alkenyl, or $(C_2-C_6)$-alkynyl;

$R_{11}$ is hydrogen; linear or branched $(C_1-C_6)$-alkyl, $(C_2-C_6)$-alkenyl, or $(C_2-C_6)$-alkynyl; or $R_{11}$ and $R_{12}$ may together form a three- to seven-membered heterocyclic group containing up to 3 heteroatoms selected from N, O, or S; and $R_{17}$ is phenyl, 2-pyridyl, 3-pyridyl, or 4-pyridyl.

24. A method of synthesizing a compound comprising:
a) selectively reducing a compound of the formula (VII):

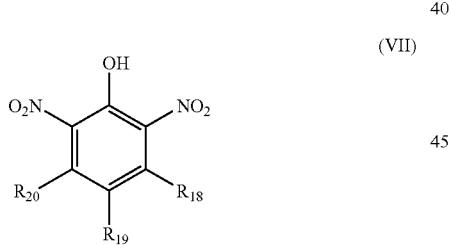

(VII)

wherein $R_{18}$, $R_{19}$, and $R_{20}$ are each independently hydrogen; linear or branched $(C_1-C_6)$-alkyl, $(C_2-C_6)$-alkenyl, or $(C_2-C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, or $-CON(R_{23})_2$; halogen; $-NR_{13}R_{14}$; $-C(OH)(CF_3)_2$; $-CH(CF_3)_2$; $-C(CF_3)_3$; $-XR_{13}$; $-COR_{13}$; $-CO_2R_{13}$; or $-CON(R_{13})(R_{14})$;

$R_{13}$ and $R_{14}$ are each independently hydrogen; linear or branched $(C_1-C_6)$-alkyl, $(C_2-C_6)$-alkenyl, or $(C_2-C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-R_{23}CO_2R_{23}$, $-NR_{23}COR_{23}$, $-NR_{23}CON(R_{23})_2$, or $-CON(R_{23})_2$; aryl; or aryl optionally substituted with one to three substituents selected from halogen, $R_{15}$, $-OR_{15}$, or $-NR_{15}R_{16}$; or $R_{13}$ and $R_{14}$ may together form a three- to seven-membered heterocyclic group containing up to 3 heteroatoms selected from N, O, or S, and wherein the heterocyclic group formed by $R_{13}$ and $R_{14}$ is optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, $-CON(R_{23})_2$, or $-(CH_2)_n OR_{23}$;

$R_{15}$ and $R_{16}$ are each independently hydrogen; or linear or branched $(C_1-C_6)$-alkyl, $(C_2-C_6)$-alkenyl, or $(C_2-C_6)$-alkynyl; or both $R_{15}$ and $R_{16}$ may together form a three- to seven-membered heterocyclic group containing up to 3 heteroatoms selected from N, O, or S;

$R_{23}$ is hydrogen; or linear or branched $(C_1-C_6)$-alkyl, $(C_2-C_6)$-alkenyl, or $(C_2-C_6)$-alkynyl;

X is $-O-$, $-NR_{12}-$, or $-SO_m-$;

$R_{12}$ is hydrogen; or linear or branched $(C_1-C_6)$-alkyl, $(C_2-C_6)$-alkenyl, or $(C_2-C_6)$-alkynyl;

each m is independently 0, 1, or 2;
each n is independently 0, 1, 2, 3, or 4;
thereby providing a compound having the formula (VIII):

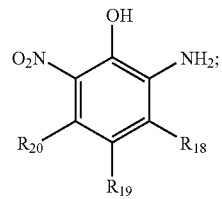

(VIII)

b) acylating the compound of the formula (VIII), thereby providing a compound having the formula (IX):

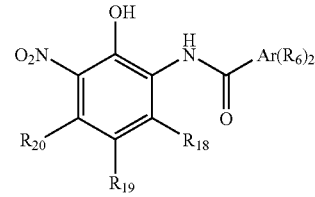

(IX)

wherein
Ar is phenyl, 2-thiophenyl or 3-thiophenyl;

each $R_6$ is independently hydrogen; linear or branched $(C_1-C_6)$-alkyl, $(C_2-C_6)$-alkenyl, or $(C_2-C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, or $-CON(R_{23})_2$; $-NR_{13}R_{14}$; $-C(OH)(CF_3)_2$; $-CH(CF_3)_2$; $-C(CF_3)_3$; $-XR_{13}$; or $-COR_{13}$; and when the two $R_6$ are ortho to each other, they may together form a five- to seven-membered cyclic group containing up to 3 heteroatoms selected from N, O, or S, and wherein the cyclic group formed by the ortho $R_6$ groups is optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, $-CON(R_{23})_2$, or $-(CH_2)_n OR_{23}$;

c) reacting the compound of the formula (IX) under conditions effective to bring about cyclization to provide a compound of the formula (X):

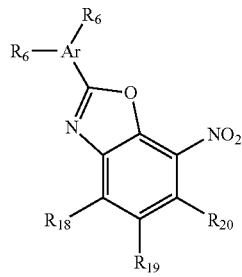
(X)

d) reacting the compound of the formula (X) under reductive conditions effective to provide a compound of the formula (XI):

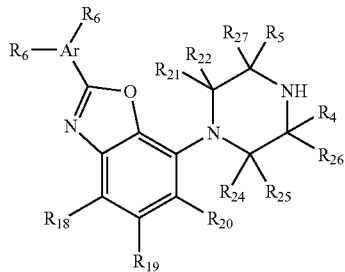
(XI)

wherein
$R_4$, $R_5$, $R_{21}$, $R_{22}$, $R_{24}$, $R_{25}$, $R_{26}$, and $R_{27}$ are each independently hydrogen; or linear or branched $(C_1-C_6)$-alkyl, $(C_2-C_6)$-alkenyl, or $(C_2-C_6)$-alkynyl; and e) reacting the free amine of the piperazine of the compound of the formula (XI) under conditions effective to provide a compound of the formula (IC):

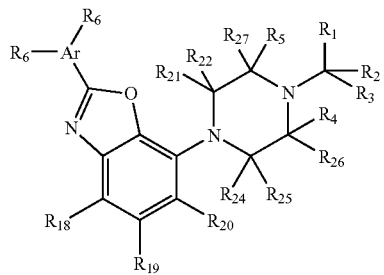
(IC)

wherein
$R_1$ and $R_2$ are each independently hydrogen; or linear or branched $(C_1-C_6)$-alkyl, $(C_2-C_6)$-alkenyl, or $(C_2-C_6)$-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; or $R_1$ and $R_2$ may together form a three- to seven-membered cycloalkyl group, wherein the cycloalkyl group formed by $R_1$ and $R_2$ is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_3$ is one of the following:

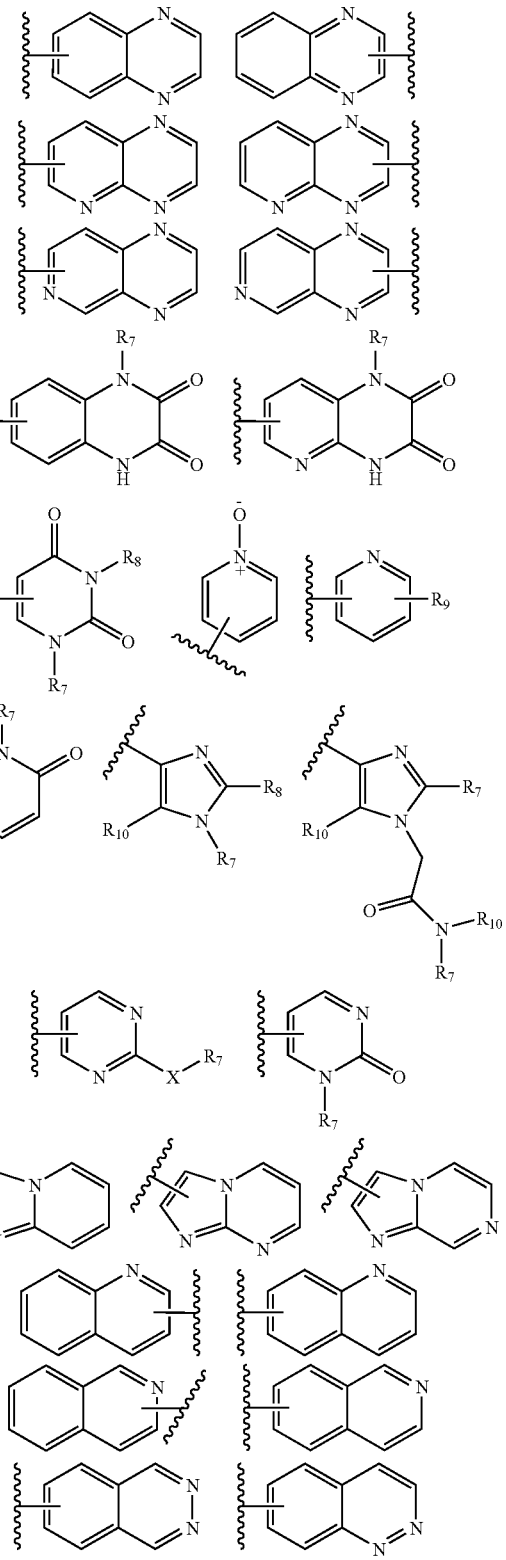

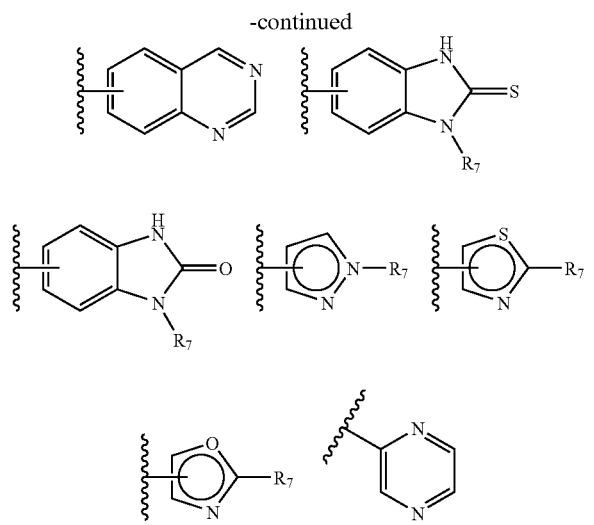

each $R_3$ also having up to three $R_{10}$ substituents attached to the ring of $R_3$ containing at least one N;

$R_7$ and $R_9$ are each independently hydrogen; linear or branched $(C_1\text{-}C_6)$-alkyl, $(C_2\text{-}C_6)$-alkenyl, or $(C_2\text{-}C_6)$-alkynyl; —$(CH_2)_nXR_{12}$; —$(CH_2)_nR_{17}$; —$COXR_{11}$; —$XR_{11}$; —$CO_2R_{11}$; or —$CONR_{11}R_{12}$;

$R_8$ is hydrogen; linear or branched $(C_1\text{-}C_6)$-alkyl, $(C_2\text{-}C_6)$-alkenyl, or $(C_2\text{-}C_6)$-alkynyl; —$(CH_2)_mCO_2R_{11}$; or —$(CH_2)_mCONR_{11}R_{12}$;

each $R_{10}$ is independently hydrogen; or linear or branched $(C_1\text{-}C_6)$-alkyl, $(C_2\text{-}C_6)$-alkenyl, or $(C_2\text{-}C_6)$-alkynyl;

$R_{11}$ is hydrogen; linear or branched $(C_1\text{-}C_6)$-alkyl, $(C_2\text{-}C_6)$-alkenyl, or $(C_2\text{-}C_6)$-alkynyl; or $R_{11}$ and $R_{12}$ may together form a three- to seven-membered heterocyclic group containing up to 3 heteroatoms selected from N, O, or S; and $R_{17}$ is phenyl, 2-pyridyl, 3-pyridyl, or 4-pyridyl.

25. A method of synthesizing a compound comprising:
a) acylating a compound of the formula (XII):

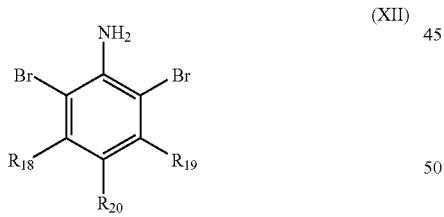

wherein $R_{18}$, $R_{19}$, and $R_{20}$ are each independently hydrogen; linear or branched $(C_1\text{-}C_6)$-alkyl, $(C_2\text{-}C_6)$-alkenyl, or $(C_2\text{-}C_6)$-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; halogen; —$NR_{13}R_{14}$; —$C(OH)(CF_3)_2$; —$CH(CF_3)_2$; —$C(CF_3)_3$; —$XR_{13}$; —$COR_{13}$; —$CO_2R_{13}$; or —$CON(R_{13})(R_{14})$;

$R_{13}$ and $R_{14}$ are each independently hydrogen; linear or branched $(C_1\text{-}C_6)$-alkyl, $(C_2\text{-}C_6)$-alkenyl, or $(C_2\text{-}C_6)$-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$R_{23}CO_2R_{23}$, —$NR_{23}COR_{23}$, —$NR_{23}CON(R_{23})_2$, or —$CON(R_{23})_2$; aryl; or aryl optionally substituted with one to three substituents selected from halogen, $R_{15}$, —$OR_{15}$, or —$NR_{15}R_{16}$; or $R_{13}$ and $R_{14}$ may together form a three- to seven-membered heterocyclic group containing up to 3 heteroatoms selected from N, O, or S, and wherein the heterocyclic group formed by $R_{13}$ and $R_{14}$ is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_{15}$ and $R_{16}$ are each independently hydrogen; or linear or branched $(C_1\text{-}C_6)$-alkyl, $(C_2\text{-}C_6)$-alkenyl, or $(C_2\text{-}C_6)$-alkynyl; or both $R_{15}$ and $R_{16}$ may together form a three- to seven-membered heterocyclic group containing up to 3 heteroatoms selected from N, O, or S;

$R_{23}$ is hydrogen; or linear or branched $(C_1\text{-}C_6)$-alkyl, $(C_2\text{-}C_6)$-alkenyl, or $(C_2\text{-}C_6)$-alkynyl;

X is —O—, —$NR_{12}$—, or —$SO_m$—;

$R_{12}$ is hydrogen; or linear or branched $(C_1\text{-}C_6)$-alkyl, $(C_2\text{-}C_6)$-alkenyl, or $(C_2\text{-}C_6)$-alkynyl;

each m is independently 0, 1, or 2;

each n is independently 0, 1, 2, 3, or 4;

thereby providing a compound having the formula (XIII):

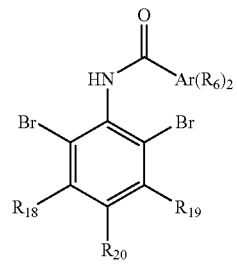

wherein

Ar is phenyl, 2-thiophenyl or 3-thiophenyl;

each $R_6$ is independently hydrogen; linear or branched $(C_1\text{-}C_6)$-alkyl, $(C_2\text{-}C_6)$-alkenyl, or $(C_2\text{-}C_6)$-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; —$NR_{13}R_{14}$; —$C(OH)(CF_3)_2$; —$CH(CF_3)_2$; —$C(CF_3)_3$; —$XR_{13}$; or —$COR_{13}$; and when the two $R_6$ are ortho to each other, they may together form a five- to seven-membered cyclic group containing up to 3 heteroatoms selected from N, O, or S, and wherein the cyclic group formed by the ortho $R_6$ groups is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

b) thiolating the compound of the formula (XIII), thereby providing a compound having the formula (XIV):

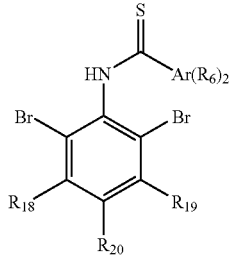
(XIV)

c) reacting the compound of the formula (XIV) under conditions effective to bring about cyclization to provide a benzothiazole ring and reacting with a piperazine to provide a compound of the formula (XV):

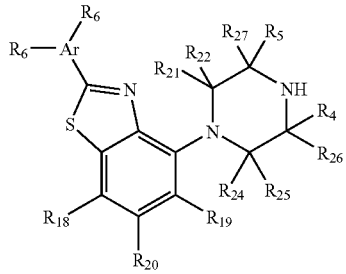
(XV)

wherein
$R_4$, $R_5$, $R_{21}$, $R_{22}$, $R_{24}$, $R_{25}$, $R_{26}$, and $R_{27}$ are each independently hydrogen; or linear or branched $(C_1\text{-}C_6)$-alkyl, $(C_2\text{-}C_6)$-alkenyl, or $(C_2\text{-}C_6)$-alkynyl; and d) reacting the free amine of the piperazine of the compound of the formula (XV) under conditions effective to provide a compound of the formula (IB):

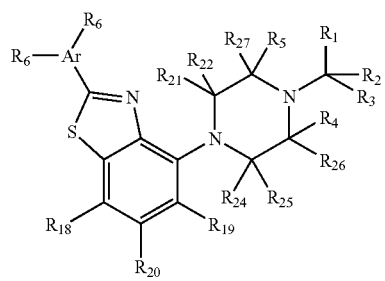
(IB)

wherein
$R_1$ and $R_2$ are each independently hydrogen; or linear or branched $(C_1\text{-}C_6)$-alkyl, $(C_2\text{-}C_6)$-alkenyl, or $(C_2\text{-}C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, or $-CON(R_{23})_2$; or $R_1$ and $R_2$ may together form a three- to seven-membered cycloalkyl group, wherein the cycloalkyl group formed by $R_1$ and $R_2$ is optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, $-CON(R_{23})_2$, or $-(CH_2)_nOR_{23}$;

$R_3$ is one of the following:

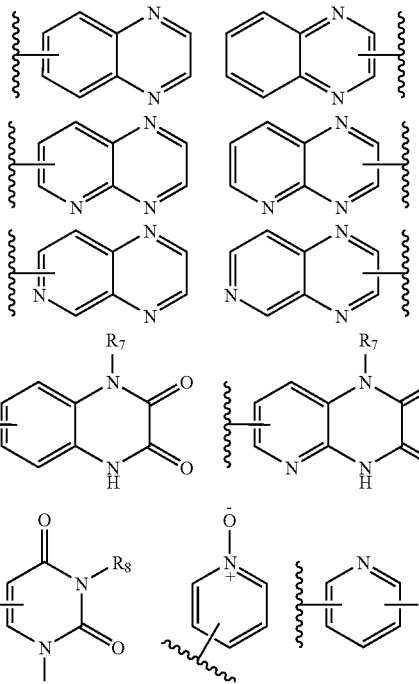

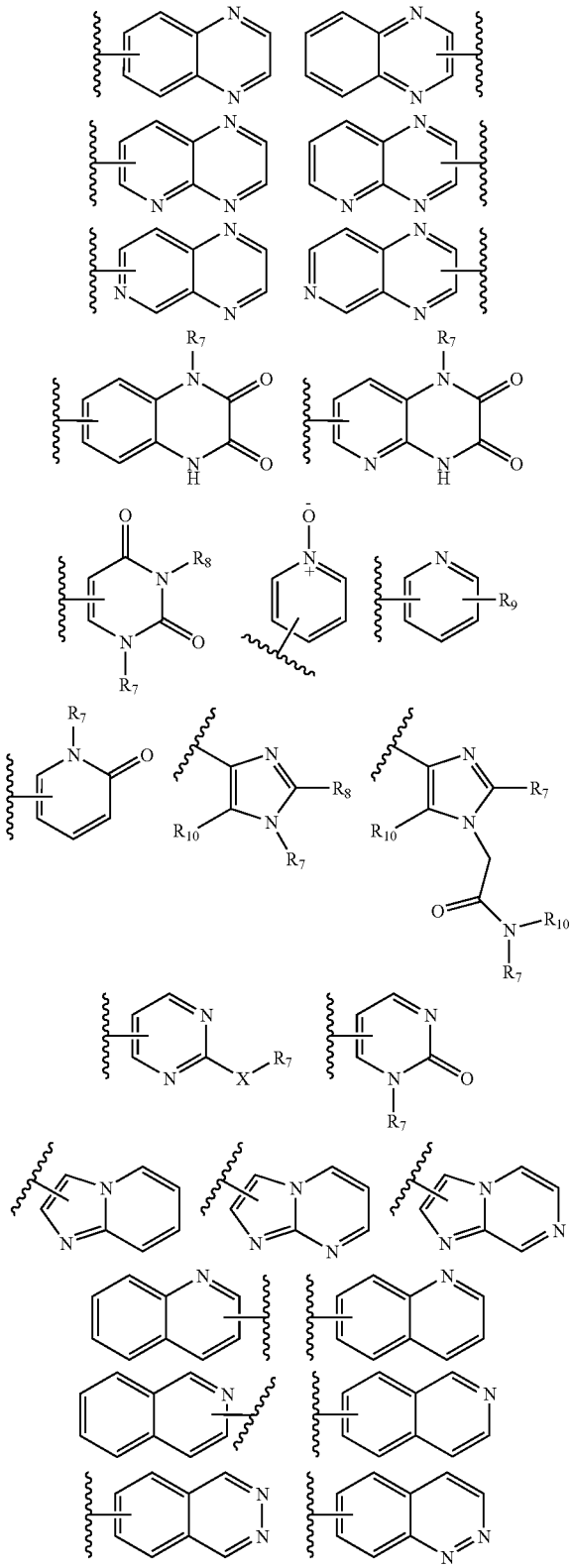

-continued

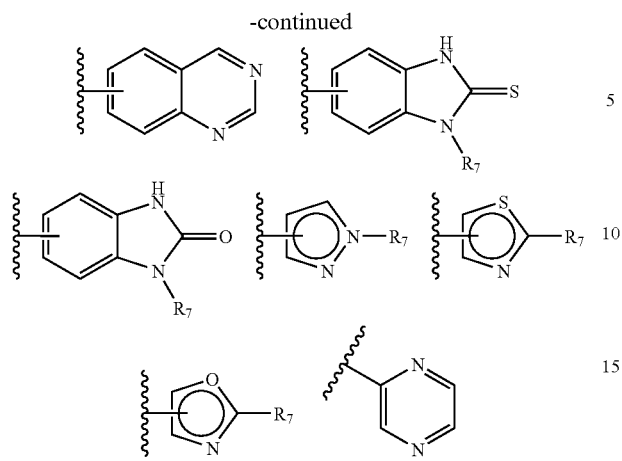

each $R_3$ also having up to three $R_{10}$ substituents attached to the ring of $R_3$ containing at least one N;

$R_7$ and $R_9$ are each independently hydrogen; linear or branched $(C_1-C_6)$-alkyl, $(C_2-C_6)$-alkenyl, or $(C_2-C_6)$-alkynyl; —$(CH_2)_nXR_{12}$; —$(CH_2)_nR_{17}$; —$COXR_{11}$; —$XR_{11}$; —$CO_2R_{11}$; or —$CONR_{11}R_{12}$;

$R_8$ is hydrogen; linear or branched $(C_1-C_6)$-alkyl, $(C_2-C_6)$-alkenyl, or $(C_2-C_6)$-alkynyl; —$(CH_2)_mCO_2R_{11}$; or —$(CH_2)_mCONR_{11}R_{12}$;

each $R_{10}$ is independently hydrogen; or linear or branched $(C_1-C_6)$-alkyl, $(C_2-C_6)$-alkenyl, or $(C_2-C_6)$-alkynyl;

$R_{11}$ is hydrogen; linear or branched $(C_1-C_6)$-alkyl, $(C_2-C_6)$-alkenyl, or $(C_2-C_6)$-alkynyl; or $R_{11}$ and $R_{12}$ may together form a three- to seven-membered heterocyclic group containing up to 3 heteroatoms selected from N, O, or S; and $R_{17}$ is phenyl, 2-pyridyl, 3-pyridyl, or 4-pyridyl.

26. A method of synthesizing a compound comprising:
a) nitrating and then reducing a compound of the formula (XVI):

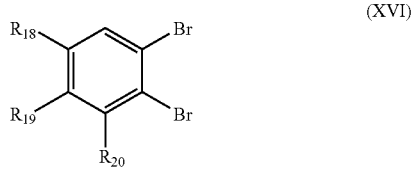

wherein $R_{18}$, $R_{19}$, and $R_{20}$ are each independently hydrogen; linear or branched $(C_1-C_6)$-alkyl, $(C_2-C_6)$-alkenyl, or $(C_2-C_6)$-alkynyl, each optionally substituted with halogen, —$N_3$, —$NO_2$, —$CN$, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; halogen; —$NR_{13}R_{14}$; —$C(OH)(CF_3)_2$; —$CH(CF_3)_2$; —$C(CF_3)_3$; —$XR_{13}$; —$COR_{13}$; —$CO_2R_{13}$; or —$CON(R_{13})(R_{14})$;

$R_{13}$ and $R_{14}$ are each independently hydrogen; linear or branched $(C_1-C_6)$-alkyl, $(C_2-C_6)$-alkenyl, or $(C_2-C_6)$-alkynyl, each optionally substituted with halogen, —$N_3$, —$NO_2$, —$CN$, —$OR_{23}$, —$SR_{23}$, —$SO_2R_{23}$, —$SO_2N(R_{23})_2$, —$N(R_{23})_2$, —$COR_{23}$, —$CO_2R_{23}$, —$R_{23}CO_2R_{23}$, —$NR_{23}COR_{23}$, —$NR_{23}CON(R_{23})_2$, or —$CON(R_{23})_2$; aryl; or aryl optionally substituted with one to three substituents selected from halogen, $R_{15}$, —$OR_{15}$, or —$NR_{15}R_{16}$; or $R_{13}$ and $R_{14}$ may together form a three- to seven-membered heterocyclic group containing up to 3 heteroatoms selected from N, O, or S, and wherein the heterocyclic group formed by $R_{13}$ and $R_{14}$ is optionally substituted with halogen, —$N_3$, —$NO_2$, —$CN$, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_{15}$ and $R_{16}$ are each independently hydrogen; or linear or branched $(C_1-C_6)$-alkyl, $(C_2-C_6)$-alkenyl, or $(C_2-C_6)$-alkynyl; or both $R_{15}$ and $R_{16}$ may together form a three- to seven-membered heterocyclic group containing up to 3 heteroatoms selected from N, O, or S;

$R_{23}$ is hydrogen; or linear or branched $(C_1-C_6)$-alkyl, $(C_2-C_6)$-alkenyl, or $(C_2-C_6)$-alkynyl;

X is —O—, —$NR_{12}$—, or —$SO_m$—;

$R_{12}$ is hydrogen; or linear or branched $(C_1-C_6)$-alkyl, $(C_2-C_6)$-alkenyl, or $(C_2-C_6)$-alkynyl;

each m is independently 0, 1, or 2;
each n is independently 0, 1, 2, 3, or 4;
thereby providing a compound having the formula (XVII):

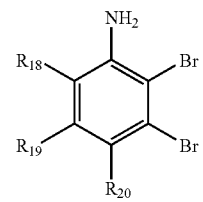

b) acylating the compound of the formula (XVII), thereby providing a compound having the formula (XVIII):

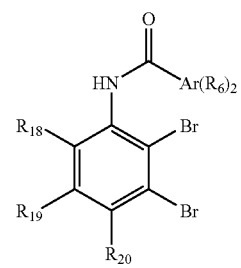

wherein
Ar is phenyl, 2-thiophenyl or 3-thiophenyl;
each $R_6$ is independently hydrogen; linear or branched $(C_1-C_6)$-alkyl, $(C_2-C_6)$-alkenyl, or $(C_2-C_6)$-alkynyl, each optionally substituted with halogen, —$N_3$, —$NO_2$, —$CN$, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; —$NR_{13}R_{14}$; —$C(OH)(CF_3)_2$; —$CH(CF_3)_2$; —$C(CF_3)_3$; —$XR_{13}$; or —$COR_{13}$; and when the two $R_6$ are ortho to each other, they may together form a five- to seven-membered cyclic group containing up to 3 heteroatoms selected from N, O, or S, and wherein the cyclic group formed by the ortho $R_6$ groups is optionally substituted with halogen, —$N_3$, —$NO_2$, —$CN$, —$OR_{23}$, —$SR_{23}$, —$SO_2R_{23}$, —$SO_2N(R_{23})_2$, —$N(R_{23})_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —(CH$_2$)$_n$OR$_{23}$;

c) thiolating the compound of the formula (XVIII), thereby providing a compound having the formula (XIX):

(XIX)

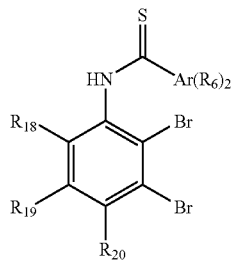

d) reacting the compound of the formula (XIX) under conditions effective to bring about cyclization to provide a benzothiazole ring and reacting with a piperazine to provide a compound of the formula (XX):

(XX)

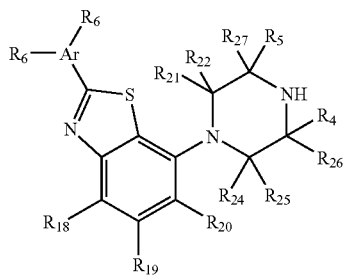

wherein
R$_4$, R$_5$, R$_{21}$, R$_{22}$, R$_{24}$, R$_{25}$, R$_{26}$, and R$_{27}$ are each independently hydrogen; or linear or branched (C$_1$-C$_6$)-alkyl, (C$_2$-C$_6$)-alkenyl, or (C$_2$-C$_6$)-alkynyl; and e) reacting the free amine of the piperazine of the compound of the formula (XX) under conditions effective to provide a compound of the formula (ID):

(ID)

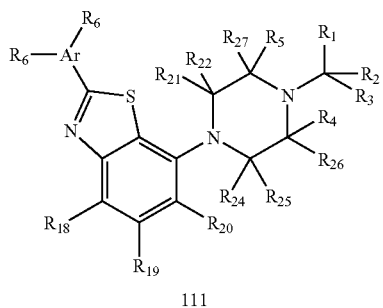

111 wherein
R$_1$ and R$_2$ are each independently hydrogen; or linear or branched (C$_1$-C$_6$)-alkyl, (C$_2$-C$_6$)-alkenyl, or (C$_2$-C$_6$)-alkynyl, each optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, or —CON(R$_{23}$)$_2$; or R$_1$ and R$_2$ may together form a three- to seven-membered cycloalkyl group, wherein the cycloalkyl group formed by R$_1$ and R$_2$ is optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —(CH$_2$)$_n$OR$_{23}$;

R$_3$ is one of the following:

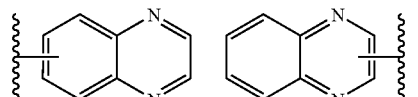
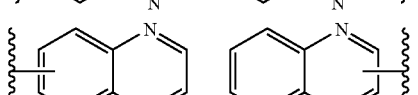
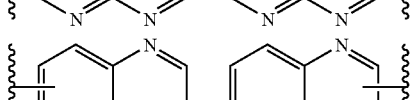
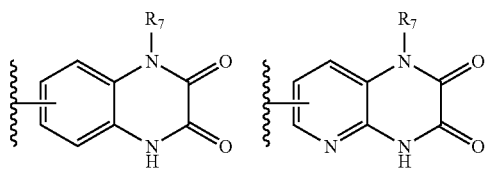
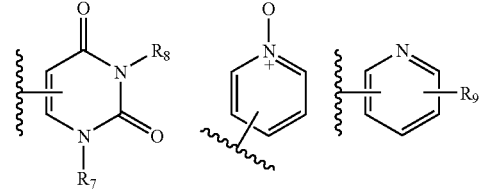
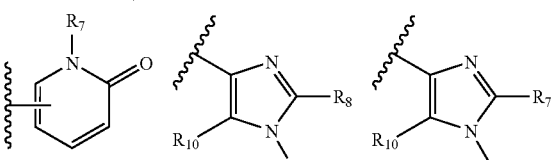
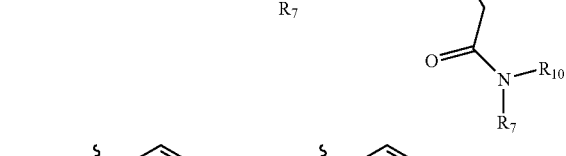
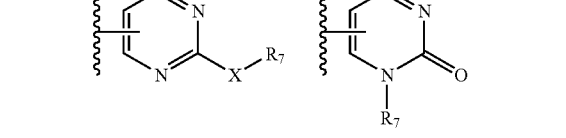
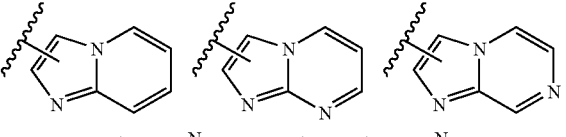
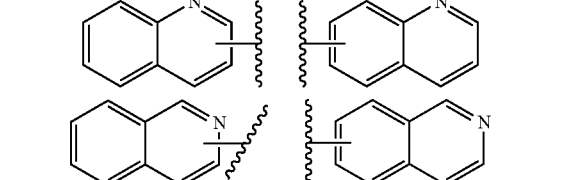

-continued

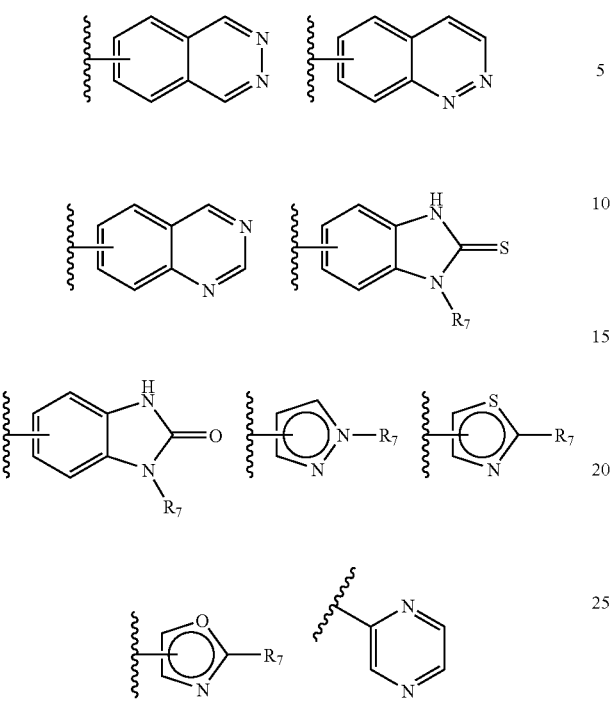

each $R_3$ also having up to three $R_{10}$ substituents attached to the ring of $R_3$ containing at least one N;

$R_7$ and $R_9$ are each independently hydrogen; linear or branched $(C_1\text{-}C_6)$-alkyl, $(C_2\text{-}C_6)$-alkenyl, or $(C_2\text{-}C_6)$-alkynyl; —$(CH_2)_nXR_{12}$; —$(CH_2)_nR_{17}$; —$COXR_{11}$; —$XR_{11}$; —$CO_2R_{11}$; or —$CONR_{11}R_{12}$;

$R_8$ is hydrogen; linear or branched $(C_1\text{-}C_6)$-alkyl, $(C_2\text{-}C_6)$-alkenyl, or $(C_2\text{-}C_6)$-alkynyl; —$(CH_2)_mCO_2R_{11}$; or —$(CH_2)_mCONR_{11}R_{12}$;

each $R_{10}$ is independently hydrogen; or linear or branched $(C_1\text{-}C_6)$-alkyl, $(C_2\text{-}C_6)$-alkenyl, or $(C_2\text{-}C_6)$-alkynyl;

$R_{11}$ is hydrogen; linear or branched $(C_1\text{-}C_6)$-alkyl, $(C_2\text{-}C_6)$-alkenyl, or $(C_2\text{-}C_6)$-alkynyl; or $R_{11}$ and $R_{12}$ may together form a three- to seven-membered heterocyclic group containing up to 3 heteroatoms selected from N, O, or S;

$R_{17}$ is phenyl, 2-pyridyl, 3-pyridyl, or 4-pyridyl.

27. A compound of the formula (IA):

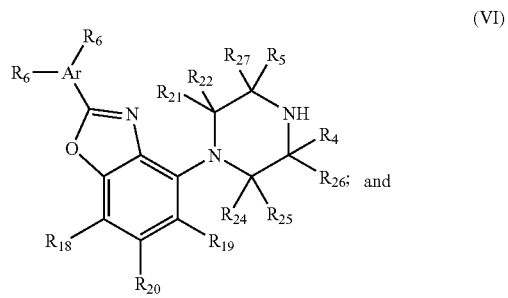

prepared by a method comprising:

a) treating a compound of the formula (III):

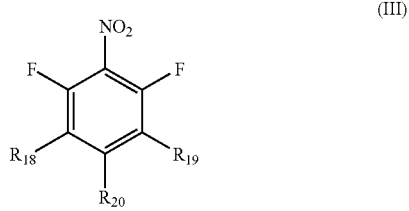

with a protected piperazine, thereby providing a compound having the formula (IV):

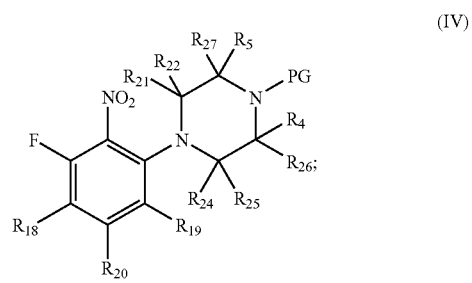

b) treating the compound of the formula (IV) under conditions effective to introduce a hydroxyl group, thereby providing a compound having the formula (V):

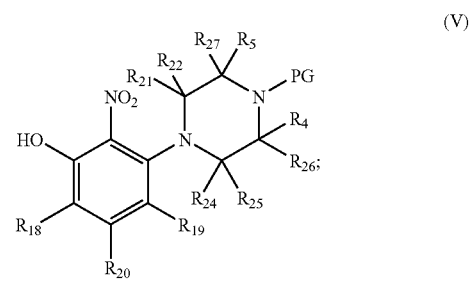

c) reacting the compound of the formula (V) under conditions effective to reduce the nitro group, bring about cyclization to form a benzooxazole ring, and deprotect the piperazine to provide a compound of the formula (VI):

d) reacting the free amine of the piperazine of the compound of formula (VI) under conditions effective to provide the compound of the formula (IA);

wherein

PG is hydrogen or an amine protecting group;

Ar is phenyl, 2-thiophenyl or 3-thiophenyl;

$R_1$ and $R_2$ are each independently hydrogen; or linear or branched $(C_1\text{-}C_6)$-alkyl, $(C_2\text{-}C_6)$-alkenyl, or $(C_2\text{-}C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, or $-CON(R_{23})_2$; or $R_1$ and $R_2$ may together form a three- to seven-membered cycloalkyl group, wherein the cycloalkyl group formed by $R_1$ and $R_2$ is optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, $-CON(R_{23})_2$, or $-(CH_2)_nOR_{23}$;

$R_3$ is one of the following:

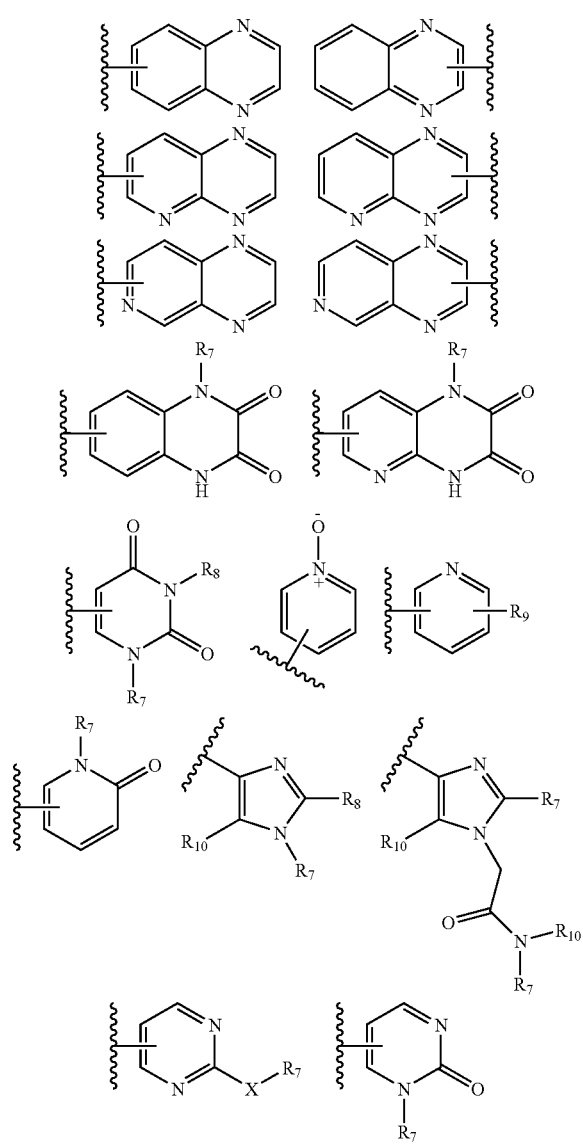

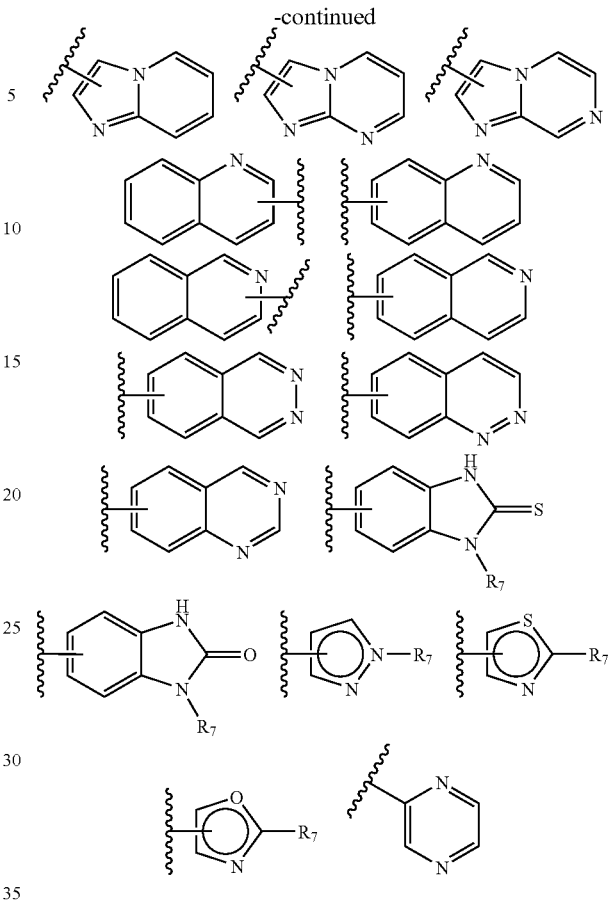

each $R_3$ also having up to three $R_{10}$ substituents attached to the ring of $R_3$ containing at least one N;

$R_4$, $R_5$, $R_{10}$, $R_{21}$, $R_{22}$, $R_{23}$, $R_{24}$, $R_{25}$, $R_{26}$, and $R_{27}$ are each independently hydrogen; or linear or branched $(C_1\text{-}C_6)$-alkyl, $(C_2\text{-}C_6)$-alkenyl, or $(C_2\text{-}C_6)$-alkynyl;

each $R_6$ is independently hydrogen; linear or branched $(C_1\text{-}C_6)$-alkyl, $(C_2\text{-}C_6)$-alkenyl, or $(C_2\text{-}C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, or $-CON(R_{23})_2$; $-NR_{13}R_{14}$; $-C(OH)(CF_3)_2$; $-CH(CF_3)_2$; $-C(CF_3)_3$; $-XR_{13}$; or $-COR_{13}$; and when the two $R_6$ are ortho to each other, they may together form a five- to seven-membered cyclic group containing up to 3 heteroatoms selected from N, O, or S, and wherein the cyclic group formed by the ortho $R_6$ groups is optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, $-CON(R_{23})_2$, or $-(CH_2)_nOR_{23}$;

$R_7$ and $R_9$ are each independently hydrogen; linear or branched $(C_1\text{-}C_6)$-alkyl, $(C_2\text{-}C_6)$-alkenyl, or $(C_2\text{-}C_6)$-alkynyl; $-(CH_2)_nXR_{12}$; $-(CH_2)_nR_{17}$; $-COXR_{11}$; $-XR_{11}$; $-CO_2R_{11}$; or $-CONR_{11}R_{12}$;

$R_8$ is hydrogen; linear or branched $(C_1\text{-}C_6)$-alkyl, $(C_2\text{-}C_6)$-alkenyl, or $(C_2\text{-}C_6)$-alkynyl; $-(CH_2)_mCO_2R_{11}$; or $-(CH_2)_mCONR_{11}R_{12}$;

$R_{11}$ and $R_{12}$ are each independently hydrogen; linear or branched $(C_1\text{-}C_6)$-alkyl, $(C_2\text{-}C_6)$-alkenyl, or $(C_2\text{-}C_6)$-alkynyl; or $R_{11}$ and $R_{12}$ may together form a three- to seven-membered heterocyclic group containing up to 3 heteroatoms selected from N, O, or S;

$R_{13}$ and $R_{14}$ are each independently hydrogen; linear or branched $(C_1-C_6)$-alkyl, $(C_2-C_6)$-alkenyl, or $(C_2-C_6)$-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$R_{23}CO_2R_{23}$, —$NR_{23}COR_{23}$, —$NR_{23}CON(R_{23})_2$, or —$CON(R_{23})_2$; aryl; or aryl optionally substituted with one to three substituents selected from halogen, $R_{15}$, —$OR_{15}$, or —$NR_{15}R_6$; or $R_{13}$ and $R_{14}$ may together form a three- to seven-membered heterocyclic group containing up to 3 heteroatoms selected from N, O, or S, and wherein the heterocyclic group formed by $R_{13}$ and $R_{14}$ is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_{15}$ and $R_{16}$ are each independently hydrogen; or linear or branched $(C_1-C_6)$-alkyl, $(C_2-C_6)$-alkenyl, or $(C_2-C_6)$-alkynyl; or both $R_{15}$ and $R_{16}$ may together form a three- to seven-membered heterocyclic group containing up to 3 heteroatoms selected from N, O, or S;

$R_{17}$ is phenyl, 2-pyridyl, 3-pyridyl, or 4-pyridyl;

$R_{18}$, $R_{19}$, and $R_{20}$ are each independently hydrogen; linear or branched $(C_1-C_6)$-alkyl, $(C_2-C_6)$-alkenyl, or $(C_2-C_6)$-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; halogen; —$NR_{13}R_{14}$; —C(OH)(CF$_3$)$_2$; —CH(CF$_3$)$_2$; —C(CF$_3$)$_3$; —$XR_{13}$; —$COR_{13}$; —$CO_2R_{13}$; or —$CON(R_{13})(R_{14})$;

X is —O—, —$NR_{12}$—, or —$SO_m$—;

each m is independently 0, 1, or 2; and each n is independently 0, 1, 2, 3, or 4.

28. A compound of the formula (IC):

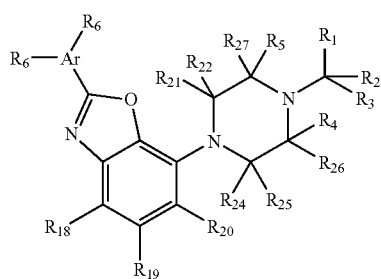

(IC)

prepared by a method comprising:

a) selectively reducing a compound of the formula (VII):

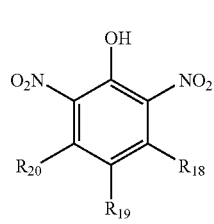

(VII)

thereby providing a compound having the formula (VIII):

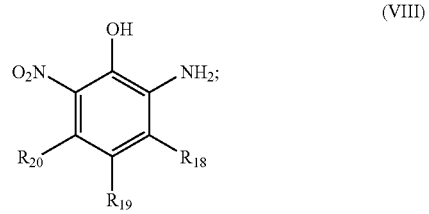

(VIII)

b) acylating the compound of the formula (VIII), thereby providing a compound having the formula (IX):

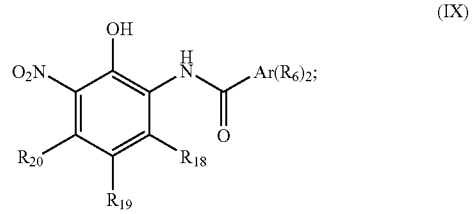

(IX)

c) reacting the compound of the formula (IX) under conditions effective to bring about cyclization to provide a compound of the formula (X):

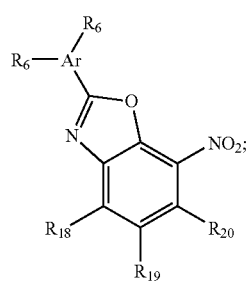

(X)

d) reacting the compound of the formula (X) under reductive conditions effective to provide a compound of the formula (XI):

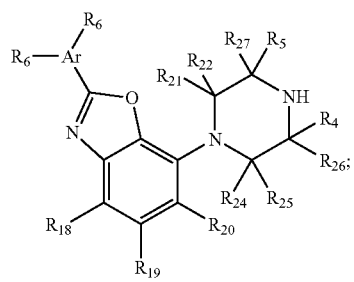

(XI)

e) reacting the free amine of the piperazine of the compound of formula (XI) under conditions effective to provide a compound of the formula (IC);

wherein

Ar is phenyl, 2-thiophenyl or 3-thiophenyl;

R₁ and R₂ are each independently hydrogen; or linear or branched (C₁-C₆)-alkyl, (C₂-C₆)-alkenyl, or (C₂-C₆)-alkynyl, each optionally substituted with halogen, —N₃, —NO₂, —CN, —OR₂₃, —SR₂₃, —SO₂R₂₃, —SO₂N(R₂₃)₂, —N(R₂₃)₂, —COR₂₃, —CO₂R₂₃, —NR₂₃CO₂R₂₃, —NR₂₃COR₂₃, —NR₂₃CON(R₂₃)₂, or —CON(R₂₃)₂; or R₁ and R₂ may together form a three- to seven-membered cycloalkyl group, wherein the cycloalkyl group formed by R₁ and R₂ is optionally substituted with halogen, —N₃, —NO₂, —CN, —OR₂₃, —SR₂₃, —SO₂R₂₃, —SO₂N(R₂₃)₂, —N(R₂₃)₂, —COR₂₃, —CO₂R₂₃, —NR₂₃CO₂R₂₃, —NR₂₃COR₂₃, —NR₂₃CON(R₂₃)₂, —CON(R₂₃)₂, or —(CH₂)OR₂₃;

R₃ is one of the following:

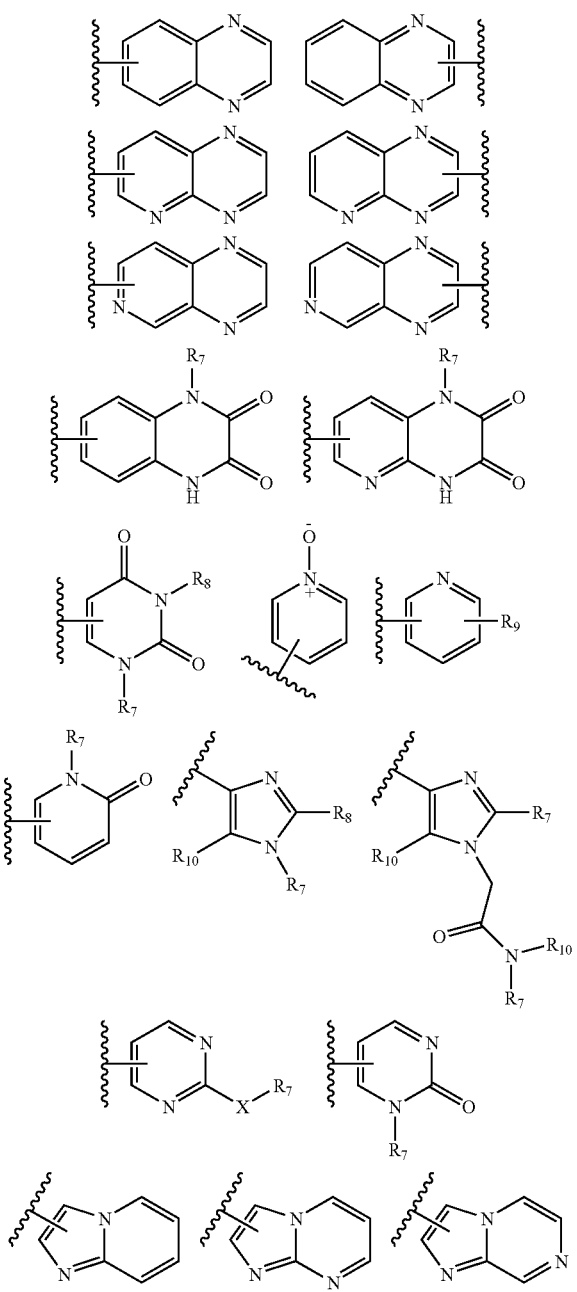
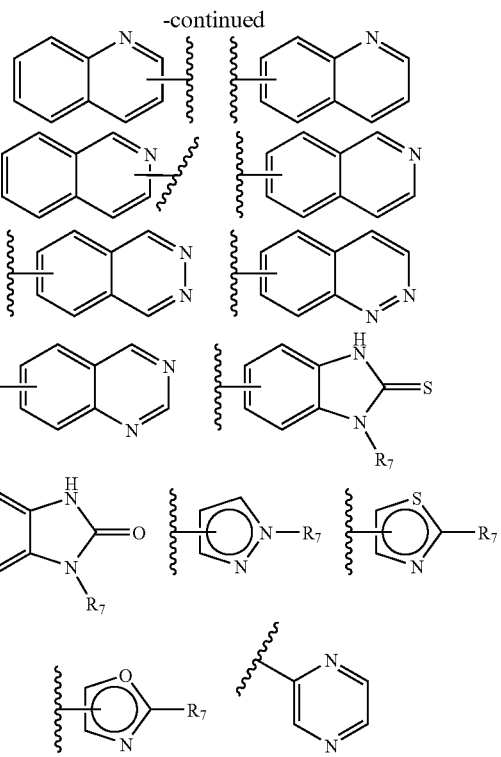

each R₃ also having up to three R₁₀ substitutents attached to the ring of R₃ containing at least one N;

R₄, R₅, R₁₀, R₂₁, R₂₂, R₂₃, R₂₄, R₂₅, R₂₆, and R₂₇ are each independently hydrogen; or linear or branched (C₁-C₆)-alkyl, (C₂-C₆)-alkenyl, or (C₂-C₆)-alkynyl;

each R₆ is independently hydrogen; linear or branched (C₁-C₆)-alkyl, (C₂-C₆)-alkenyl, or (C₂-C₆)-alkynyl, each optionally substituted with halogen, —N₃, —NO₂, —CN, —OR₂₃, —SR₂₃, —SO₂R₂₃, —SO₂N(R₂₃)₂, —N(R₂₃)₂, —COR₂₃, —CO₂R₂₃, —NR₂₃CO₂R₂₃, —NR₂₃COR₂₃, —NR₂₃CON(R₂₃)₂, or —CON(R₂₃)₂; —NR₁₃R₁₄; —C(OH)(CF₃)₂; —CH(CF₃)₂; —C(CF₃)₃; —XR₁₃; or —COR₁₃; and when the two R₆ are ortho to each other, they may together form a five- to seven-membered cyclic group containing up to 3 heteroatoms selected from N, O, or S, and wherein the cyclic group formed by the ortho R₆ groups is optionally substituted with halogen, —N₃, —NO₂, —CN, —OR₂₃, —SR₂₃, —SO₂R₂₃, —SO₂N(R₂₃)₂, —N(R₂₃)₂, —COR₂₃, —CO₂R₂₃, —NR₂₃CO₂R₂₃, —NR₂₃COR₂₃, —NR₂₃CON(R₂₃)₂, —CON(R₂₃)₂, or —(CH₂)ₙOR₂₃;

R₇ and R₉ are each independently hydrogen; linear or branched (C₁-C₆)-alkyl, (C₂-C₆)-alkenyl, or (C₂-C₆)-alkynyl; —(CH₂)ₙXR₁₂; —(CH₂)ₙR₁₇; —COXR₁₁; —XR₁₁; —CO₂R₁₁; or —CONR₁₁R₁₂;

R₈ is hydrogen; linear or branched (C₁-C₆)-alkyl, (C₂-C₆)-alkenyl, or (C₂-C₆)-alkynyl; —(CH₂)ₘCO₂R₁₁; or —(CH₂)ₘCONR₁₁R₁₂;

R₁₁ and R₁₂ are each independently hydrogen; linear or branched (C₁-C₆)-alkyl, (C₂-C₆)-alkenyl, or (C₂-C₆)-alkynyl; or R₁₁ and R₁₂ may together form a three- to seven-membered heterocyclic group containing up to 3 heteroatoms selected from N, O, or S;

R₁₃ and R₁₄ are each independently hydrogen; linear or branched (C₁-C₆)-alkyl, (C₂-C₆)-alkenyl, or (C₂-C₆)-alkynyl, each optionally substituted with halogen, —N₃, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —R$_{23}$CO$_2$R$_{23}$, —NR$_{23}$COR$_{23}$, —NR$_{23}$CON(R$_{23}$)$_2$, or —CON(R$_{23}$)$_2$; aryl; or aryl optionally substituted with one to three substituents selected from halogen, R$_{15}$, —OR$_{15}$, or —NR$_{15}$R$_{16}$; or R$_{13}$ and R$_{14}$ may together form a three- to seven-membered heterocyclic group containing up to 3 heteroatoms selected from N, O, or S, and wherein the heterocyclic group formed by R$_{13}$ and R$_{14}$ is optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —(CH$_2$)$_n$OR$_{23}$;

R$_{15}$ and R$_{16}$ are each independently hydrogen; or linear or branched (C$_1$-C$_6$)-alkyl, (C$_2$-C$_6$)-alkenyl, or (C$_2$-C$_6$)-alkynyl; or both R$_{15}$ and R$_{16}$ may together form a three- to seven-membered heterocyclic group containing up to 3 heteroatoms selected from N, O, or S;

R$_{17}$ is phenyl, 2-pyridyl, 3-pyridyl, or 4-pyridyl;

R$_{18}$, R$_{19}$, and R$_{20}$ are each independently hydrogen; linear or branched (C$_1$-C$_6$)-alkyl, (C$_2$-C$_6$)-alkenyl, or (C$_2$-C$_6$)-alkynyl, each optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, or —CON(R$_{23}$)$_2$; halogen; —NR$_{13}$R$_{14}$; —C(OH)(CF$_3$)$_2$; —CH(CF$_3$)$_2$; —C(CF$_3$)$_3$; —XR$_{13}$; —COR$_{13}$; —CO$_2$R$_{13}$; or —CON(R$_{13}$)(R$_{14}$);

X is —O—, —NR$_{12}$—, or —SO$_m$—;

each m is independently 0, 1, or 2; and each n is independently 0, 1, 2, 3, or 4.

29. A compound of the formula (IB):

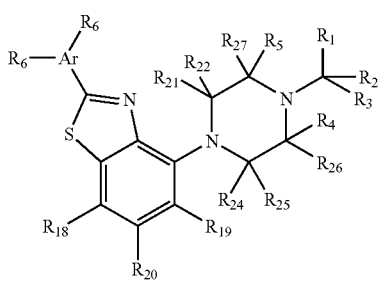

(IB)

prepared by a method comprising:

a) acylating a compound of the formula (XII):

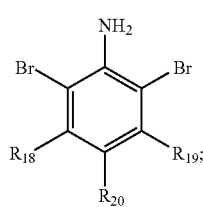

(XII)

thereby providing a compound having the formula (XIII):

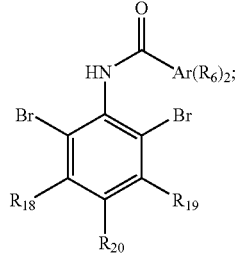

(XIII)

b) thiolating the compound of the formula (XIII), thereby providing a compound having the formula (XIV):

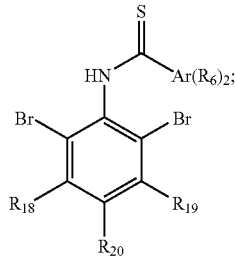

(XIV)

c) reacting the compound of the formula (XIV) under conditions effective to bring about cyclization to provide a benzothiazole ring and reacting with a piperazine to provide a compound of the formula (XV):

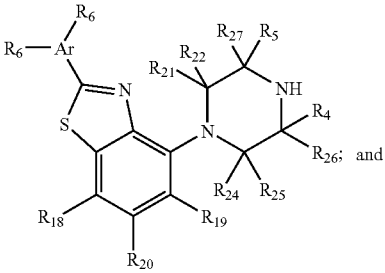

(XV)

d) reacting the free amine of the piperazine of the compound of the formula (XV) under conditions effective to provide a compound of the formula (IB);

wherein

Ar is phenyl, 2-thiophenyl or 3-thiophenyl;

R$_1$ and R$_2$ are each independently hydrogen; or linear or branched (C$_1$-C$_6$)-alkyl, (C$_2$-C$_6$)-alkenyl, or (C$_2$-C$_6$)-alkynyl, each optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, or —CON(R$_{23}$)$_2$; or R$_1$ and R$_2$ may together form a three- to seven-membered cycloalkyl group, wherein the cycloalkyl group formed by R$_1$ and R$_2$ is optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —(CH$_2$)OR$_{23}$;

R$_3$ is one of the following:

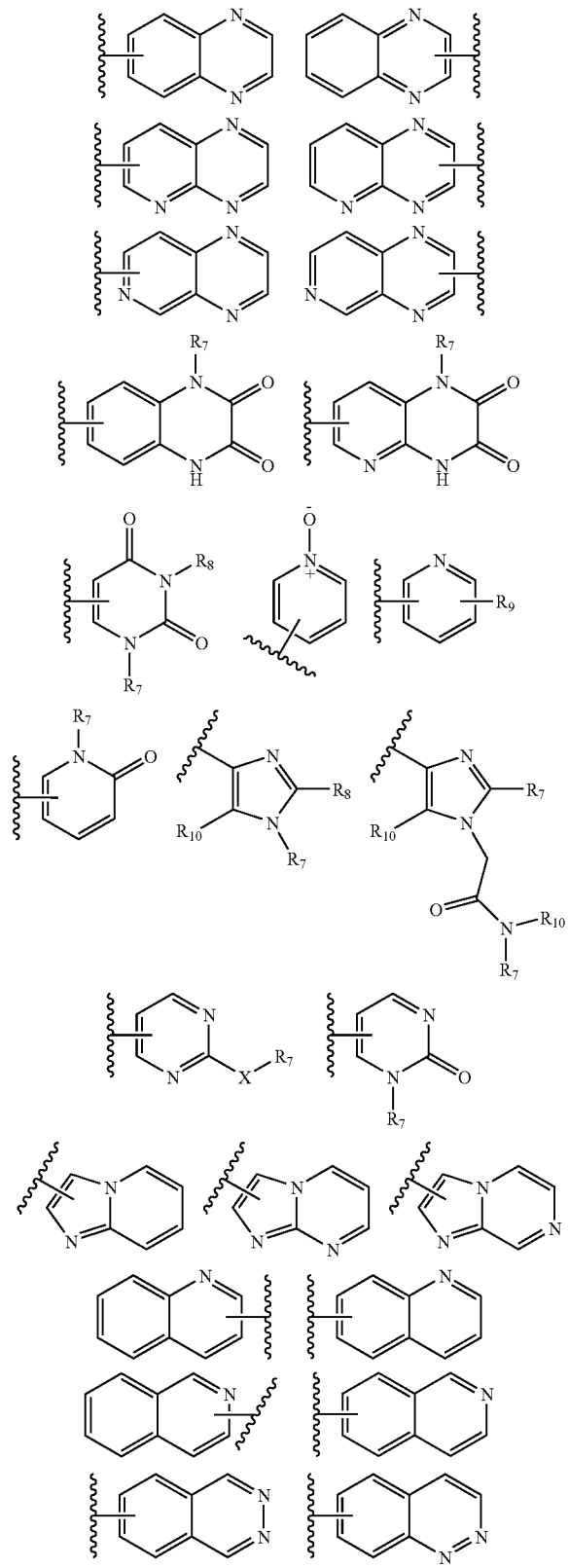

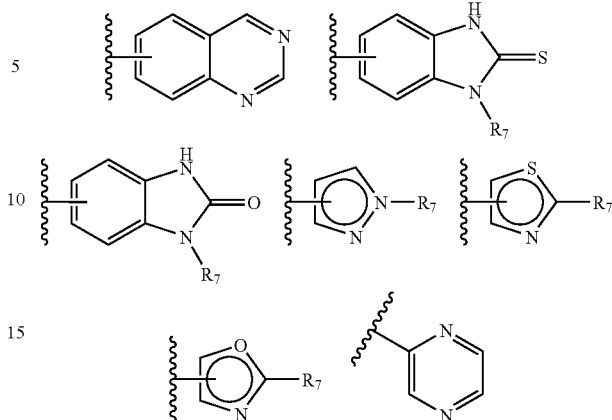

each R$_3$ also having up to three R$_{10}$ substituents attached to the ring of R$_3$ containing at least one N;

R$_4$, R$_5$, R$_{10}$, R$_{21}$, R$_{22}$, R$_{23}$, R$_{24}$, R$_{25}$, R$_{26}$, and R$_{27}$ are each independently hydrogen; or linear or branched (C$_1$-C$_6$)-alkyl, (C$_2$-C$_6$)-alkenyl, or (C$_2$-C$_6$)-alkynyl;

each R$_6$ is independently hydrogen; linear or branched (C$_1$-C$_6$)-alkyl, (C$_2$-C$_6$)-alkenyl, or (C$_2$-C$_6$)-alkynyl, each optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, or —CON(R$_{23}$)$_2$; —NR$_{13}$R$_{14}$; —C(OH)(CF$_3$)$_2$; —CH(CF$_3$)$_2$; —C(CF$_3$)$_3$; —XR$_{13}$; or —COR$_{13}$; and when the two R$_6$ are ortho to each other, they may together form a five- to seven-membered cyclic group containing up to 3 heteroatoms selected from N, O, or S, and wherein the cyclic group formed by the ortho R$_6$ groups is optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —(CH$_2$)$_n$OR$_{23}$;

R$_7$ and R$_9$ are each independently hydrogen; linear or branched (C$_1$-C$_6$)-alkyl, (C$_2$-C$_6$)-alkenyl, or (C$_2$-C$_6$)-alkynyl; —(CH$_2$)$_n$XR$_{12}$; —(CH$_2$)$_n$R$_{17}$; —COXR$_{11}$; —XR$_{11}$; —CO$_2$R$_{11}$; or —CONR$_{11}$R$_{12}$;

R$_8$ is hydrogen; linear or branched (C$_1$-C$_6$)-alkyl, (C$_2$-C$_6$)-alkenyl, or (C$_2$-C$_6$)-alkynyl; —(CH$_2$)$_m$CO$_2$R$_{11}$; or —(CH$_2$)$_m$CONR$_{11}$R$_{12}$;

R$_{11}$ and R$_{12}$ are each independently hydrogen; linear or branched (C$_1$-C$_6$)-alkyl, (C$_2$-C$_6$)-alkenyl, or (C$_2$-C$_6$)-alkynyl; or R$_{11}$ and R$_{12}$ may together form a three- to seven-membered heterocyclic group containing up to 3 heteroatoms selected from N, O, or S;

R$_{13}$ and R$_{14}$ are each independently hydrogen; linear or branched (C$_1$-C$_6$)-alkyl, (C$_2$-C$_6$)-alkenyl, or (C$_2$-C$_6$)-alkynyl, each optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —R$_{23}$CO$_2$R$_{23}$, —NR$_{23}$COR$_{23}$, —NR$_{23}$CON(R$_{23}$)$_2$, or —CON(R$_{23}$)$_2$; aryl; or aryl optionally substituted with one to three substituents selected from halogen, R$_{15}$, —OR$_{15}$, or —NR$_{15}$R$_{16}$; or R$_{13}$ and R$_{14}$ may together form a three- to seven-membered heterocyclic group containing up to 3 heteroatoms selected from N, O, or S, and wherein the heterocyclic group formed by R$_{13}$ and R$_{14}$ is optionally substituted with halogen, —N$_3$, —NO$_2$, —CN, —OR$_{23}$, —SR$_{23}$, —SO$_2$R$_{23}$, —SO$_2$N ($R_{23}$)$_2$, —N($R_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —(CH$_2$)$_n$OR$_{23}$;

$R_{15}$ and $R_{16}$ are each independently hydrogen; or linear or branched (C$_1$-C$_6$)-alkyl, (C$_2$-C$_6$)-alkenyl, or (C$_2$-C$_6$)-alkynyl; or both $R_{15}$ and $R_{16}$ may together form a three- to seven-membered heterocyclic group containing up to 3 heteroatoms selected from N, O, or S;

$R_{17}$ is phenyl, 2-pyridyl, 3-pyridyl, or 4-pyridyl;

$R_{18}$, $R_{19}$, and $R_{20}$ are each independently hydrogen; linear or branched (C$_1$-C$_6$)-alkyl, (C$_2$-C$_6$)-alkenyl, or (C$_2$-C$_6$)-alkynyl, each optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, or —CON(R$_{23}$)$_2$; halogen; —NR$_{13}$R$_{14}$; —C(OH)(CF$_3$)$_2$; —CH(CF$_3$)$_2$; —C(CF$_3$)$_3$; —XR$_{13}$; —COR$_{13}$; —CO$_2$R$_{13}$; or —CON(R$_{13}$)(R$_{14}$);

X is —O—, —NR$_{12}$—, or —SO$_m$—;

each m is independently 0, 1, or 2; and each n is independently 0, 1, 2, 3, or 4.

30. A compound of the formula (ID):

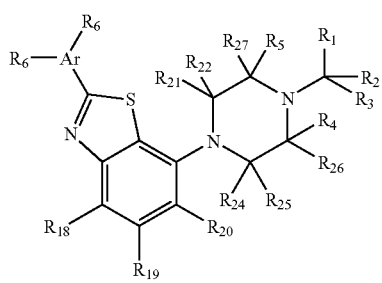

(ID)

prepared by a method comprising:

a) nitrating and then reducing a compound of the formula (XVI):

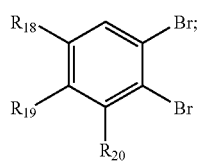

(XVI)

thereby providing a compound having the formula (XVII):

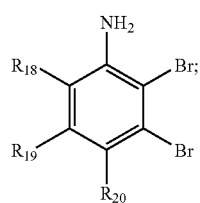

(XVII)

b) acylating the compound of the formula (XVII), thereby providing a compound having the formula (XVIII):

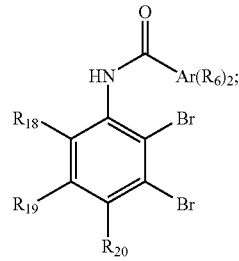

(XVIII)

c) thiolating the compound of the formula (XVIII), thereby providing a compound having the formula (XIX):

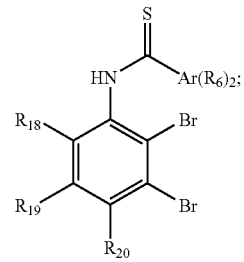

(XIX)

d) reacting the compound of the formula (XIX) under conditions effective to bring about cyclization to provide a benzothiazole ring and reacting with a piperazine to provide a compound of the formula (XX):

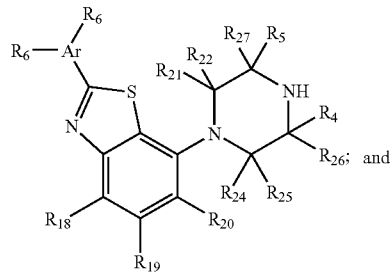

(XX)

e) reacting the free amine of the piperazine of the compound of the formula (XX) under conditions effective to provide a compound of the formula (ID);

wherein

Ar is phenyl, 2-thiophenyl or 3-thiophenyl;

$R_1$ and $R_2$ are each independently hydrogen; or linear or branched (C$_1$-C$_6$)-alkyl, (C$_2$-C$_6$)-alkenyl, or (C$_2$-C$_6$)-alkynyl, each optionally substituted with halogen, —N$_3$, —NO$_2$, —CN, —OR$_{23}$, —SR$_{23$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, or —CON(R$_{23}$)$_2$; or $R_1$ and $R_2$ may together form a three- to seven-membered cycloalkyl group, wherein the cycloalkyl group formed by $R_1$ and $R_2$ is optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —(CH$_2$)$_n$OR$_{23}$;

R$_3$ is one of the following:

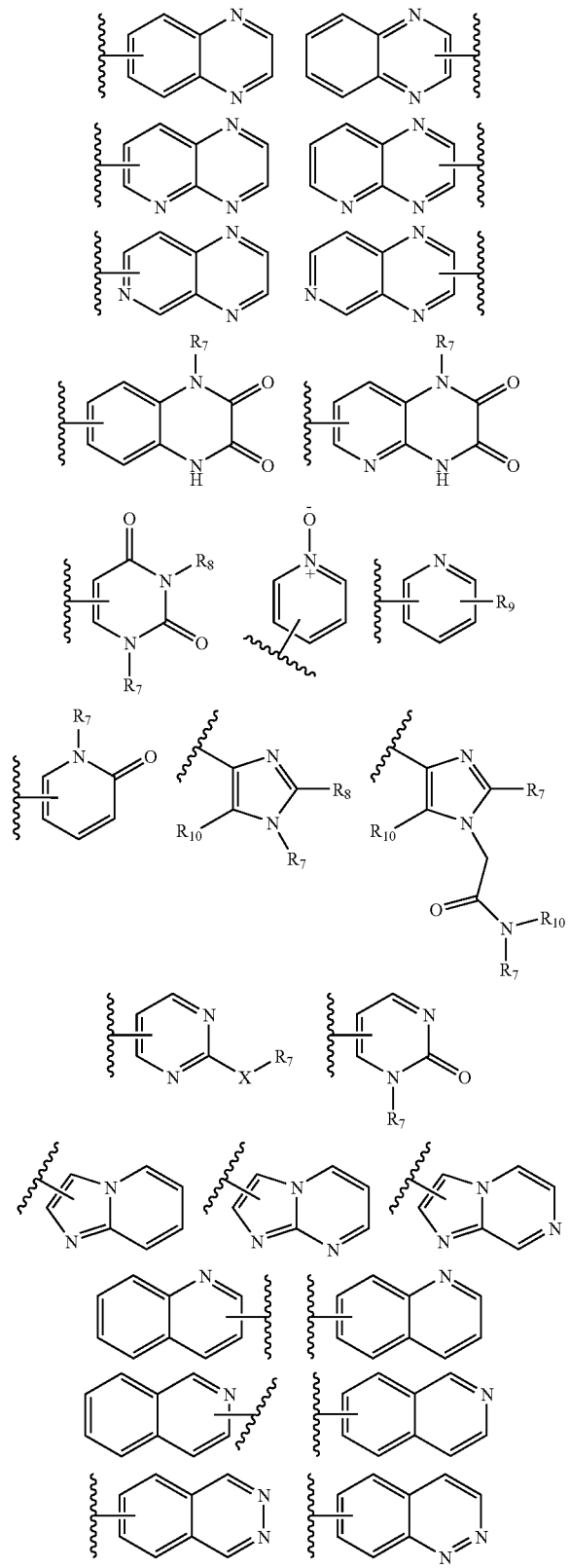

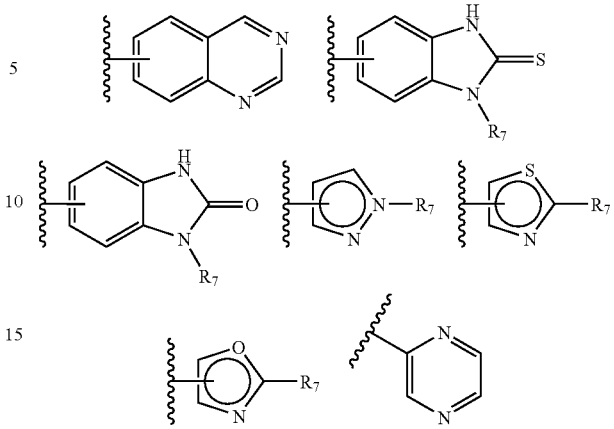

-continued each R$_3$ also having up to three R$_{10}$ substituents attached to the ring of R$_3$ containing at least one N;

R$_4$, R$_5$, R$_{10}$, R$_{21}$, R$_{22}$, R$_{23}$, R$_{24}$, R$_{25}$, R$_{26}$, and R$_{27}$ are each independently hydrogen; or linear or branched (C$_1$-C$_6$)-alkyl, (C$_2$-C$_6$)-alkenyl, or (C$_2$-C$_6$)-alkynyl;

each R$_6$ is independently hydrogen; linear or branched (C$_1$-C$_6$)-alkyl, (C$_2$-C$_6$)-alkenyl, or (C$_2$-C$_6$)-alkynyl, each optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, or —CON(R$_{23}$)$_2$; —NR$_{13}$R$_{14}$; —C(OH)(CF$_3$)$_2$; —CH(CF$_3$)$_2$; —C(CF$_3$)$_3$; —XR$_{13}$; or —COR$_{13}$; and when the two R$_6$ are ortho to each other, they may together form a five- to seven-membered cyclic group containing up to 3 heteroatoms selected from N, O, or S, and wherein the cyclic group formed by the ortho R$_6$ groups is optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —(CH$_2$)$_n$OR$_{23}$;

R$_7$ and R$_9$ are each independently hydrogen; linear or branched (C$_1$-C$_6$)-alkyl, (C$_2$-C$_6$)-alkenyl, or (C$_2$-C$_6$)-alkynyl; —(CH$_2$)$_n$XR$_{12}$; —(CH$_2$)$_n$R$_{17}$; —COXR$_{11}$; —XR$_{11}$; —CO$_2$R$_{11}$; or —CONR$_{11}$R$_{12}$;

R$_8$ is hydrogen; linear or branched (C$_1$-C$_6$)-alkyl, (C$_2$-C$_6$)-alkenyl, or (C$_2$-C$_6$)-alkynyl; —(CH$_2$)$_m$CO$_2$R$_{11}$; or —(CH$_2$)$_m$CONR$_{11}$R$_{12}$;

R$_{11}$ and R$_{12}$ are each independently hydrogen; linear or branched (C$_1$-C$_6$)-alkyl, (C$_2$-C$_6$)-alkenyl, or (C$_2$-C$_6$)-alkynyl; or R$_{11}$ and R$_{12}$ may together form a three- to seven-membered heterocyclic group containing up to 3 heteroatoms selected from N, O, or S;

R$_{13}$ and R$_{14}$ are each independently hydrogen; linear or branched (C$_1$-C$_6$)-alkyl, (C$_2$-C$_6$)-alkenyl, or (C$_2$-C$_6$)-alkynyl, each optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —R$_{23}$CO$_2$R$_{23}$, —NR$_{23}$COR$_{23}$, —NR$_{23}$CON(R$_{23}$)$_2$, or —CON(R$_{23}$)$_2$; aryl; or aryl optionally substituted with one to three substituents selected from halogen, R$_{15}$, —OR$_{15}$, or —NR$_{15}$R$_{16}$; or R$_{13}$ and R$_{14}$ may together form a three- to seven-membered heterocyclic group containing up to 3 heteroatoms selected from N, O, or S, and wherein the heterocyclic group formed by R$_{13}$ and R$_{14}$ is optionally substituted with halogen, —N$_3$, —NO$_2$, —CN, —OR$_{23}$, —SR$_{23}$, —SO$_2$R$_{23}$, —SO$_2$N $(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, $-CON(R_{23})_2$, or $-(CH_2)_nOR_{23}$;

$R_{15}$ and $R_{16}$ are each independently hydrogen; or linear or branched $(C_1\text{-}C_6)$-alkyl, $(C_2\text{-}C_6)$-alkenyl, or $(C_2\text{-}C_6)$-alkynyl; or both $R_{15}$ and $R_{16}$ may together form a three- to seven-membered heterocyclic group containing up to 3 heteroatoms selected from N, O, or S;

$R_{17}$ is phenyl, 2-pyridyl, 3-pyridyl, or 4-pyridyl;

$R_{18}$, $R_{19}$, and $R_{20}$ are each independently hydrogen; linear or branched $(C_1\text{-}C_6)$-alkyl, $(C_2\text{-}C_6)$-alkenyl, or $(C_2\text{-}C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, or $-CON(R_{23})_2$; halogen; $-NR_{13}R_{14}$; $-C(OH)(CF_3)_2$; $-CH(CF_3)_2$; $-C(CF_3)_3$; $-XR_{13}$; $-COR_{13}$; $-CO_2R_{13}$; or $-CON(R_{13})(R_{14})$;

X is $-O-$, $-NR_{12}-$, or $-SO_m-$;

each m is independently 0, 1, or 2; and each n is independently 0, 1, 2, 3, or 4.

\* \* \* \* \*